United States Patent
Mcbrady et al.

(10) Patent No.: US 11,852,568 B2
(45) Date of Patent: Dec. 26, 2023

(54) APPARATUSES, SYSTEMS, AND METHODS FOR SAMPLE CAPTURE AND EXTRACTION

(71) Applicant: Hand Held Products, Inc., Charlotte, NC (US)

(72) Inventors: Adam Dewey Mcbrady, Dallas, TX (US); Moin Shafai, Plano, TX (US); Oscar Ponte Rivas, Mexico City (MX); Aoife Celoria, Quinlan, TX (US); Philip C. Foster, Murphy, TX (US); Dustin Michael Brandt, Tempe, AZ (US); Giorgio Carlo Isella, Torrance, CA (US); Jose Guadalupe Sanchez De La Rosa, Naucalpan (MX); Emir Rahislic, Des Plaines, IL (US); Amanda Esther Sall Childers, Des Plaines, IL (US); Gennady Germaine, Cherry Hill, NJ (US); Thomas Merritt Haggerty, Collingswood, NJ (US)

(73) Assignee: Hand Held Products, Inc., Charlotte, NC (US)

(*) Notice: Subject to any disclaimer, the term of this patent is extended or adjusted under 35 U.S.C. 154(b) by 34 days.

(21) Appl. No.: 17/446,688

(22) Filed: Sep. 1, 2021

(65) Prior Publication Data

US 2022/0136935 A1    May 5, 2022

Related U.S. Application Data

(63) Continuation of application No. 17/302,535, filed on May 5, 2021.

(Continued)

(51) Int. Cl.
*G01N 1/22* (2006.01)

(52) U.S. Cl.
CPC ... *G01N 1/2205* (2013.01); *G01N 2001/2223* (2013.01)

(58) Field of Classification Search
CPC ......... G01N 1/2205; G01N 2001/2223; G01N 2001/2217; G01N 2001/2244;
(Continued)

(56) References Cited

U.S. PATENT DOCUMENTS

| 4,564,021 A | 1/1986 | Siegmann et al. |
| 5,787,885 A | 8/1998 | Emelson |

(Continued)

FOREIGN PATENT DOCUMENTS

| AU | 2013204332 B2 | 7/2015 |
| CN | 102288293 A | 12/2011 |

(Continued)

OTHER PUBLICATIONS

Kratskin, Igor L, et al. "An Easily Constructed Pipette for Pressure Microinjections into the Brain." Brain Research Bulletin, vol. 44, No. 2, 1997, pp. 199-203., https://doi.org/10.1016/s0361-9230(97)00092-0 (Year: 1997).*

(Continued)

*Primary Examiner* — Jennifer Wecker
*Assistant Examiner* — Ali Husain Faraz
(74) *Attorney, Agent, or Firm* — Alston & Bird LLP

(57) ABSTRACT

Methods, apparatuses, and systems associated with aerosol collection devices (such as, but not limited to, breath-aerosol collector devices, breathalyzers) are provided. An example aerosol collection device includes a sample transfer adapter configured to receive a sample and a device body connected to the sample transfer adapter. In some examples, the device body defines a flow channel that guides the sample to a filter component, and the filter component contains a buffer solution.

19 Claims, 60 Drawing Sheets

Related U.S. Application Data

(60) Provisional application No. 63/154,476, filed on Feb. 26, 2021, provisional application No. 63/198,609, filed on Oct. 29, 2020.

(58) Field of Classification Search
CPC .... G01N 1/405; G01N 1/2214; G01N 1/2202; G01N 1/2247; G01N 2001/227; A61B 5/097; A61B 10/00; A61B 2010/0087
See application file for complete search history.

(56) References Cited

U.S. PATENT DOCUMENTS

| | | |
|---|---|---|
| 5,961,924 A | 10/1999 | Reichert et al. |
| 6,033,368 A | 3/2000 | Gaston et al. |
| 6,192,168 B1 | 2/2001 | Feldstein et al. |
| 6,624,894 B2 | 9/2003 | Olszak et al. |
| 6,903,820 B2 | 6/2005 | Wang |
| 6,955,650 B2 | 10/2005 | Mault et al. |
| 7,024,066 B1 | 4/2006 | Malendevich et al. |
| 7,048,776 B2 | 5/2006 | Moore et al. |
| 7,052,854 B2 | 5/2006 | Melker et al. |
| 7,313,280 B2 | 12/2007 | Murai et al. |
| 7,347,825 B2 | 3/2008 | Vaughan et al. |
| 8,279,445 B2 | 10/2012 | Dominguez Horna et al. |
| 8,279,448 B2 | 10/2012 | Kim et al. |
| 8,361,392 B2 | 1/2013 | Lee et al. |
| 8,403,178 B2 | 3/2013 | May et al. |
| 8,654,344 B2 | 2/2014 | Borot et al. |
| 8,928,875 B2 | 1/2015 | Braeckmans et al. |
| 9,004,736 B1 | 4/2015 | Srinivas et al. |
| 9,157,804 B2 | 10/2015 | Messerschmidt |
| 9,169,521 B1 * | 10/2015 | Rajagopal ............ B01L 3/5027 |
| 9,202,833 B2 | 12/2015 | Mackey |
| 9,257,814 B1 | 2/2016 | Djordjevic et al. |
| 9,273,949 B2 | 3/2016 | Bornhop et al. |
| 9,310,185 B2 | 4/2016 | Lloret Soler et al. |
| 9,322,767 B2 | 4/2016 | Ehrenkranz |
| 9,450,381 B1 | 9/2016 | Cai et al. |
| 9,638,858 B2 | 5/2017 | Luo et al. |
| 9,690,093 B2 | 6/2017 | Margallo Balbás et al. |
| 9,739,594 B2 | 8/2017 | Koerner et al. |
| 9,804,510 B2 | 10/2017 | Hamaya et al. |
| 9,964,703 B2 | 5/2018 | Parker et al. |
| 9,976,844 B2 | 5/2018 | Lloret Soler et al. |
| 9,988,691 B2 | 6/2018 | Sislian et al. |
| 10,042,131 B1 | 8/2018 | Lesea |
| 10,261,013 B2 | 4/2019 | Bornhop et al. |
| 10,359,417 B2 | 7/2019 | Hammarlund et al. |
| 10,473,665 B2 | 11/2019 | Trowell et al. |
| 10,527,784 B1 | 1/2020 | Koste et al. |
| 10,591,284 B2 | 3/2020 | Deck et al. |
| 10,591,460 B1 | 3/2020 | Ahmad et al. |
| 10,627,210 B2 | 4/2020 | Habrich |
| 10,670,939 B2 | 6/2020 | Liu et al. |
| 2002/0057884 A1 | 5/2002 | Hirose et al. |
| 2003/0152304 A1 | 8/2003 | Gonthier et al. |
| 2004/0127808 A1 | 7/2004 | Vaughan et al. |
| 2005/0137491 A1 | 6/2005 | Paz et al. |
| 2006/0051010 A1 | 3/2006 | Chu et al. |
| 2007/0062255 A1 | 3/2007 | Talton |
| 2007/0223002 A1 | 9/2007 | Masri et al. |
| 2008/0186504 A1 | 8/2008 | Kiesel et al. |
| 2009/0040524 A1 | 2/2009 | Joung |
| 2009/0152267 A1 | 6/2009 | May et al. |
| 2009/0255953 A1 | 10/2009 | May et al. |
| 2010/0009456 A1 | 1/2010 | Prins et al. |
| 2011/0236273 A1 | 9/2011 | Claussen et al. |
| 2011/0310378 A1 | 12/2011 | Froggatt et al. |
| 2012/0147228 A1 | 6/2012 | Duparréet al. |
| 2012/0174650 A1 | 7/2012 | Ariessohn et al. |
| 2013/0142477 A1 | 6/2013 | Diemeer |
| 2013/0321677 A1 | 12/2013 | Cote et al. |
| 2014/0080729 A1 | 3/2014 | Grego et al. |
| 2015/0226609 A1 | 8/2015 | Cho |
| 2016/0041138 A1 | 2/2016 | Pycke et al. |
| 2016/0187333 A1 | 6/2016 | Moll et al. |
| 2016/0349454 A1 | 12/2016 | Zhang et al. |
| 2017/0016638 A1 | 1/2017 | Yun |
| 2017/0067882 A1 | 3/2017 | Bornhop et al. |
| 2017/0097287 A1 | 4/2017 | Clavaguera et al. |
| 2017/0303822 A1 | 10/2017 | Allsworth et al. |
| 2017/0303823 A1 | 10/2017 | Allsworth et al. |
| 2017/0324482 A1 | 11/2017 | Kato et al. |
| 2017/0370703 A1 | 12/2017 | Wang et al. |
| 2018/0003706 A1 | 1/2018 | Mavinkurve et al. |
| 2018/0128600 A1 | 5/2018 | T Hooft |
| 2018/0128680 A1 | 5/2018 | Kim |
| 2018/0155782 A1 | 6/2018 | Zhong |
| 2018/0306775 A1 | 10/2018 | Beck et al. |
| 2019/0167152 A1 | 6/2019 | Weda et al. |
| 2019/0274588 A1 | 9/2019 | Cardin |
| 2019/0275357 A1 | 9/2019 | Palmer, Jr. et al. |
| 2019/0339466 A1 | 11/2019 | Heck et al. |
| 2020/0006088 A1 | 1/2020 | Yu et al. |
| 2020/0025611 A1 | 1/2020 | Mai et al. |
| 2020/0025631 A1 | 1/2020 | Howells et al. |
| 2020/0096450 A1 | 3/2020 | Zhong et al. |
| 2020/0156076 A1 | 5/2020 | Crescenzi et al. |
| 2020/0220329 A1 | 7/2020 | Siriani et al. |
| 2021/0016276 A1 | 1/2021 | Chiu et al. |
| 2021/0076979 A1 | 3/2021 | O'Brien et al. |
| 2021/0349018 A1 | 11/2021 | Venkatarayalu et al. |
| 2022/0003670 A1 | 1/2022 | Mcbrady et al. |

FOREIGN PATENT DOCUMENTS

| | | |
|---|---|---|
| CN | 102322876 A | 1/2012 |
| CN | 103884683 B | 4/2016 |
| CN | 106482834 A | 3/2017 |
| CN | 107101575 A | 8/2017 |
| CN | 207570561 U | 7/2018 |
| CN | 108592964 A | 9/2018 |
| CN | 109946463 A | 6/2019 |
| CN | 110077703 A | 8/2019 |
| CN | 110081817 A | 8/2019 |
| CN | 110112649 A | 8/2019 |
| CN | 209215662 U | 8/2019 |
| CN | 110401101 A | 11/2019 |
| CN | 110672556 A | 1/2020 |
| CN | 110703385 A | 1/2020 |
| CN | 210149831 U | 3/2020 |
| CN | 210405999 U | 4/2020 |
| CN | 210427333 U | 4/2020 |
| EP | 2017602 A1 | 1/2009 |
| EP | 3907494 A1 | 11/2021 |
| EP | 4239318 A2 | 9/2023 |
| GB | 2437543 A | 4/2006 |
| JP | 2004-125624 A | 4/2004 |
| JP | 2004-145246 A | 5/2004 |
| JP | 2020-020990 | 2/2020 |
| KR | 10-0839268 B1 | 6/2008 |
| KR | 10-2015-0059436 A | 6/2015 |
| RU | 2690319 C1 | 5/2019 |
| WO | 1998/044970 A1 | 10/1998 |
| WO | 2004/020987 A1 | 3/2004 |
| WO | 2009/010624 A1 | 1/2009 |
| WO | 2009/022028 A1 | 2/2009 |
| WO | 2010/090599 A1 | 8/2010 |
| WO | 2017/153378 A1 | 9/2017 |
| WO | 2019/178247 A1 | 9/2019 |
| WO | 2020/005431 A1 | 1/2020 |
| WO | 2020/031751 A1 | 2/2020 |
| WO | 2020/037307 A1 | 2/2020 |
| WO | 2020/141463 A2 | 7/2020 |
| WO | 2021/202929 A1 | 10/2021 |

OTHER PUBLICATIONS

Patil, Satyashodhan. "Technical Considerations for Designing Syringes and Other Drug-Delivery Devices." Mddionline.com, Jul. 23, 2019, https://www.mddionline.com/design -engineering/designing-drug-delivery-device-read-first (Year: 2019).*

(56) References Cited

OTHER PUBLICATIONS

Advisory Action (PTOL-303) dated Jul. 10, 2023 for U.S. Appl. No. 17/302,535, 3 page(s).
European search report dated Jul. 17, 2023 for EP Application No. 23152603, 14 page(s).
European search report dated Nov. 9, 2021 for EP Application No. 21172819, 8 page(s).
European search report dated Sep. 24, 2021 for EP Application No. 21172749, 12 page(s).
Examiner Interview Summary Record (PTOL-413) dated Jul. 10, 2023 for U.S. Appl. No. 17/302,535, 1 page(s).
Non-Final Rejection dated Nov. 18, 2022 for U.S. Appl. No. 17/302,535, 16 page(s).
Notice of Allowance and Fees Due (PTOL-85) dated Jul. 12, 2023 for U.S. Appl. No. 17/446,684, 8 page(s).
Sevin-Landais et al., "Functional immobilisation of the nicotinic acetylcholine receptor in tethered lipid membranes," Biophysical Chemistry, 85:141-152, (2000).
Final Rejection dated Apr. 11, 2023 for U.S. Appl. No. 17/302,535, 12 page(s).
Final Rejection dated Apr. 11, 2023 for U.S. Appl. No. 17/446,684, 17 page(s).
Igor L Kratskin, XiaosongYu, Richard L Doty, An Easily Constructed Pipette for Pressure Microinjections Into the Brain, Brain Research Bulletin, vol. 44, Issue 2, 1997, pp. 199-203, ISSN 0361-9230,https://doi.org/10.1016/S0361-9230(97)00092-0 (Year: 1997).
List of references Mailed on Apr. 3, 2023 for U.S. Appl. No. 17/446,686, 1 page(s).
Non-Final Rejection dated Apr. 3, 2023 for U.S. Appl. No. 17/446,686, 17 page(s).
Partial European Search Report for EP No. 22197548.5 received Feb. 16, 2023.
Kratskin, Igor et al., "An Easily Constructed Pipette for Pressure Microinjections Into the Brain," Brain Research Bulletin, 44(2):199-203, (1997).
Non-Final Rejection dated Nov. 18, 2022 for U.S. Appl. No. 17/302,535.
European search report dated May 8, 2023 for EP Application No. 22197548, 13 page(s).
List of references Mailed on Nov. 25, 2022 for U.S. Appl. No. 17/446,684.
Non-Final Rejection dated Nov. 25, 2022 for U.S. Appl. No. 17/446,684.
"Industry News: New 'saliva test' to instantly detect coronavirus with lasers," Select Science Apr. 7, 2020, (5 pages), https://www.selectscience.net/industry-news/new-saliva-test-to-instantly-detect-coronavirus-with-lasers/?artID=51173.
"Integrate Breath Biopsy." Owlstone Medical, https://www.owlstonemedical.com/breath-biopsy-covid-19-research/.
"Interferometry explained," Renishaw, https://www.renishaw.com/en/interferometry-explained-7854.
Agranovski, et al. "Comparative Study of the Performance of Nine Filters Utilized in Filtration of Aerosols by Bubbling," Aerosol Science and Technology, 2001, 35:4, 852-859, DOI: 10.1080/027868201753227415.
Agranovski, et al. "New personal sampler for viable airborne viruses: feasibility study," Journal of Aerosol Science, vol. 36, Issues 5-6, 2005, pp. 609-617. https://doi.org/10.1016/j.jaerosci.2004.11.014.
Azevedo, M. "E25Bio Raises $2M From Khosla Ventures To Create Rapid COVID-19 Diagnostic Test," Crunchbase News, Mar. 18, 2020. https://news.crunchbase.com/news/e25bio-raises-2m-from-khosla-ventures-to-create-rapid-covid-19-diagnostic-test/.
Bellamy IIII, W. "Halo Sensor Advances IoT Concept of Wireless Cabin Air Quality Monitoring," Aviation Today, Jun. 12, 2020 (7 pages). https://www.aviationtoday.com/2020/06/12/halo-sensor-advances-iot-concept-wireless-cabin-air-quality-monitoring/.
BioOptics World Editors. "Optical method could cut Coronavirus diagnosis time to 15 minutes," Laser Focus World, Mar. 10, 2020 (5 pages). https://www.laserfocusworld.com/biooptics/biomedicine/article/14195374/optical-method-could-cut-coronavirus-diagnosis-time-to-15-minutes.
Biophotonics, "Plasmonic Biosensor Uses Thermal and Optical Methods to Detect Coronavirus," Photonics Media, Jul./Aug. 2020, https://www.photonics.com/Articles/Plasmonic_Biosensor_Uses_Thermal_and_Optical/a65734.
Campbell D.P. (2008) Interferometric Biosensors. In: Zourob M., Elwary S., Turner A. (eds) Principles of Bacterial Detection: Biosensors, Recognition Receptors and Microsystems. Springer, New York, NY. https://doi.org/10.1007/978-0-387-75113-9_9.
Chaghajerdi, A. "Sensing and Control in Optical Drives: How to Read Data from a Clear Disc," in IEEE Control Systems Magazine, vol. 28, No. 3, pp. 23-29, Jun. 2008, doi: 10.1109/MCS.2008.920436.
Collimation of Astigmatic Diode Laser Beam by Objective Lens, LightTrans International GmbH. Retrieved from https://www.lighttrans.com/fileadmin/shared/UseCases/Application_UC_Collimation%20of%20Astigmatic%20Diode%20Laser.pdf.
Communication from Photonics 21. "Photonics21 to develop saliva test to detect Covid-19 with lasers," Science Business, Apr. 7, 2020 (6 pages). https://sciencebusiness.net/network-updates/photonics21-develop-saliva-test-detect-covid-19-lasers.
Covid-19 diagnose, faster and cheaper, nanbiosis (2 pages). https://www.nanbiosis.es/covid-19-diagnose-faster-and-cheaper/.
Deck, L. "High-performance multi-channel fiber-based absolute distance measuring interferometer system," Proceedings vol. 7405, Instrumentation, Metrology, and Standards for Nanomanufacturing III; 74050E (2009), 9 pages. https://doi.org/10.1117/12.826253.
Duval, et al. "Nanophotonic lab-on-a-chip platforms including novel bimodal interferometers, microfluidics and grating couplers," Lab on a chip, 2012, 12(11): 1987-1994. 10.1039/c2lc40054e.
Extended European Search Report issued in European Application No. 21172819.1 dated Nov. 9, 2021, 9 pages.
Extended European Search Report issued in European Application No. 21172749.0 dated Sep. 24, 2021, 12 pages.
Gao, et al. "Airborne Wireless Sensor Networks for Airplane Monitoring System," Hindawi Wireless Communications and Mobile Computing, vol. 2018, Article ID 6025825, 18 pages. DOI: https://doi.org/10.1155/2018/6025825.
Garcia, D. Lab-on-A-Chip Integration of the Bimodal Waveguide Nanointerferometric Biosensor. 2018. Autonomous University of Barcelona. PhD Dissertation.
Gonzalez, Ana Belen. A Bimodal Waveguide Interferometer Device Based on Silicon Photonics Technology for Label-free and High Sensitive Biosensing. 2012. The Autonomous University of Barcelona. PhD Thesis.
González-Guerrero, et al. "Advanced photonic biosensors for point-of-care diagnostics," Procedia Engineering, vol. 25, 2011, pp. 71-75, ISSN 1877-7058. DOI:https://doi.org/10.1016/j.proeng_2011.12.018.
Halo IOT Smart Sensor [retrieved on Dec. 15, 2021] retrieved on the internet from <URL:https://ipvideocorp.com/halo/> (15 pages).
Halo IOT Smart Sensor Mechanical Specifications. IPVideoCorp. https://ipvideocorp.com/halo-tech-specs/.
Halo Smart Sensor. IP Video Corp. https://ipvideocorp.com/wp-content/uploads/2020/02/HALO_General_2.10.20.pdf.
Hamed, A. "Image Processing of Corona Virus Using Interferometry," Optics and Photonics Journal, 2016, 6, 75-86.
Hong, et al. "Gentle Sampling of Submicrometer Airborne Virus Particles using a Personal Electrostatic Particle Concentrator" Environ. Sci. Technol. 2016, 50, 22, 12365-12372.
Liang, et al. "Bimodal Waveguide Interferometer RI Sensor Fabricated on Low-Cost Polymer Platform," IEEE Photonics Journal, vol. 11, No. 2, pp. 1-8, Apr. 2019, Art No. 6801108, doi: 10.1109/JPHOT.2019.2900741.
Martino, et al. "Reference interferometer using a semiconductor laser/LED reference source in a cryogenic Fourier-transform spectrometer," Proceedings, Cryogenic Optical Systems and Instruments VIII, 1998, vol. 3435, 1998 (11 pages), https://doi.org/10.1117/12.323746.

(56) References Cited

OTHER PUBLICATIONS

McDevitt, et al. "Development and Performance Evaluation of an Exhaled-Breath Bioaerosol Collector," Aerosol Sci Technology, 2013, 47(4):444-451. doi: 10.1080/02786826.2012.762973.

Miller, et al. "A Handheld Electrostatic Precipitator for Sampling Airborne Particles and Nanoparticles," Aerosol Science and Technology, 2010, 44:6, 417-427, DOI: 10.1080/02786821003692063.

National Research Council. 2002. The Airliner Cabin Environment and the Health of Passengers and Crew. Washington, DC: The National Academies Press.https://doi.org/10.17226/10238.

New research projects on Coronavirus, Oct. 22, 2020, European Commission (4 pages). https://ec.europa.eu/info/sites/default/files/research_and_innovation/research_by_area/documents/ec_rtd_cv-projects.pdf.

Ruiz-Vega, et al. "Nanophotonic biosensors for point-of-care COVID-19 diagnostics and coronavirus surveillance," J. Phys. Photonics 3 (2021) 011002, pp. 1-8.

SARS-COV-2 Airborne Detection. Smiths Detection. https://www.smithsdetection.com/.

Schmit, Joanna. An Introduction to non-contact surface metrology. 2007, https://cupdf.com/document/an-introduction-to-non-contact-surface-metrology-dr-an-introduction-to-non-contact.html.

Trafton, et al. "Covid-19 diagnostic based on MIT technology might be tested on patient samples soon," MIT News on Campus and Around the World, Massachusetts Institute of Technology, Mar. 12, 2020, https://news.mit.edu/2020/covid-19-diagnostic-test-prevention-0312.

Usachev, et al. "Multiplexed Surface Plasmon Resonance based real time viral aerosol detection," Journal of Aerosol Science, 90 (2015): 136-143. https://doi.org/10.1016/j.jaerosci.2015.08.009.

Wallace, J. "New saliva test to instantly detect coronavirus via interferometric laser technology," Laser Focus World, Apr. 7, 2020 (7 pages). https://www.laserfocusworld.com/test-measurement/article/14173589/new-saliva-test-to-instantly-detect-coronavirusvia-interferometric-laser-technology.

Waltz, E. "Can Sensors that Detect Coronavirus in the Air Help Economies Reopen Safely?" IEEE Spectrum, Jun. 18, 2020, https://spectrum.ieee.org/devices-monitor-coronavirus-in-the-air.

Wragg, et al. "An automated online instrument to quantify aerosol-bound reactive oxygen species (ROS) for ambient measurement and health-relevant aerosol studies," in Atmos. Meas. Tech., 9, 4891-4900, 2016. doi: 10.5194/amt-9-4891-2016.

Ymeti, A. Development of a multichannel integrated young interferometer immunosensor. 2004. PhD Thesis. University of Twente.

Zinoviev, et al. "Integrated Bimodal Waveguide Interferometric Biosensor for Label-Free Analysis," in Journal of Lightwave Technology, 2011, vol. 29, No. 13, pp. 1926-1930, doi: 10.1109/JLT.2011.2150734.

List of references Mailed on Apr. 11, 2023 for U.S. Appl. No. 17/302,535, 1 page(s).

Notice of Allowance and Fees Due (PTOL-85) dated Jul. 26, 2023 for U.S. Appl. No. 17/446,684, 3 page(s).

Notice of Allowance and Fees Due (PTOL-85) dated Jul. 27, 2023 for U.S. Appl. No. 17/446,686, 9 page(s).

Notice of Allowance and Fees Due (PTOL-85) dated Sep. 13, 2023 for U.S. Appl. No. 17/302,535, 3 page(s).

Notice of Allowance and Fees Due (PTOL-85) dated Aug. 10, 2023 for U.S. Appl. No. 17/302,535, 8 page(s).

Notice of Allowance and Fees Due (PTOL-85) dated Aug. 10, 2023 for U.S. Appl. No. 17/446,686, 3 page(s).

Notice of Allowance and Fees Due (PTOL-85) dated Aug. 31, 2023 for U.S. Appl. No. 17/446,684, 3 page(s).

Notice of Allowance and Fees Due (PTOL-85) dated Aug. 31, 2023 for U.S. Appl. No. 17/446,686, 3 page(s).

Notice of Allowance and Fees Due (PTOL-85) dated Aug. 7, 2023 for U.S. Appl. No. 17/446,684, 3 page(s).

EP Office Action dated Sep. 27, 2023 for EP Application No. 21172819, 5 page(s).

European search report dated Oct. 2, 2023 for EP Application No. 23177883, 7 page(s).

European search report dated Oct. 23, 2023 for EP Application No. 23152603, 11 page(s).

\* cited by examiner

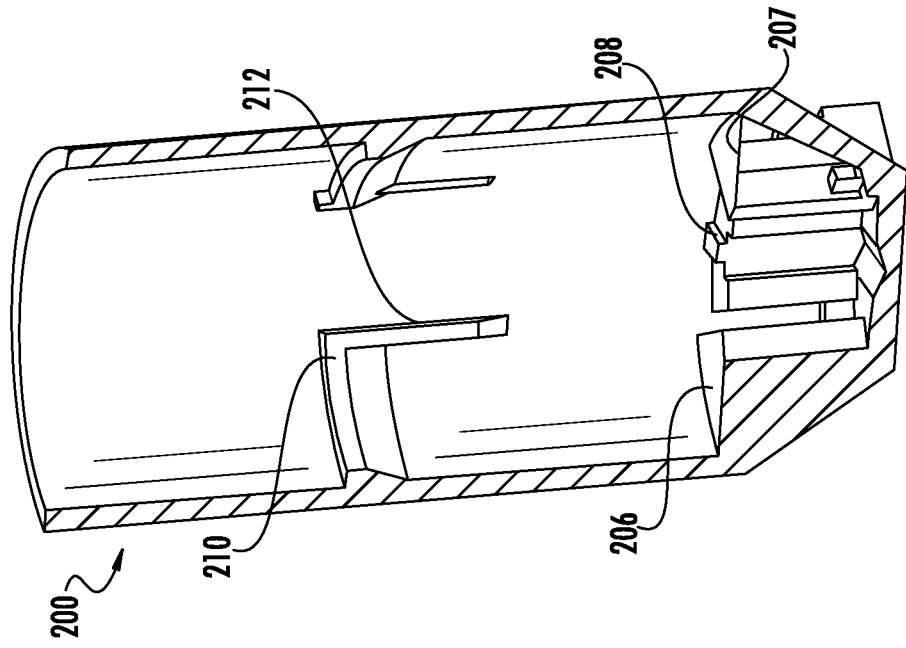
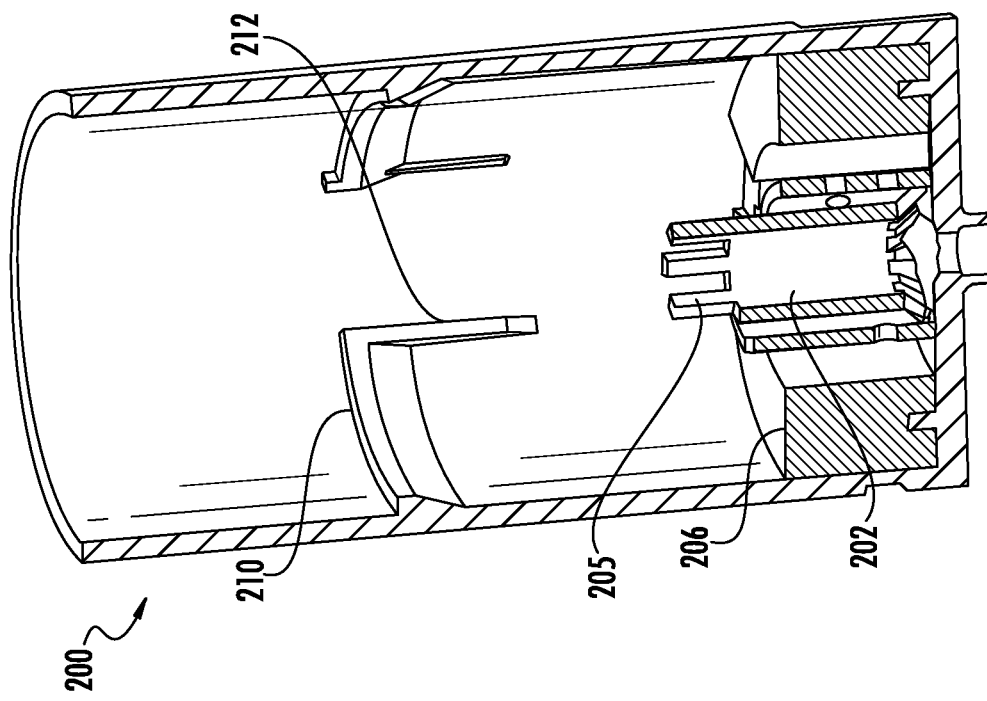

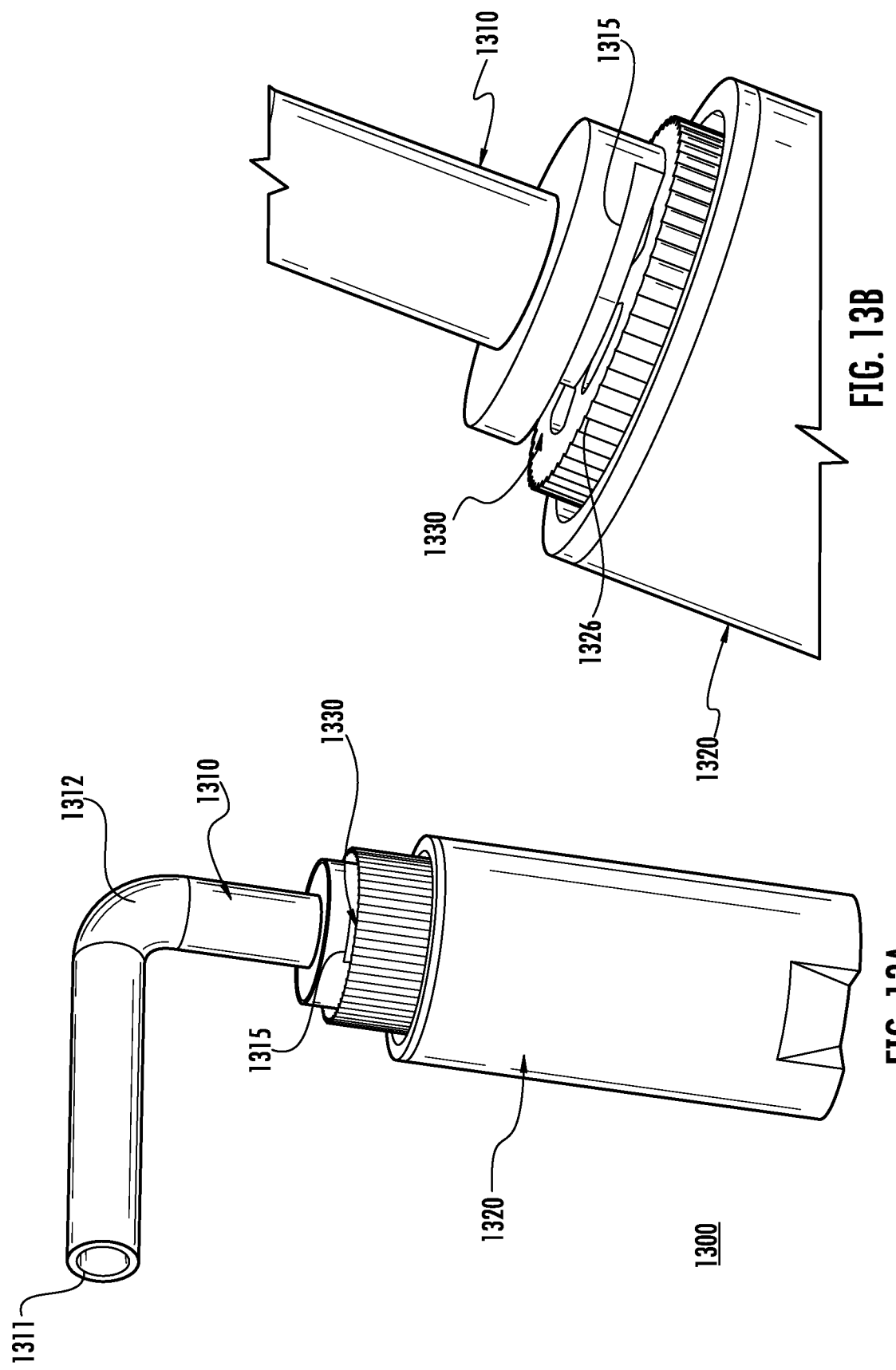

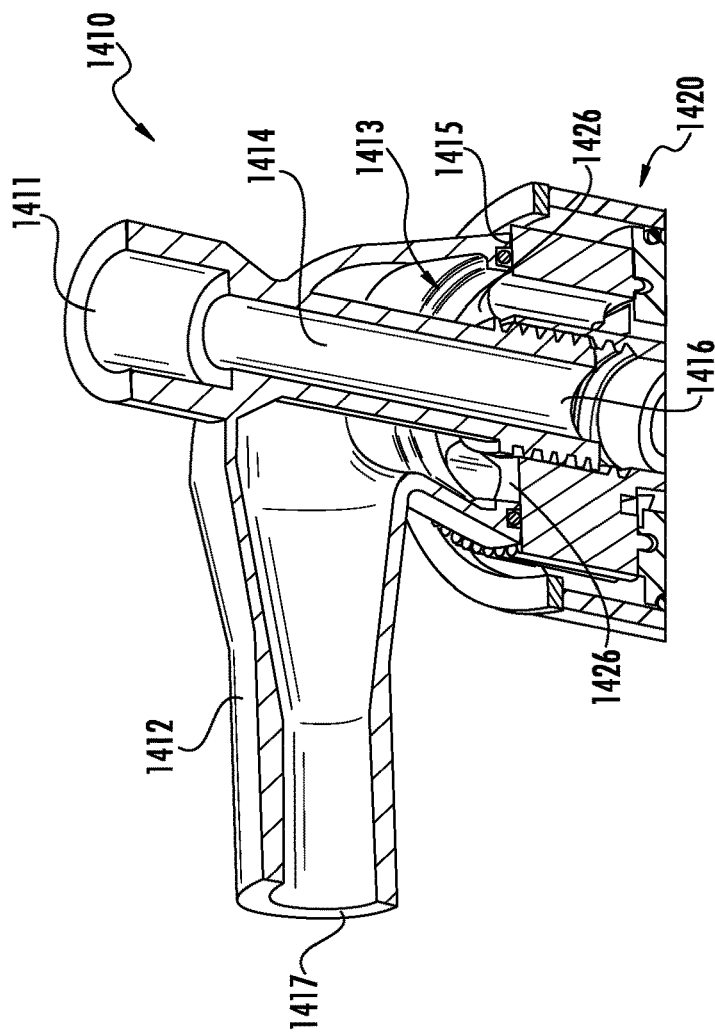
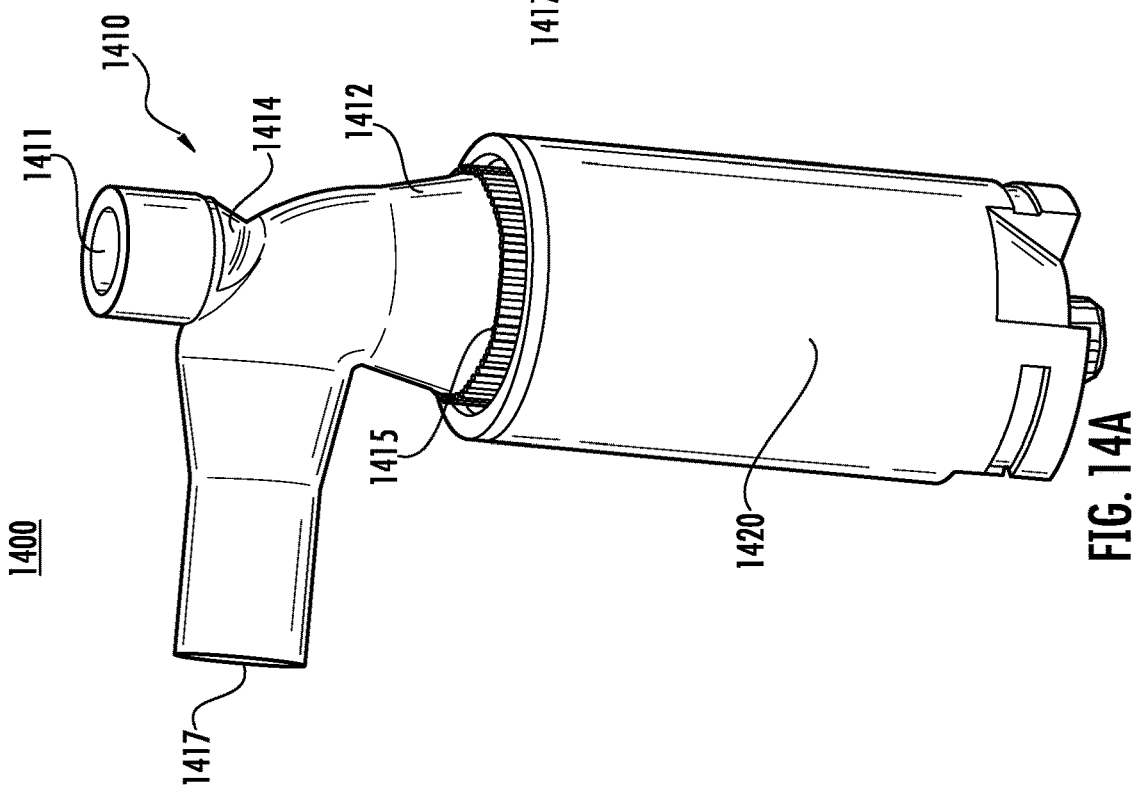
FIG. 14B
FIG. 14A

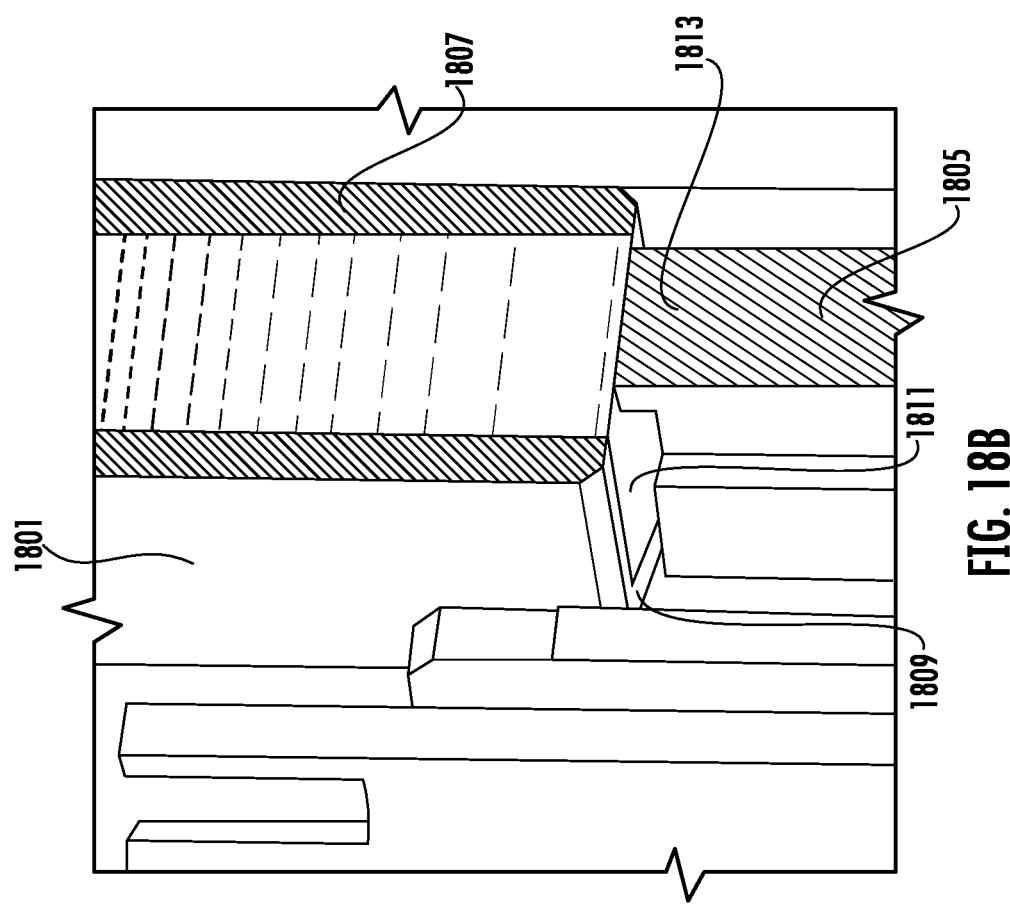
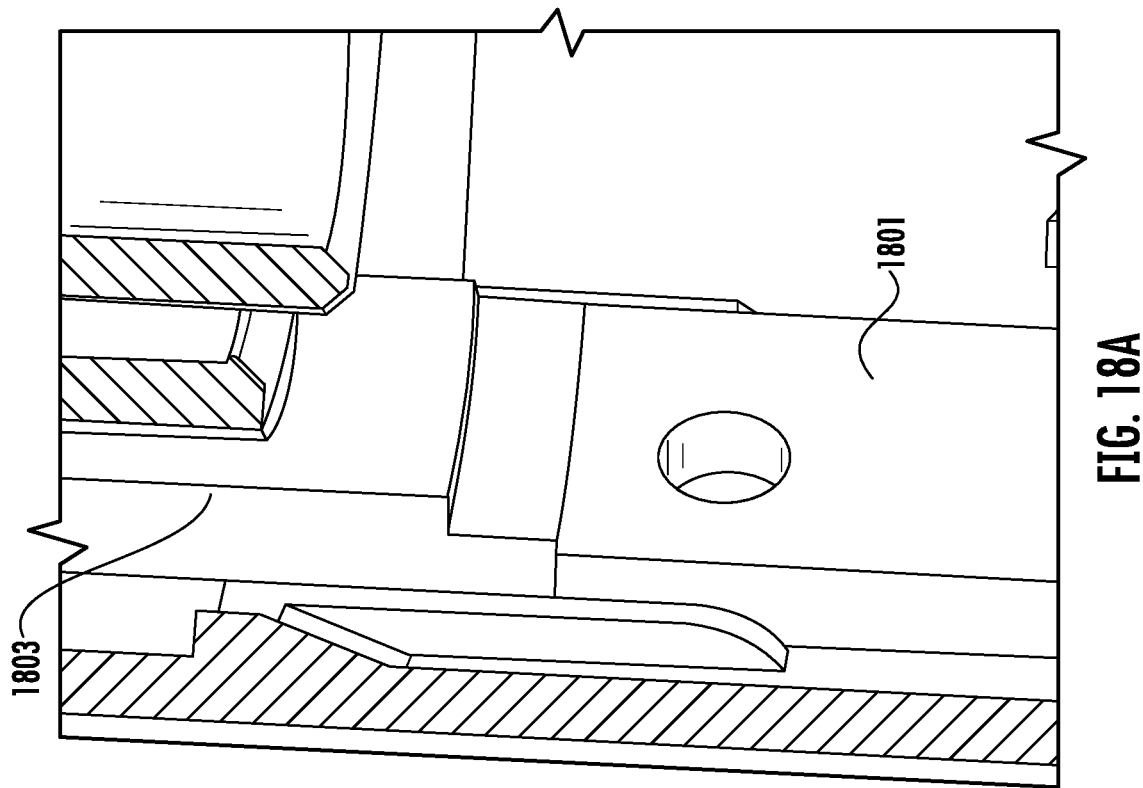
FIG. 18B
FIG. 18A

APPARATUSES, SYSTEMS, AND METHODS FOR SAMPLE CAPTURE AND EXTRACTION

CROSS-REFERENCE TO RELATED APPLICATIONS

The present application is a continuation of U.S. Non-Provisional patent application Ser. No. 17/302,535 (filed May 5, 2021), which claims priority to and benefit of U.S. Provisional Patent Application No. 63/198,609 (filed Oct. 29, 2020), and U.S. Provisional Patent Application No. 63/154,476 (filed on Feb. 26, 2021), the entire contents of which are incorporated by reference into the present application.

BACKGROUND

Existing methods, apparatuses, and systems for collecting aerosols are plagued by challenges and limitations.

For example, shelf life, efficiency and/or accuracy of these devices may be limited due to various factors such as, but not limited to, structural limitations, contamination risks, and/or the like.

BRIEF SUMMARY

In accordance with various examples of the present disclosure, various example methods, apparatuses, and systems (such as, but not limited to, an aerosol collection device) for sample capturing and extraction are provided.

In some embodiments, an aerosol collection device is provided. In some embodiments, the aerosol collection device comprises a sample transfer adapter configured to receive a sample; and a device body connected to the sample transfer adapter, wherein the device body defines a flow channel guiding the sample to a filter component, wherein the filter component contains a buffer solution.

In some embodiments, the device body comprises a vessel component having a sample distribution annulus element. In some embodiments, the buffer solution is contained in at least one of a first side of the filter component adjacent to the sample distribution annulus element or a second side of the filter component opposite to the first side.

In some embodiments, the sample transfer adapter is a sampling tunnel.

In some embodiments, the sample transfer adapter is a mask component.

In some embodiments, the aerosol collection device further comprises an extraction cartridge.

In some embodiments, the device body comprises a sample liquid extraction outlet. In some embodiments, the extraction cartridge comprises one or more puncturing elements configured to at least partially extend into the sample liquid extraction outlet.

In some embodiments, the device body comprises: a vessel component comprising at least one capsule extraction body element; at least one capsule component positioned on a top surface of the at least one capsule extraction body element; and an upper plunger component positioned on a top surface of the at least one capsule component.

In some embodiments, the at least one capsule component stores the buffer solution.

In some embodiments, each of the at least one capsule component comprises a holder element and a cap element. In some embodiments, the buffer solution is hermetically sealed in the holder element by the cap element.

In some embodiments, the at least one capsule extraction body element comprises a protrusion positioned on the top surface of the at least one capsule extraction body element. In some embodiments, the cap element is positioned on top of the protrusion.

In some embodiments, the vessel component comprises at least two vertical ridge elements disposed on an inner lateral surface of the vessel component. In some embodiments, at least a portion of each of the at least one capsule component is positioned between the at least two vertical ridge elements.

In some embodiments, in response to receiving a vertically downward force exerted on a top surface of the upper plunger component, the upper plunger component is configured to transfer the vertically downward force to the at least one capsule component and causing a vertical movement of the at least one capsule component.

In some embodiments, the vertical movement of the at least one capsule component causes the at least one capsule extraction body element to break the cap element of each of the at least one capsule component.

In some embodiments, subsequent to the cap element being broken, the buffer solution flows on the filter component.

In some embodiments, the vessel component further comprises: a sample distribution annulus element comprising a plurality of holes, and a valve support annulus element disposed within the sample distribution annulus element.

In some embodiments, the at least one capsule extraction body element is positioned radially outward from the sample distribution annulus element.

In some embodiments, the aerosol collection device further comprises: a tube component secured to the sample distribution annulus element; and a valve component supported by the valve support annulus element.

In some embodiments, the filter component is inserted between the sample distribution annulus element and the at least one capsule extraction body element. In some embodiments, the aerosol collection device further comprises a lower plunger component positioned on a top surface of the filter component.

In some embodiments, the lower plunger component comprises a plurality of plunger support wings. In some embodiments, each of the plurality of plunger support wings is positioned between two capsule components.

In some embodiments, the upper plunger component is configured to translate from a first configuration to a second configuration by a rotational force. In some embodiments, in the first configuration, a bottom surface of the upper plunger component is in contact with a top surface of each of the at least one capsule component. In some embodiments, in the second configuration, the bottom surface of the upper plunger component is in contact with a top surface of each of the plurality of plunger support wings.

In some embodiments, a vessel component having an inner bottom surface and an inner lateral surface is provided. In some embodiments, the vessel component comprises a sample distribution annulus element positioned on the inner bottom surface of the vessel component; a valve support annulus element positioned within the sample distribution annulus element; at least one filter support body element positioned on the inner bottom surface of the vessel component and radially outward from the sample distribution annulus element; and at least one capsule extraction body element positioned on the inner bottom surface of the vessel component and radially outward from the sample distribution annulus element.

In some embodiments, the at least one capsule extraction body element is positioned between the inner bottom surface of the vessel component and the inner lateral surface of the vessel component.

In some embodiments, the at least one filter support body element is positioned between the inner bottom surface of the vessel component and the inner lateral surface of the vessel component.

In some embodiments, each of the at least one capsule extraction body element is positioned between two filter support body elements.

In some embodiments, the valve support annulus element comprises a plurality of supporting beams.

In some embodiments, the vessel component further comprises at least one horizontal ridge element disposed on the inner lateral surface of the vessel component and at least one vertical ridge element disposed on the inner lateral surface of the vessel component.

In some embodiments, the at least one horizontal ridge element and the at least one vertical ridge element are connected and in an perpendicular arrangement.

In some embodiments, the at least one vertical ridge element comprises at least one vertical lock ridge element and at least one vertical stop ridge element.

In some embodiments, a tube component comprises a pipe element and a vent bluff annulus element. In some embodiments, the pipe element has a top portion and a bottom portion. In some embodiments, the top portion is connected to the bottom portion, forming at least a portion of a flow channel for receiving a sample. In some embodiments, the vent bluff annulus element surrounds the top portion of the pipe element.

In some embodiments, the vent bluff annulus element has at least one opening on a lateral surface of the vent bluff annulus element.

In some embodiments, a lower plunger component comprises a plunger annulus element having an outer lateral surface and at least one plunger support wing disposed on the outer lateral surface. In some embodiments, the at least one plunger support wing comprises a bottom portion and a lateral portion.

In some embodiments, the bottom portion of the at least one plunger support wing is in a perpendicular arrangement with the lateral portion of the at least one plunger support wing.

In some embodiments, the plunger annulus element comprises at least one plunger leg component. In some embodiments, the at least one plunger leg component extends inward to a central axis of the plunger annulus element and is in a perpendicular arrangement with an inner lateral surface of the plunger annulus element.

In some embodiments, a upper plunger component comprises a plunger body element and a plunger head element secured to the plunger body element.

In some embodiments, the plunger body element further comprises: a central annulus portion; an intermedial annulus portion; and at least one leg portion. In some embodiments, the central annulus portion is positioned within the intermedial annulus portion. In some embodiments, at least one leg portion is connected to the intermedial annulus portion and positioned radically outwards from the intermedial annulus portion.

In some embodiments, a first end of the central annulus portion is partially connected to a first end of the intermedial annulus portion, forming at least a portion of at least one vent channel between the central annulus portion and the intermedial annulus portion.

In some embodiments, a first end of the at least one leg portion is connected to the first end of the intermedial annulus portion, forming at least a portion of an annulus groove on a top surface of the plunger body element.

In some embodiments, a lateral surface of the plunger body element defines an o-ring groove.

In some embodiments, the plunger head element comprises an annulus tongue extending from a bottom surface of the plunger head element.

In some embodiments, the plunger head element defines a central bore and one or more apertures positioned radially outward from the central bore.

In some embodiments, a method for assembling an aerosol collection device comprises: providing a vessel component comprising at least a valve support annulus element and a sample distribution annulus element; inserting a filter component between the sample distribution annulus element and at least one of a filter support body element or a capsule extraction body element of the vessel component; positioning a valve component on the valve support annulus element; securing a tube component to the sample distribution annulus element; positioning at least one capsule component on a top surface of the capsule extraction body element; positioning a lower plunger component on a top surface of the filter component; and securing a upper plunger component on a top surface of the at least one capsule component.

In some embodiments, the valve support annulus element comprises a plurality of supporting beams. In some embodiments, the valve component is supported by the plurality of supporting beams.

In some embodiments, the valve component is positioned between the plurality of supporting beams of the valve support annulus element and an inner surface of a middle portion of a pipe element of the tube component.

In some embodiments, the tube component is secured to the sample distribution annulus element through a slide interference fit.

In some embodiments, the at least one capsule component is secured between at least two vertical ridge elements of the vessel component.

In some embodiments, the upper plunger component is secured to an inner lateral surface of the vessel component through an o-ring.

In some embodiments, the method further comprises securing a cap component on the upper plunger component.

In some embodiments, an aerosol collection device comprises a vessel component comprising: a sample distribution annulus element, a valve support annulus element within the sample distribution annulus element, and/or at least one capsule extraction body element positioned radially outward from the sample distribution annulus element. In some embodiments, an aerosol collection device comprises a valve component supported by the valve support annulus element; a tube component secured to the sample distribution annulus element; at least one capsule component positioned on a top surface of the at least one capsule extraction body element; and/or an upper plunger component positioned on a top surface of the at least one capsule component.

In some embodiments, the aerosol collection device comprises a filter component inserted between the sample distribution annulus element and the at least one capsule extraction body element; and a lower plunger component positioned on a top surface of the filter component. In some embodiments, the sample distribution annulus element comprises a plurality of holes.

In some embodiments, the aerosol collection device comprises a cap component secured to the upper plunger component.

In some embodiments, a method for operating an aerosol collection device comprises removing a cap component of the aerosol collection device from an upper plunger component of the aerosol collection device; connecting a sample transfer adapter to a flow channel defined by the upper plunger component and a tube component; and causing sample flow into the aerosol collection device through the flow channel, so that the sample is in contact with a buffer solution within the aerosol collection device.

In some embodiments, the aerosol collection device comprises at least one capsule component storing buffer solution. In some embodiments, connecting the sample transfer adapter to the flow channel causes a release of the buffer solution from at least one capsule component to a filter component within the aerosol collection device.

In some embodiments, the upper plunger component is positioned on a top surface of the at least one capsule component.

In some embodiments, the method comprises exerting a rotational force on the upper plunger component, causing the upper plunger component to translate from a first configuration to a second configuration. In some embodiments, in the first configuration, a bottom surface of the upper plunger component is in contact with a top surface of the at least one capsule component, and in the second configuration, the bottom surface of the upper plunger component is in contact with a top surface of a lower plunger component. In some embodiments, the method comprises exerting a vertically downward force on a top surface of the upper plunger component when the upper plunger component is in the second configuration, causing the lower plunger component to press on the filter component.

In some embodiments, the method comprises connecting a sample extraction device to the aerosol collection device to extract the buffer solution.

In some embodiments, the sample transfer adapter comprises a sampling channel configured to deliver the sample to a sample inlet of the device body.

In some embodiments, the sample transfer adapter further comprises an attachment element configured to connect the sample transfer adapter to the device body. In some embodiments, the attachment element defines at least a portion of the sampling channel.

In some embodiments, the sample transfer adapter further comprises one or more adapter ventilation elements defining at least a portion of a dispense flow path to facilitate delivery of a dispensed sample emitted from the device body to an ambient environment.

In some embodiments, the sample transfer adapter is a sampling tunnel.

In some embodiments, the sample transfer adapter is a mask component.

In some embodiments, the sample transfer adapter is at least one of a sampling tunnel or a mask component.

In some embodiments, the mask component comprises one or more facial interface elements configured to engage at least a portion of a face of a user.

In some embodiments, the sample transfer adapter is configured to engage one or more surfaces of the device body so as to provide an at least substantially air-tight seal around a sample exhaust outlet of the device body.

In some embodiments, the sample transfer adapter comprises a sampling hood component comprising a hood interior cavity configured to receive the sample from the device body via the sample exhaust outlet.

In some embodiments, the sampling hood component further comprises a sampling hood outlet fluidly connected to the hood interior cavity and defining a dispense flow path so as to facilitate a dispense of the sample from the hood interior cavity to a downstream environment fluidly connected to the sampling hood outlet.

In some embodiments, a sample transfer adapter comprises: a sample transfer adapter inlet configured to receive a sample. In some embodiments, the sample transfer adapter is configured for attachment to an aerosol collection device body comprising a filter component disposed therein for filtering the sample.

In some embodiments, the sample transfer adapter further comprises a sampling channel configured to deliver the sample to a sample inlet of the aerosol collection device body.

In some embodiments, the sample transfer adapter further comprises an attachment element configured to connect the sample transfer adapter to the aerosol collection device body. In some embodiments, the attachment element defines at least a portion of the sampling channel.

In some embodiments, the sample transfer adapter further comprises one or more adapter ventilation elements defining at least a portion of a dispense flow path to facilitate delivery of a dispensed sample emitted from the aerosol collection device body to an ambient environment.

In some embodiments, the mask component comprises one or more facial interface elements configured to engage at least a portion of a face of a user.

In some embodiments, the sample transfer adapter is further configured to engage one or more surfaces of the aerosol collection device body so as to provide an at least substantially air-tight seal around a sample exhaust outlet of the aerosol collection device body.

In some embodiments, the sample transfer adapter further comprises a sampling hood component comprising a hood interior cavity configured to receive a dispensed sample emitted from the aerosol collection device body via the sample exhaust outlet.

In some embodiments, the sampling hood component further comprises a sampling hood outlet fluidly connected to the hood interior cavity and defining a dispense flow path to facilitate delivery of the dispensed sample from the hood interior cavity to a downstream environment fluidly connected to the sampling hood outlet.

In some embodiments, an aerosol collection device comprises a capsule extraction body element, and at least one capsule component storing buffer solution and positioned on the capsule extraction body element.

In some embodiments, each of the at least one capsule component comprises a holder element and a cap element. In some embodiments, the buffer solution is hermetically sealed in the holder element by the cap element.

In some embodiments, the cap element is attached to the holder element through a chemical adhesive.

In some embodiments, the aerosol collection device comprises a vessel component having an inner lateral surface.

In some embodiments, the vessel component comprises at least two vertical ridge elements disposed on the inner lateral surface. In some embodiments, at least a portion of each of the at least one capsule component is positioned between the at least two vertical ridge elements.

In some embodiments, the vessel component comprises at least one horizontal ridge element disposed on the inner lateral surface of the aerosol collection device. In some embodiments, at least a top surface of each of the at least one capsule component is on a same plane as a top surface of the at least one horizontal ridge element.

In some embodiments, the aerosol collection device further comprises a first capsule component storing a first buffer solution and a second capsule component storing a second buffer solution.

In some embodiments, the first buffer solution is the same as the second buffer solution.

In some embodiments, the first buffer solution is different from the second buffer solution.

In some embodiments, the aerosol collection device further comprises a first capsule component, a second capsule component, and a third capsule component.

In some embodiments, the capsule extraction body element comprises a protrusion positioned on a top surface of the capsule extraction body element. In some embodiments, a cap element of the capsule component is positioned on top of the protrusion.

In some embodiments, an air gap is formed between the top surface of the capsule extraction body element and the cap element.

In some embodiments, an aerosol collection device comprises at least one capsule component storing buffer solution; and an upper plunger component in contact with a top surface of the at least one capsule component.

In some embodiments, each of the at least one capsule component comprises: a holder element defining a cavity having an opening on a bottom surface of a corresponding capsule component and storing the buffer solution, and a cap element hermetically sealing the opening of the holder element.

In some embodiments, the upper plunger component is in contact with a top surface of the holder element. In some embodiments, at least a portion of the cap element is in contact with a capsule extraction body element.

In some embodiments, in response to receiving a vertically downward force exerted on a top surface of the upper plunger component, the upper plunger component is configured to transfer the vertically downward force to the at least one capsule component and causing a vertical movement of the at least one capsule component.

In some embodiments, the vertical movement of the at least one capsule component causes the capsule extraction body element to break the cap element of each of the at least one capsule component.

In some embodiments, subsequent to the cap element being broken, the buffer solution flows on the capsule extraction body element.

In some embodiments, a filter component is positioned adjacent to the capsule extraction body element. In some embodiments, subsequent to the cap element being broken, the buffer solution flows to the filter component.

In some embodiments, a method for operating an aerosol collection device comprises exerting a vertically downward force on a top surface of an upper plunger to cause a release of buffer solution from within at least one capsule component to a filter component; and providing a sample to the filter component.

In some embodiments, an aerosol collection device comprises: an upper plunger component comprising a central annulus portion and an intermedial annulus portion. In some embodiments, the central annulus portion is disposed within the intermedial annulus portion, forming a gap between the central annulus portion and the intermedial annulus portion. In some embodiments, an aerosol collection device comprises: a tube component comprising a vent bluff annulus element. In some embodiments, at least a portion of the central annulus portion is positioned within and in contact with the vent bluff annulus element.

In some embodiments, the upper plunger component comprises a plunger head element defining a central bore. In some embodiments, the tube component comprises a pipe element connected to the central bore and forming a portion of a flow channel for receiving sample.

In some embodiments, the central annulus portion and the intermedial annulus portion define a portion of a vent channel for discharging a sample.

In some embodiments, an aerosol collection device comprises: a lower plunger component comprising a plurality of plunger support wings; and an upper plunger component configured to translate from a first configuration to a second configuration by a rotational force. In some embodiments, each of the plurality of plunger support wings is positioned between two of a plurality of capsule components. In some embodiments, in the first configuration, a bottom surface of the upper plunger component is in contact with a top surface of each of the plurality of capsule components, and in the second configuration, the bottom surface of the upper plunger component is in contact with a top surface of each of the plurality of plunger support wings.

In some embodiments, the upper plunger component comprises at least one leg portion. In some embodiments, in the first configuration, a bottom surface of the at least one leg portion is in contact with the top surface of each of the plurality of capsule components, and in the second configuration, the bottom surface of the at least one leg portion is in contact with the top surface of each of the plurality of plunger support wings.

In some embodiments, the lower plunger component and the upper plunger component are housed within a vessel component having at least one vertical lock ridge element and at least one vertical stop ridge element disposed on an inner lateral surface of the vessel component.

In some embodiments, the rotational force causes at least a portion of the at least one leg portion to rotate past the at least one vertical lock ridge element and stop at the at least one vertical stop ridge element.

In some embodiments, an aerosol collection device comprises a lower plunger component and an upper plunger component. In some embodiments, a bottom surface of the lower plunger component is in contact with a filter component. In some embodiments, an upper plunger component is in contact with a top surface of the lower plunger component.

In some embodiments, in response receiving a vertical force exerted on a top surface of the upper plunger component, the upper plunger component is configured to transfer the vertical force to the lower plunger component and causing a vertical movement of the lower plunger component when the lower plunger component is in the second configuration.

In some embodiments, the vertical movement of the lower plunger component causes the filter component to be squeezed.

In some embodiments, a method for operating an aerosol collection device comprises exerting a rotational force on an upper plunger component, causing the upper plunger component to translate from a first configuration to a second configuration. In some embodiments, in the first configuration, a bottom surface of the upper plunger component is in contact with a top surface of each of a plurality of capsule components, and in the second configuration, the bottom surface of the upper plunger component is in contact with a top surface of each of a plurality of plunger support wings of a lower plunger component. In some embodiments, the method for operating the aerosol collection device further comprises exerting a vertical force on a top surface of the upper plunger component.

In some embodiments, an aerosol collection device comprises a device body configured to receive a sample. In some embodiments, the device body comprises a filter component disposed within the interior device body portion for filtering the sample and a sample distribution annulus element fluidly connected to the filter component. In some embodiments, the sample distribution annulus element is configured to receive the sample and deliver at least a portion of the sample to one or more portions of the filter component.

In some embodiments, the sample distribution annulus element comprises one or more sample distribution elements configured to facilitate distribution of the sample throughout filter component.

In some embodiments, each of the one or more sample distribution elements is configured to distribute at least a portion of the sample to a respective filter portion of a plurality of distributed filter portions defined throughout the filter component.

In some embodiments, the filter component comprises an at least substantially cylindrical configuration defined at least in part by a substantially cylindrical interior filter. In some embodiments, the sample distribution annulus element comprises a sample distribution annulus element sidewall, and the device body is configured such that an outer surface of the sample distribution annulus element is positioned at least substantially adjacent the interior filter surface.

In some embodiments, the one or more sample distribution elements comprise a plurality of orifices extending through a sample distribution annulus element sidewall of the sample distribution annulus element, each of the plurality of orifices defining a fluid connection between the sample distribution annulus element and the filter component.

In some embodiments, the plurality of orifices is configured to facilitate an at least substantially uniform annular distribution of the sample from the sample distribution annulus element to the interior filter surface.

In some embodiments, the filter component is configured to receive the sample and capture an aerosol from the sample within the filter component.

In some embodiments, filter component is wetted by a buffer solution.

In some embodiments, the buffer solution is configured to cause the captured aerosol disposed within the filter component to be retained into an at least partially liquid state.

In some embodiments, the filter component is configured to allow a volume of air defined by an aerosol-removed portion of the sample received by the filter component to flow in an upward direction along a length of the filter component to an upper boundary of the filter component.

In some embodiments, the filter component is further configured to allow the volume of air defined by the aerosol-removed portion of the sample to emerge from the upper boundary of the filter component and into a breathalyzer chamber positioned above the filter component and configured to receive the volume of air.

In some embodiments, an aerosol collection device comprises a device body configured to receive a sample. In some embodiments, the device body comprising a housing comprising one or more exterior surfaces and defining an interior device body portion therein; a filter component disposed within the interior device body portion for filtering the sample; and an observation orifice configured so as to define a line of sight to at least a portion of the filter component. In some embodiments, the line of sight extending through at least a portion of the one or more exterior surfaces of the housing.

In some embodiments, the aerosol collection device further comprises at least one transparent element configured to cover a surface area of the observation orifice.

In some embodiments, the at least one transparent element embodies a magnifying element configured to visually magnify the at least a portion of the filter component positioned within the line of sight.

In some embodiments, the aerosol collection device further comprises a plurality of observation orifices.

In some embodiments, each of the plurality of observation orifices is configured so as to define a respective line of sight to a respective breathalyzer component disposed within the internal device body portion, each respective line of sight extending through a respective portion of the one or more exterior surfaces of the housing.

In some embodiments, each of the plurality of observation orifices is configured so as to define a respective line of sight to a respective portion of the filter component, each respective line of sight extending through a respective portion of the one or more exterior surfaces of the housing.

In some embodiments, the at least a portion of the filter component within the line of sight is positioned at least substantially adjacent to the observation orifice.

In some embodiments, an aerosol collection device comprises a device body configured to receive a sample and an extraction cartridge configured to extract a volume of sample liquid from within the device body. In some embodiments, the device body comprises a filter component disposed within the device body for capturing the sample. In some embodiments, the device body provides a volume of sample liquid therein.

In some embodiments, the volume of sample liquid comprises a buffer solution and an aerosol.

In some embodiments, the device body further comprises a sample liquid extraction outlet comprising an opening extending through a bottom surface of the device body along a central axis of the device body.

In some embodiments, the extraction cartridge comprises one or more attachment means configured for attaching the extraction cartridge to the sample liquid extraction outlet.

In some embodiments, the device body comprises a groove component disposed on a bottom surface of the device body.

In some embodiments, the groove component is configured to fluidly isolate the sample liquid extraction outlet from the volume of sample liquid within the device body.

In some embodiments, the extraction cartridge comprises one or more attachment means configured for attaching the extraction cartridge to the sample liquid extraction outlet.

In some embodiments, the extraction cartridge further comprises one or more puncturing means configured for puncturing the groove component of the device body upon an attachment of the extraction cartridge to the sample liquid extraction outlet.

In some embodiments, the extraction cartridge comprises an extraction plunger disposed within a cylindrical cartridge body of the extraction cartridge.

In some embodiments, the extraction cartridge is configured to extract the volume of sample liquid from within the device body based at least in part on a pressure differential generated by the extraction plunger.

In some embodiments, the extraction plunger is configured to generate the pressure differential based at least in part on a displacement along a central axis of the cylindrical cartridge body.

In some embodiments, a method of extracting a sample liquid from an aerosol collection device comprises providing a sample liquid within a device body; and extracting the sample liquid from the device body through a sample liquid extraction outlet comprising an opening extending through a bottom surface of the device body.

In some embodiments, the method comprises attaching an extraction cartridge to the sample liquid extraction outlet via one or more attachment means defined at least in part by the extraction cartridge.

In some embodiments, attaching the extraction cartridge to the sample liquid extraction outlet comprises puncturing a groove component disposed about a bottom surface of the device body upon an attachment of the extraction cartridge to the sample liquid extraction outlet.

In some embodiments, puncturing the groove component disposed about the bottom surface of the device body generates a fluid communication path between the device body and the extraction cartridge attached thereto.

In some embodiments, the method further comprises generating a pressure differential between the device body and an extraction cartridge that is connected to the sample liquid extraction outlet. In some embodiments, the sample liquid is extracted from within the device body by the extraction cartridge based at least in part on the generated pressure differential.

In some embodiments, the method further comprises receiving the sample liquid extracted from the device body at an extraction cartridge connected to the sample liquid extraction outlet; determining that the extraction cartridge has received the maximum volume of sample liquid that can be received by the extraction cartridge; generating an alert signal indicating that the extraction cartridge has reached the sample liquid volumetric capacity. In some embodiments, the extraction cartridge is defined at least in part by a sample liquid volumetric capacity corresponding to a maximum volume of sample liquid that can be received by the extraction cartridge.

In some embodiments, the method further comprises disconnecting the extraction cartridge from the sample liquid extraction outlet of the device.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative examples may be read in conjunction with the accompanying figures. It will be appreciated that, for simplicity and clarity of illustration, components and elements illustrated in the figures have not necessarily been drawn to scale, unless described otherwise. For example, the dimensions of some of the components or elements may be exaggerated relative to other elements, unless described otherwise. Examples incorporating teachings of the present disclosure are shown and described with respect to the figures presented herein, in which:

FIG. 2A, FIG. 2B, FIG. 2C, and FIG. 2D, illustrate example views of an example vessel component in accordance with examples of the present disclosure;

FIG. 13A and FIG. 13B illustrate example views of an example sample transfer adapter in accordance with various examples of the present disclosure;

FIG. 14A and FIG. 14B illustrate example views of an example sample transfer adapter in accordance with various examples of the present disclosure;

FIG. 18A and FIG. 18B each illustrates an example view of at least a portion of an example capsule component and/or a portion of an example upper plunger component in accordance with example embodiments of the present disclosure;

DETAILED DESCRIPTION OF THE INVENTION

Figure 1A:
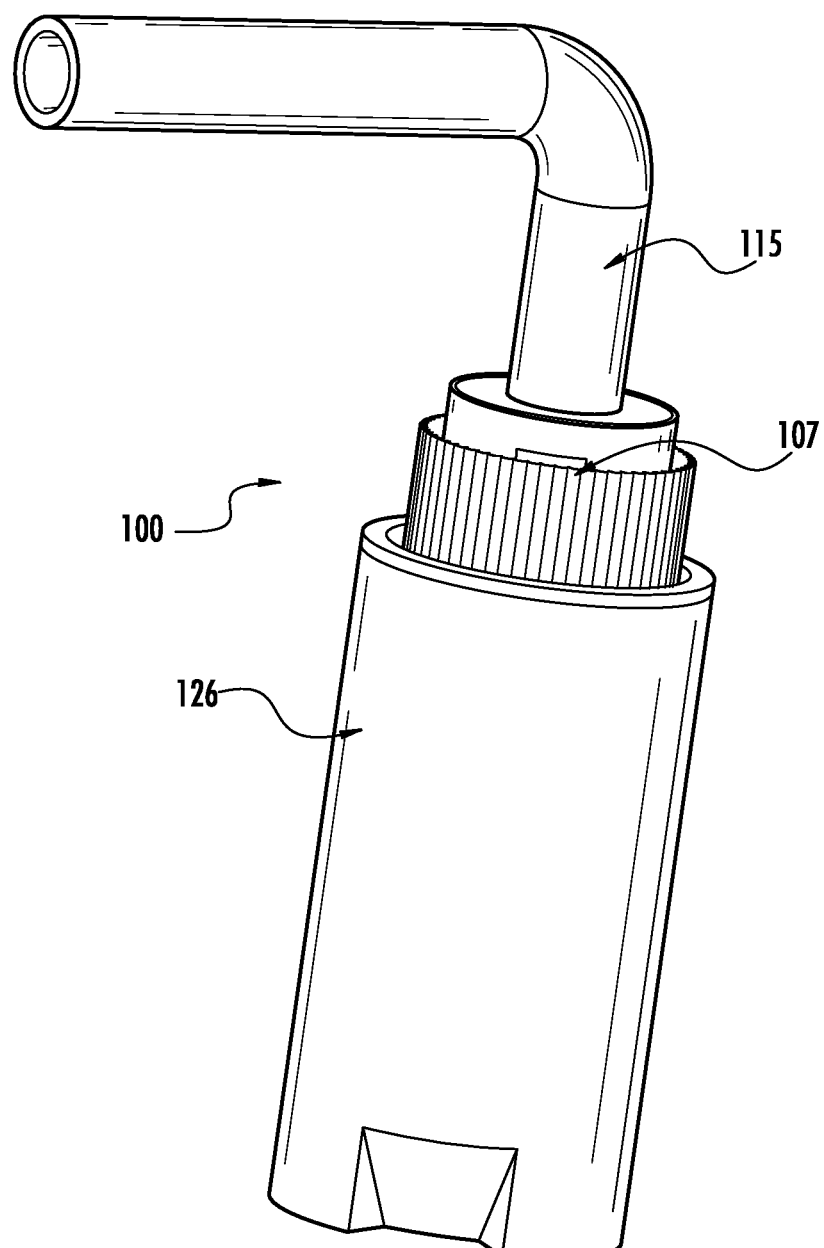
FIG. 1A illustrates an example view of an example aerosol collection device in accordance with various examples of the present disclosure.

Some examples of the present disclosure will now be described more fully hereinafter with reference to the accompanying drawings, in which some, but not all examples of the disclosure are shown. Indeed, these disclosures may be embodied in many different forms and should not be construed as limited to the examples set forth herein; rather, these examples are provided so that this disclosure will satisfy applicable legal requirements. Like numbers refer to like elements throughout.

The phrases "in one example," "according to one example," "in some examples," and the like generally mean that the particular feature, structure, or characteristic following the phrase may be included in at least one example of the present disclosure and may be included in more than one example of the present disclosure (importantly, such phrases do not necessarily refer to the same example).

If the specification states a component or feature "may," "can," "could," "should," "would," "preferably," "possibly," "typically," "optionally," "for example," "as an example," "in some examples," "often," or "might" (or other such language) be included or have a characteristic, that specific component or feature is not required to be included or to have the characteristic. Such component or feature may be optionally included in some examples, or it may be excluded.

The word "example" or "exemplary" is used herein to mean "serving as an example, instance, or illustration." Any implementation described herein as "exemplary" is not necessarily to be construed as preferred or advantageous over other implementations.

Sampling and capturing of biological aerosol particles can be an important subject in both research and commercial endeavors. This may include the detection of contagion within the sampled aerosol to accurately and quickly detect contagions. Many, if not all, upper respiratory illnesses will result in some of the disease-causing pathogens to be in the exhaled aerosols from a patient while the patient is contagious. Examples of pathogen particles include, but not limited to, bacteria, viruses, and mold/fungal spores.

However, many aerosol samplers are not applicable for direct sampling of exhaled breath. For example, many aerosol samplers may require large pressure drop, pumps, electrostatic fields, among other items, which may inhibit the free breathing of the patient or otherwise dilute the exhaled aerosols with large amounts of ambient air. In addition, processes associated with these aerosol samplers tend to damage the pathogens within the aerosols, which may adversely impact the ability to detect the collected pathogens.

In accordance with various embodiments of the present disclosure, an aerosol collection device for capturing pathogen particle(s) from aerosols in the exhaled breath is provided. In some embodiments, the aerosol collection device may comprise one or more hermetically sealed capsule components that may store a liquid solution, including, but not limited to, a buffer solution. For example, the sealed capsule components may store a buffer solution in the form of an aqueous solution that can resist pH change when an acidic or a base (for example, from a sample) is added to the buffer solution. For example, a buffer solution may comprise a mixture of weak acid and its conjugate base, or vice versa. In some embodiments, a buffer solution may provide a medium for preserving bioaerosols.

In some embodiments, the buffer solution can contain positive and negative control molecules, including, but not limited to, positive and negative control proteins. In some embodiments, the positive and negative control molecules may be selected based on the need for subsequent diagnostic.

While the description herein uses buffer solution as an example for liquid solution, it is noted that the scope of the present disclosure is not limited to the buffer solution. In some examples, various embodiments of the present disclosure may use other types of liquid solution in addition to or in alternative of a buffer solution.

In some embodiments, the aerosol collection device may feature a sequence of mechanical features to increase the fidelity of the sample capture. In some embodiments, the aerosol collection device may implement an immersed bubbler mechanism that includes a flow channel guiding exhaled breath to a buffer solution that is absorbed by a filter component for collecting aerosols from the exhaled breath, where one or more bubbles are formed in the buffer solution and aerosols from exhaled breath are captured by the filter component and/or buffer solution, details of which are described herein.

As such, an example aerosol collection device in accordance with example embodiments of the present disclosure may address various technical challenges associated with many aerosol samplers and sampling methods to provide for accurate and quick subsequent detections of contagions from a sample (such as breath). For example, an example aerosol collection device may provide an effective means for capturing aerosols in a sample, which can be further provided to downstream diagnostics for pathogen detection. Additionally, or alternatively, an example aerosol collection device may provide low pressure drop for user comfort and eliminate the need for a pump.

Figure 1B:
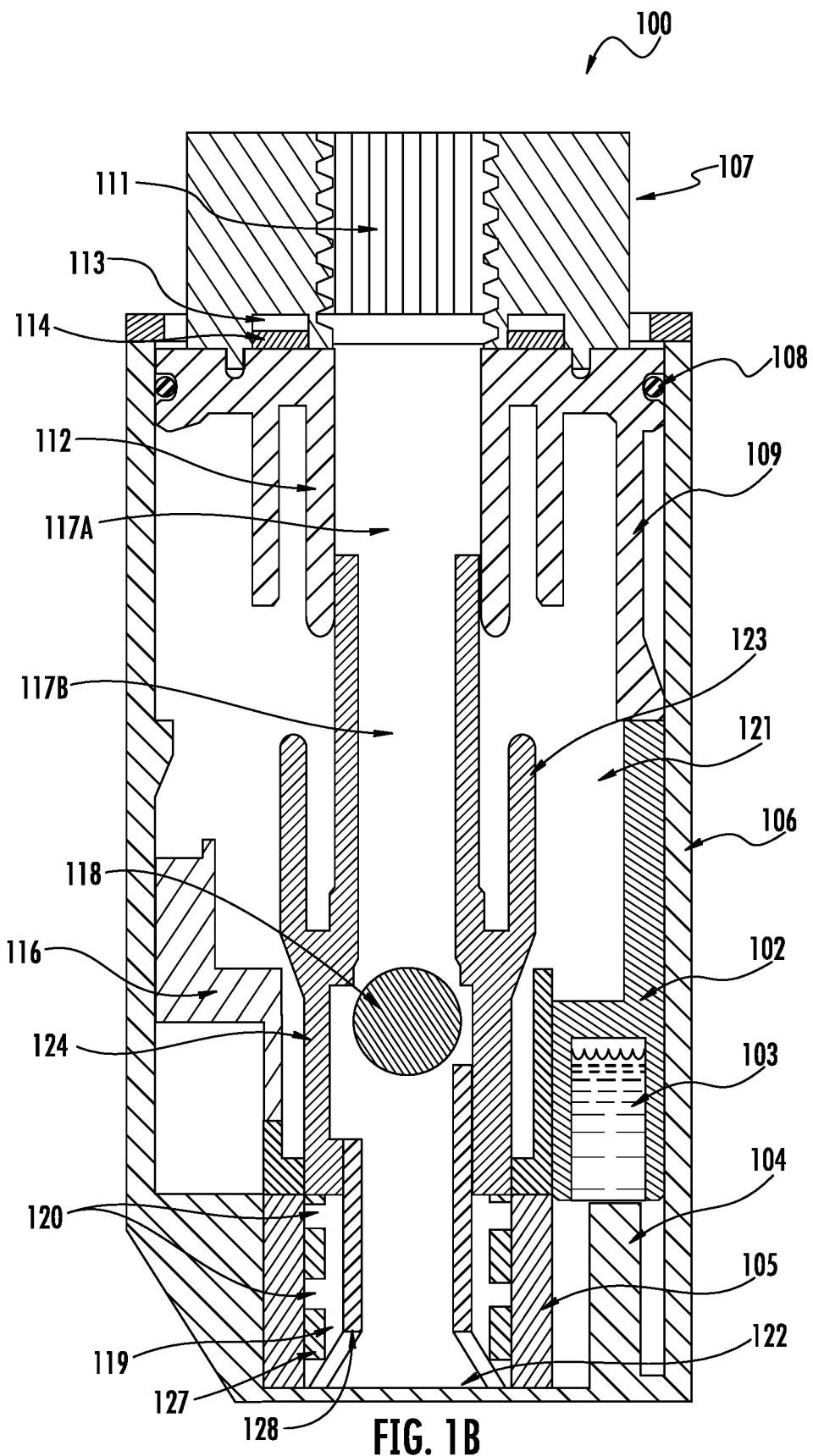
FIG. 1B illustrates an example view of an example aerosol collection device in accordance with various examples of the present disclosure.
Figure 1C:
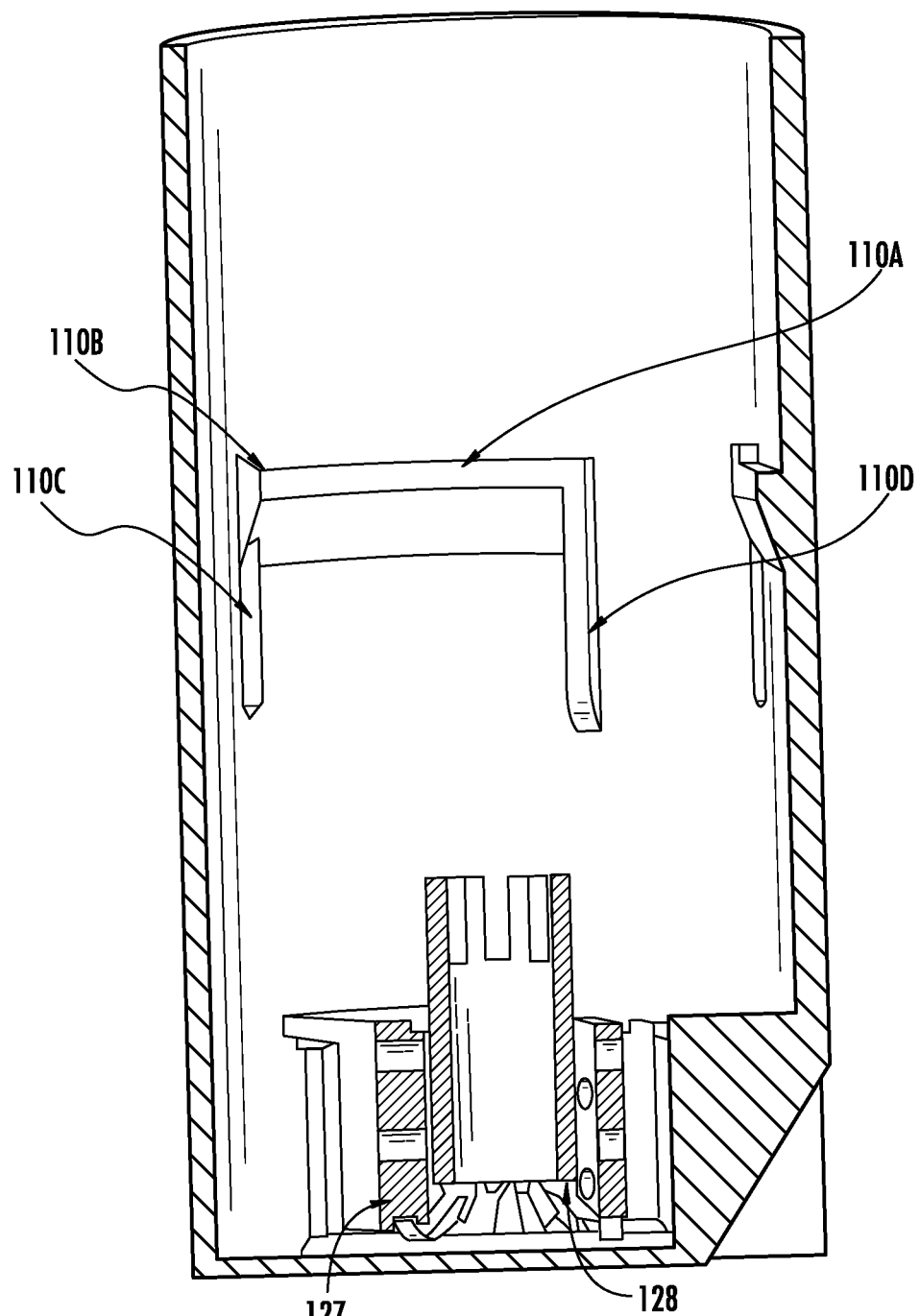
FIG. 1C illustrates an example view of an example aerosol collection device in accordance with various examples of the present disclosure.

Referring now to FIG. 1A, FIG. 1B, and FIG. 1C, an example aerosol collection device 100 in accordance with example embodiments of the present disclosure is illustrated.

Referring now to FIG. 1A, an example view of the example aerosol collection device 100 is illustrated. In the example shown in FIG. 1A, the example aerosol collection device 100 may comprise a sample transfer adapter 115 and a device body 126 (including an upper plunger component 107).

In some embodiments, the sample transfer adapter 115 may be in the form of a tubular structure that may provide a sampling tunnel. For example, the sample transfer adapter 115 may comprise a hollow portion in the center that allows air to pass. In some embodiments, the sample transfer adapter 115 may be embodied such as, but not limited to, a breathing straw. Additional embodiments of the sample transfer adapter 115 are described herein. Sample (for example, breath from a user) may be administered into the example aerosol collection device 100 via the sample transfer adapter 115. In some embodiments, the sample may comprise air and aerosol(s) (which may contain pathogen particles).

While the description above provides an example of the sample transfer adapter 115, it is noted that the scope of the present disclosure is not limited to the description above. In some examples, the sample transfer adapter 115 may be embodied such as, but not limited to, mask and/or other device(s). Additional details of example embodiments are illustrated and described herein, including but not limited to, those described in connection with at least FIG. 8 to FIG. 14B.

In some embodiments, the sample transfer adapter 115 may be attached to the upper plunger component 107 and/or the device body 126 via various means, including but not limited to, mechanical means (for example, the sample transfer adapter 115 may be screwed into device body 126), chemical means (such as chemical glues), and/or the like.

Referring now to FIG. 1B, a portion of an example cross-sectional view of the example aerosol collection device 100 is illustrated.

In the example shown in FIG. 1B, the upper plunger component 107 may define an orifice 111 positioned along the central axis of the upper plunger component 107. In some embodiments, the orifice 111 may allow for a sample (such as, but not limited to, breath from a user) to pass into the example aerosol collection device 100. For example, a user may exhale into the sample transfer adapter 115, and the breath (also referred to as the sample) may pass through the sample transfer adapter 115 and the orifice 111, and received by the example aerosol collection device 100.

In some embodiments, the sample may pass down a central passageway 117A that is connected to a central passageway 117B and to a bottom portion of the example aerosol collection device 100. In some embodiments, the central passageway 117A and the central passageway 117B define at least part of a flow channel, details of which are described herein. In some embodiments, the example aerosol collection device 100 may comprise a valve component 118 disposed along the central passageway 117B. The valve component 118 may prevent sample from being extracted out of the example aerosol collection device 100 through the central passageway 117A and the central passageway 117B. For example, when a user accidentally sucks air from the example aerosol collection device 100 through the sample transfer adapter 115, the valve component 118 may prevent the user from sucking a buffer solution from the example aerosol collection device 100 (details of which are described herein).

Referring back to FIG. 1B, subsequent to passing through the valve component 118, the sample may then be passed into an open annulus 119 at a bottom portion of the example aerosol collection device 100. In some embodiments, the open annulus 119 may be defined as the radial gap between a sample distribution annulus element 127 and the exterior of a valve support annulus element 128, details of which are described herein.

In some embodiments, the example aerosol collection device 100 may comprise one or more capsule components 102 positioned adjacent to the filter component 105. In some embodiments, the one or more capsule components 102 may be hermetically sealed. In some embodiments, the one or more capsule components 102 may store a buffer solution 103 that contains positive control molecules and/or negative control molecules based on the target pathogen particles to be detected, which allows for subsequent virus detection schemes to be more accurate. For example, in the event that the target pathogen particles are present, the positive and negative control molecules may allow for more accurate quantification of the target pathogen particles. In some embodiments, the positive and negative control molecules may provide an internal standard that can be detected by downstream diagnostic, which provides better assessment of any unknown concentration of the targeted pathogen.

In some embodiments, the capsule components 102 may be positioned in the vessel component 106 of the example aerosol collection device 100 such that the capsule components 102 may not be moved radially or circumferentially, and can only be moved vertically downwards into an capsule extraction body 104. In some embodiments, the capsule components 102 may be positioned mechanically above the capsule extraction body 104. In the example shown in FIG. 1B, the capsule extraction body 104 may be in the form of or comprise a protrusion from a bottom surface of the example aerosol collection device 100. As such, the capsule extraction body 104 may be configured to, for example, break the seal and allow the buffer solution 103 to be absorbed by the filter component 105. In some embodiments, the buffer solution 103 is contained in at least one of a first side of the filter component 105 adjacent to the sample distribution annulus element 127 (e.g. an upstream side) and/or a second side of the filter component 105 opposite to the first side (e.g. a downstream side).

In the example shown in FIG. 1B, the upper plunger component 107 may contain an o-ring 108 that may seal the upper plunger component 107 inside the example aerosol collection device 100. The upper plunger component 107 may include a series of leg portions 109 that engage the capsule components 102. When the sample transfer adapter 115 is being connected to the device body 126, a vertical force is exerted by the sample transfer adapter 115 onto a top surface of the upper plunger component 107, and the force is in turn transferred to the one or more capsule components 102 (for example, through the leg portion 109 of the upper plunger component 107), causing the capsule extraction body 104 to puncture the one or more capsule components 102 and break the seal of the capsule components 102 to release the buffer solution 103 to a filter component 105. In some embodiments, in addition to being absorbed by the filter component 105, the buffer solution may also fill the internal volume under the valve component 118. In some embodiments, the buffer solution may additionally fill a lower portion of a breathalyzer chamber 121. As such, various embodiments of the present disclosure provides a methodology to ensure correct usage of the example aerosol collection device 100.

In some embodiments, the buffer solution 103 may wet the filter component 105, and aerosols from the sample may be captured in the buffer solution 103 and/or the wetted-filter component 105 when the filter component 105 is wetted with the buffer solution 103. In some embodiments, the wetted filter component 105 may capture pathogen aerosols from breath. For example, when the aerosols contact the buffer solution 103, pathogen particles present in the aerosol may enter into the buffer solution liquid medium, therefore increasing the capture efficiency of the aerosols from the samples. In the present disclosure, the buffer solution liquid medium containing areoles (such as, but not limited to, pathogen particles) may also be referred to as a sample liquid.

In some embodiments, a plurality of holes (for example, the plurality of holes 120) of the sample distribution annulus element 127 may be positioned against the filter component 105. In some embodiments, the plurality of holes 120 may help distributing the sample equally against the filter component 105 after the buffer solution 103 from the capsule component 102 has been released to the filter component 105.

In some embodiments, the buffer solution 103 containing the pathogen particles from the aerosols may be extracted from the example aerosol collection device 100. For example, subsequent to the sample being taken (for example, after a user breathing into sample transfer adapter 115), the sample transfer adapter 115 may be disconnected from the device body 126. For example, the sample transfer adapter 115 may be unscrewed from the upper plunger component 107 and/or the device body 126. In some embodiments, after the sample transfer adapter 115 is unscrewed from the upper plunger component 107, a rotational force may be exerted on the upper plunger component 640 to rotate the upper plunger component 640.

In some embodiments, the motion of the upper plunger component 107 may be controlled by the engagement of the leg portions 109 with a set of ridge elements 110A, 110B, 110C, and 110D, which are disposed on and protruding from an inner lateral surface of the vessel component 106 of the example aerosol collection device 100 as shown in FIG. 1C. For example, the upper plunger component 640 may be rotated to pass one or more vertical lock ridge elements 110C (in some embodiments, each of the one or more vertical lock ridge elements 110C is in a triangular prism shape), and may be stopped by one or more vertical stop ridge elements 110D (in some embodiments, each of the one or more vertical stop ridge elements 110D is in a rectangular prism shape). These two sets of ridge elements 110C and 110D may lock the upper plunger component 107 into a horizontally secured position, where the leg portion 109 of the upper plunger component 107 engages with a lower plunger component 116, which in turn engages with the filter component 105. In some embodiments, a vertical force is applied on the upper plunger component 107 (e.g. the upper plunger component 107 is pressed down). After the upper plunger component 107 is pressed down, the leg portion 109 of the upper plunger component 107 engage with the lower plunger component 116 to squeeze the sample liquid from the filter component 105 and onto bottom surface of the example aerosol collection device 100.

In some embodiments, the example aerosol collection device 100 may comprise a touchless-based mechanism to extract the sample liquid from the filter component 105. For example, the example aerosol collection device 100 may comprise a groove component 122 disposed on the bottom surface of the device body of the example aerosol collection device 100. The groove component 122 may be punctured, opening up an area for the sample to be extracted, details of which are described herein.

In some embodiments, aerosols from the sample may be captured in the buffer solution 103 and/or the filter component 105, and air may be separated from the aerosols in the form of bubbles as the sample travels through the buffer solution 103 and/or the filter component 105.

In some embodiments, the upper plunger component 107 may be pressed down against the lower plunger component 116, and the lower plunger component 116 may force the sample liquid containing aerosols out of the filter component 105, creating a pressure difference that is caused by the reduction of volume inside the example aerosol collection device 100. In some embodiments, the pressure difference may cause the sample liquid to be pushed out of the groove component 122 that has been opened.

In some embodiments, after the upper plunger component 107 is pressed down, the air may then enter into a vent channel that includes the breathalyzer chamber 121. In the example shown in FIG. 1B, a portion of the breathalyzer chamber 121 is located above the filter component 105, thus enabling the air to escape from the filter component 105 after a vertical force is exerted on the filter component 105, details of which are described herein.

In some embodiments, the air may pass through a gap within the plunger body element 112 of the upper plunger component 107 and may then exit the example aerosol collection device 100 via a set of holes within upper plunger component 107, details of which are described herein. In some embodiments, the example aerosol collection device 100 may contain a filter element 114 that prevents aerosols (for example, disease-causing pathogens in the sample) from escaping from the example aerosol collection device 100. For example, a tube component 124 having a vent bluff annulus element 123 that defines part of the central passageway body may engage the plunger body element 112 of the upper plunger component 107 so that the air that escapes through the vent channel must go through the filter element 114 before exits through the opening 113, details of which are described herein.

Accordingly, an example aerosol collection device in accordance with example embodiments of the present disclosure may provide effective means for sampling biological aerosol particles.

Figures 2A, 2B:
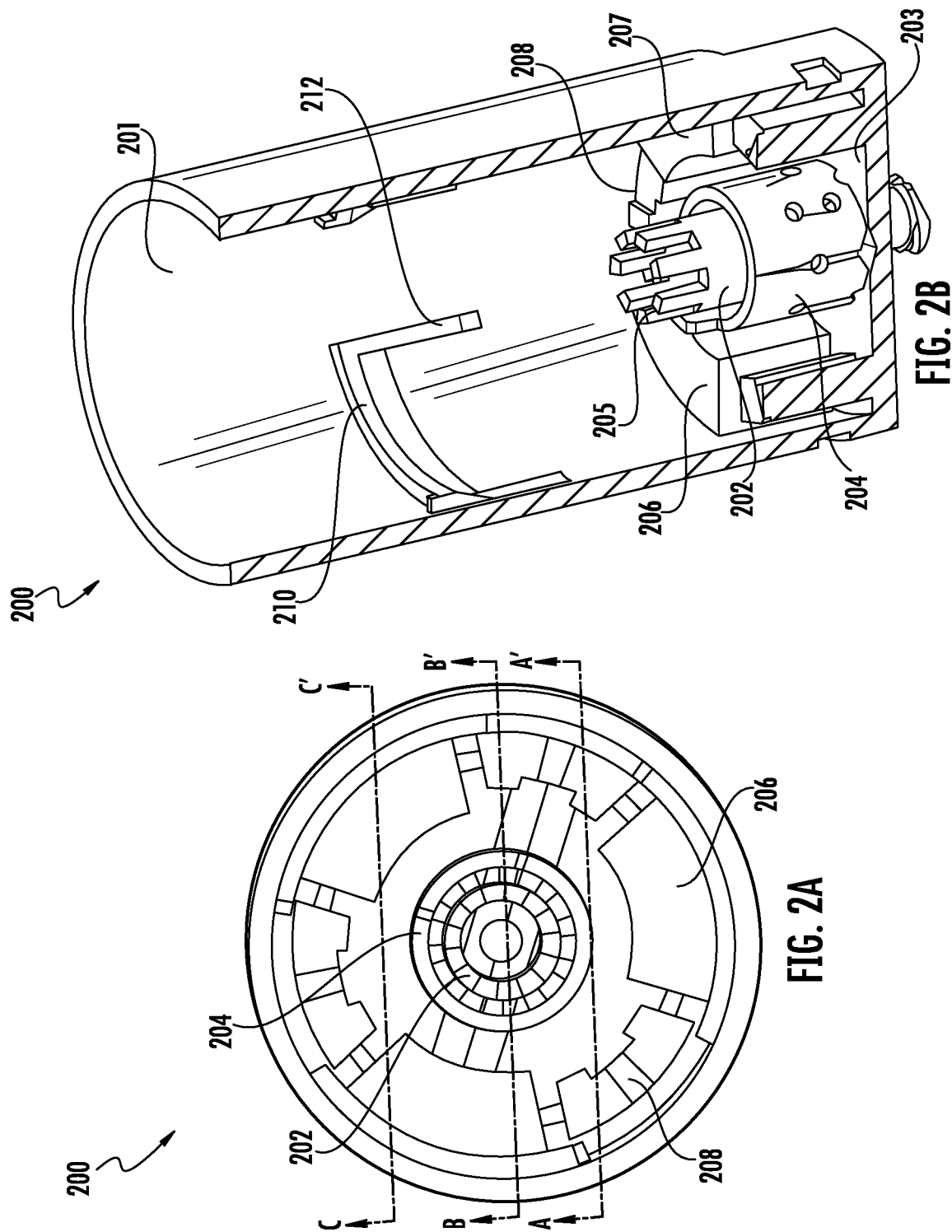
Figure 3B:
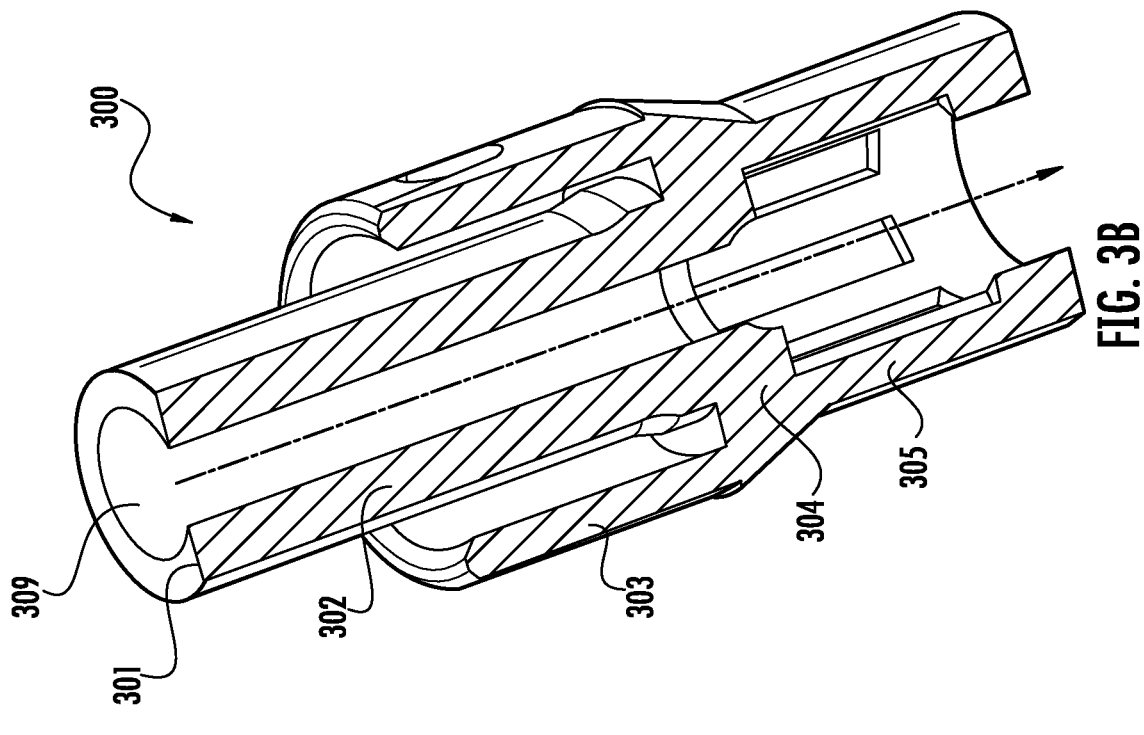
FIG. 3A and FIG. 3B illustrate example views of an example tube component in accordance with examples of the present disclosure.
Figure 3A:
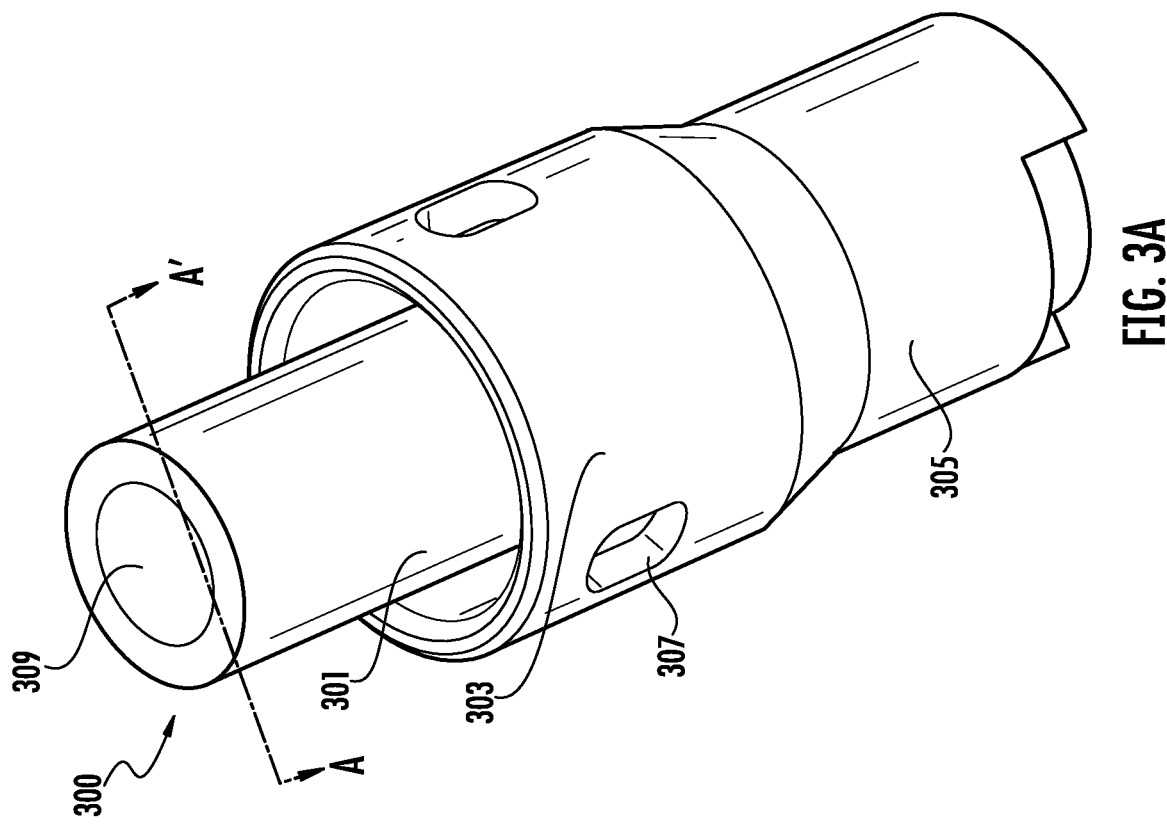

In accordance with various example embodiments of the present disclosure, an example device body of an aerosol collection device may comprise various components, including, but not limited to, a vessel component (examples of which are shown in FIG. 2A to FIG. 2D), a tube component (examples of which are shown in FIG. 3A to FIG. 3B), a lower plunger component (examples of which are shown in FIG. 4A to FIG. 5B), an upper plunger component (examples of which are shown in FIG. 5A to FIG. 5G), a cap component, a filter component, a valve component, and/or the like. In the present disclosure, the term "component" refers to a physical portion or part of an aerosol collection device. In some embodiments, each component of the aerosol collection device may be replaceable. In some embodiments, each component may comprise one or more "elements," which are parts or portions of a component.

FIG. 2A, FIG. 2B, FIG. 2C, and FIG. 2D illustrate example views of an example vessel component 200 in accordance with examples of the present disclosure. In particular, FIG. 2A illustrates an example top view of the example vessel component 200. FIG. 2B illustrates an example cross-sectional view from the cut line A-A' and viewing in the direction as shown in the arrows in FIG. 2A. FIG. 2C illustrates an example cross-sectional view from the cut line B-B' and viewing in the direction as shown in the arrows in FIG. 2A. FIG. 2D illustrates an example cross-sectional view from the cut line C-C' and viewing in the direction as shown in the arrows in FIG. 2A.

In the examples show in FIG. 2A, FIG. 2B, FIG. 2C, and FIG. 2D, the vessel component 200 is in a shape similar to a cylindrical shape. While these figures provide an example of a vessel component, it is noted that the scope of the present disclosure is not limited to these figures. In some examples, an example vessel component may be in a shape similar to other shape(s).

Referring to FIG. 2A and FIG. 2B, the vessel component 200 has an inner bottom surface 203 and an inner lateral surface 201. In some embodiments, the inner bottom surface 203 corresponds to an inner bottom surface of a cylindrical shape. In some embodiments, the inner lateral surface corresponds to an inner lateral surface of the cylindrical shape. In some embodiments, the inner bottom surface 203 is in an orthogonal or perpendicular arrangement with the inner lateral surface 201.

As shown in FIG. 2A and FIG. 2B, in some embodiments, the vessel component comprises a sample distribution annulus element 204. In some embodiments, the sample distribution annulus element 204 is positioned on the inner bottom surface 203 of the example vessel component 200.

In the examples show in FIG. 2A and FIG. 2B, the sample distribution annulus element 204 is in a shape similar to a ring shape or a tube shape. While these figures provide an example of a sample distribution annulus element, it is noted that the scope of the present disclosure is not limited to these figures. In some examples, an example sample distribution annulus element may be in a shape similar to other shape(s).

In some embodiments, the sample distribution annulus element 204 may comprise or define one or more holes, openings or apertures on the surface of the sample distribution annulus element 204. In some embodiments, one or more bubbles containing a sample may flow through one or more holes, openings, or apertures, details of which are described herein. In some embodiments, a sample may flow through the one or more holes, openings or apertures, forming one or more bubbles, details of which are described herein.

Referring back to the examples shown in FIG. 2A and FIG. 2B, the example vessel component 200 comprises an example valve support annulus element 202. In some embodiments, the example valve support annulus element 202 is positioned within the sample distribution annulus element 204. In some embodiments, the example valve support annulus element 202 is connected to the sample distribution annulus element 204 through one or more legs on the bottom surface that form one or more outlets, details of which are described herein.

In some embodiments, the valve support annulus element 202 is in a shape similar to a ring shape or a tube shape. While these figures provide an example of a valve support annulus element, it is noted that the scope of the present disclosure is not limited to these figures. In some examples, an example sample distribution annulus element may be in a shape similar to other shape(s).

In the examples shown in FIG. 2B and FIG. 2C, the valve support annulus element 202 comprises a plurality of supporting beams 205. In some embodiments, each of the plurality of supporting beams 205 extends from a top surface of the valve support annulus element 202. In some embodiments, a height of the example valve support annulus element 202 is larger than a height of the example sample distribution annulus element 204. For example, the plurality of supporting beams 205 are extended from the top surface of the valve support annulus element 202 such that they are not obscured by the sample distribution annulus element 204.

Referring back to the examples shown in FIG. 2A and FIG. 2B, the example vessel component 200 comprises at least one filter support body element (for example, filter support body element 206 and filter support body element 207). In some embodiments, the at least one filter support body element (for example, filter support body element 206 and filter support body element 207) is positioned on the inner bottom surface 203 of the vessel component 200 and positioned radially outward from the sample distribution annulus element 204.

In some embodiments, each of the at least one filter support body element (for example, each of the filter support body element 206 and the filter support body element 207) is positioned between the inner bottom surface 203 of the vessel component 200 and the inner lateral surface 201 of the vessel component 200.

Referring back to the examples shown in FIG. 2A and FIG. 2B, the example vessel component 200 comprises at least one capsule extraction body element (for example, capsule extraction body element 208). In some embodiments, the at least one capsule extraction body element (for example, capsule extraction body element 208) is positioned on the inner bottom surface 203 of the vessel component 200 and positioned radially outward from the sample distribution annulus element 204.

In some embodiments, the at least one capsule extraction body element (for example, capsule extraction body element 208) is positioned between the inner bottom surface 203 of the vessel component 200 and the inner lateral surface 201 of the vessel component 200.

In some embodiments, each of the at least one capsule extraction body element is positioned between two filter support body elements. For example, as shown in at least FIG. 2D, the capsule extraction body element 208 is positioned between the filter support body element 206 and the filter support body element 207. In some embodiments, each of the at least one filter support body element is positioned between two capsule extraction body elements.

Referring to FIG. 2B, FIG. 2C, and FIG. 2D, in some embodiments, the example vessel component 200 comprises at least one horizontal ridge element (for example, a horizontal ridge element 210) disposed on the inner lateral surface 201 of the vessel component 200. In some embodiments, the example vessel component 200 comprises at least one vertical ridge element (for example, a vertical ridge element 212) disposed on the inner lateral surface 201 of the vessel component 200.

In some embodiments, the at least one horizontal ridge element and the at least one vertical ridge element are connected and in an perpendicular arrangement with one another. For example, the horizontal ridge element 210 and the vertical ridge element 212 are connected to one another and in an perpendicular arrangement (or an orthogonal arrangement) with one another.

In some embodiments, the at least one vertical ridge element comprises one or more types of ridge elements. For example, the at least one vertical ridge element may comprise at least one vertical lock ridge element, which comprises a slope surface extending from the inner lateral surface 201. Additionally, or alternatively, the at least one vertical ridge element may comprise at least one vertical stop ridge element, which comprises a ridge surface extending from the inner lateral surface 201 (where a distance between the top ridge surface and the inner lateral surface 201 satisfies a threshold to stop the leg portion of a upper plunger component from sliding, details of which are described herein).

FIG. 3A and FIG. 3B illustrate example views of an example tube component 300 in accordance with examples of the present disclosure. In particular, FIG. 3A illustrates an example perspective view of the example tube component 300. FIG. 3B illustrates an example cross-sectional view of the example tube component 300 cut by a plane that passes the cut line A-A' in FIG. 3A and is in a parallel arrangement with the central axis of the tube component 300.

In the examples shown in FIG. 3A and FIG. 3B, the example tube component 300 comprises an example pipe element 301. In some embodiments, the example pipe element 301 is in a shape similar to a tube shape, defining at least part of a flow channel 309 for receiving a sample, such that the sample travels through the flow channel 309 in a direction as shown by the dashed arrow in FIG. 3B, additional details which are described herein.

While the figures provide an example of a pipe element, it is noted that the scope of the present disclosure is not limited to these figures. In some examples, an example pipe element may be in other shape(s).

In some embodiments, the example pipe element comprises a top portion 302 and a bottom portion 305. In some embodiments, the top portion 302 and the bottom portion 305 are connected through a middle portion 304. In some embodiments, the top portion 302, the middle portion 304, and the bottom portion 305 form at least a portion of the flow channel 309.

Referring back to FIG. 3A and FIG. 3B, in some embodiments, the example tube component 300 comprises a vent bluff annulus element 303. In some embodiments, the vent bluff annulus element 303 is in a shape similar to a ring shape or a tube shape. While the figures provide an example of a vent bluff annulus element, it is noted that the scope of the present disclosure is not limited to these figures. In some examples, an example vent bluff annulus element may be in other shape(s).

In some embodiments, the vent bluff annulus element 303 extends from the middle portion 304 of the pipe element 301. In some embodiments, the vent bluff annulus element 303 surrounds the top portion 302 of the pipe element 301, such that the top portion 302 of the pipe element 301 is within the vent bluff annulus element 303. In some embodiments, the vent bluff annulus element 303 does not surround the bottom portion 305 of the pipe element 301.

In some embodiments, the vent bluff annulus element 303 has at least one opening 307 on a lateral surface of the vent bluff annulus element 303. In some embodiments, the at least one opening 307 provides a portion of a vent channel and allows a sample to be discharged from an example aerosol collection device, details of which are described herein. In some embodiments, the at least one opening 307 represents a series of vent ports that are configured to intermediately allow air to escape from the vessel such that upper plunger component (as described in detail herein) can be pressed down into the immersed the filter component without increasing pressure in the aerosol collection device, therefore increasing the resistance of the device and assisting in the extraction of fluid (such as sample liquid) from the immersed filter component. As the upper plunger component is pressed down further, the at least one opening 307 will move across the locking ridge of the upper plunger component (details of which are described herein), which in turn closes the vent. In some embodiments, any further pressing on the upper plunger component by a user will build pressure in the device, and force fluid out into an extraction cartridge, details of which are described herein.

Figure 4A:
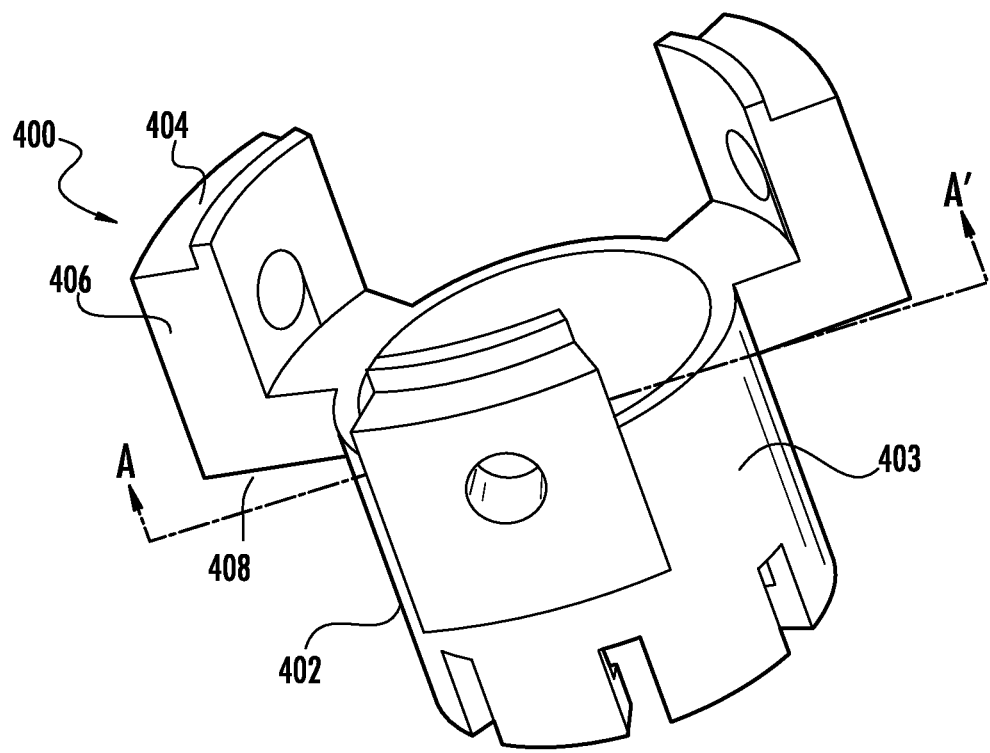
FIG. 4A and FIG. 4B illustrate example views of an example lower plunger component in accordance with examples of the present disclosure.
Figure 4B:
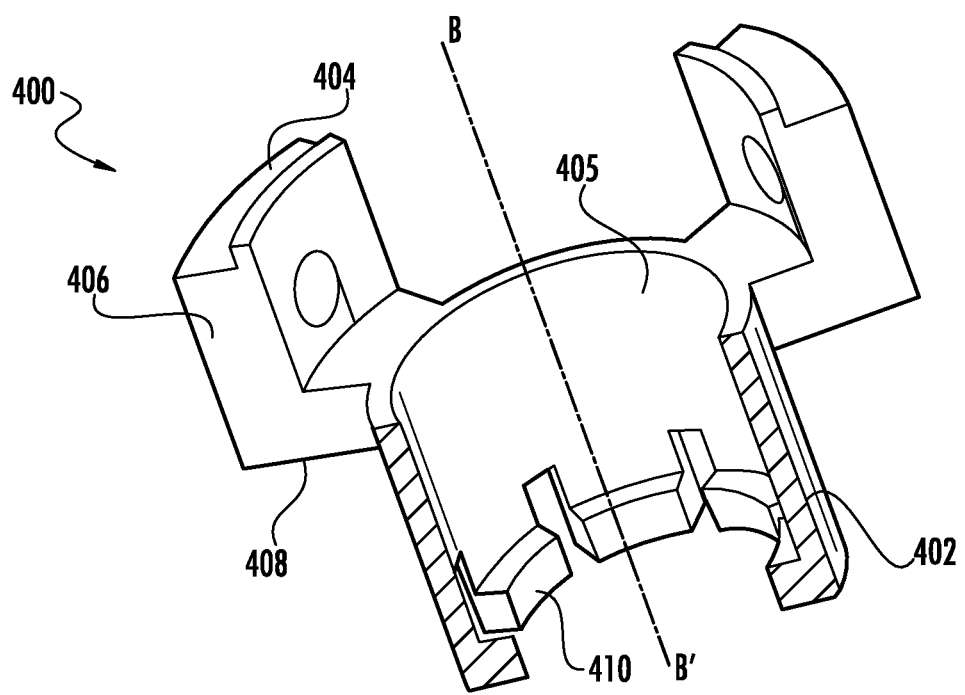

FIG. 4A and FIG. 4B illustrate example views of an example lower plunger component 400 in accordance with examples of the present disclosure. In particular, FIG. 4A illustrates an example perspective view of the example lower plunger component 400. FIG. 4B illustrates an example cross-sectional view of the example lower plunger component 400 cut by a plane that passes the cut line A-A' in FIG. 4A and is in a parallel arrangement with the central axis of the tube component 300.

In some embodiments, the example lower plunger component 400 comprises an example plunger annulus element 402. In some embodiments, the example plunger annulus element 402 is in a shape similar to a ring shape or a tube shape.

While the figures provide an example of a plunger annulus element, it is noted that the scope of the present disclosure is not limited to the description above. In some examples, an example plunger annulus element may be in other shape(s).

In some embodiments, the example plunger annulus element 402 has an outer lateral surface 403. In some embodiments, at least one plunger support wing (for example, an example plunger support wing 404) is disposed on the outer lateral surface 403 of the example plunger annulus element 402.

In the example shown in FIG. 4A and FIG. 4B, the example plunger support wing 404 comprises a bottom portion 408 and a lateral portion 406. In some embodiments, the bottom portion 408 of the example plunger support wing 404 is connected to and extends radically outward from the outer lateral surface 403 of the example plunger annulus element 402. In some embodiments, the bottom portion 408 of the example plunger support wing 404 is connected to and in a perpendicular or orthogonal arrangement with the lateral portion 406 of the example plunger support wing 404.

In some embodiments (for example, as shown in FIG. 4B), the example plunger annulus element 402 comprises at least one plunger leg component (for example, an example plunger leg component 410). In some embodiments, the at least one plunger leg component extends inward to a central axis of the plunger annulus element and is in a perpendicular arrangement with the inner lateral surface of the plunger annulus element. In the example shown in FIG. 4B, the example plunger leg component 410 extends inward to a central axis B-B' of the example plunger annulus element 402 and is in a perpendicular arrangement with the inner lateral surface 405 of the example plunger annulus element 402.

In some embodiments, a bottom surface of the example plunger leg component 410 is in contact with a top surface of an example filter component of the aerosol collection device, details of which are described herein.

FIG. 5A, FIG. 5B, FIG. 5C, FIG. 5D, FIG. 5E, FIG. 5F, and FIG. 5G each illustrates an example view of at least a portion of an example upper plunger component in accordance with examples of the present disclosure.

Figure 5A:
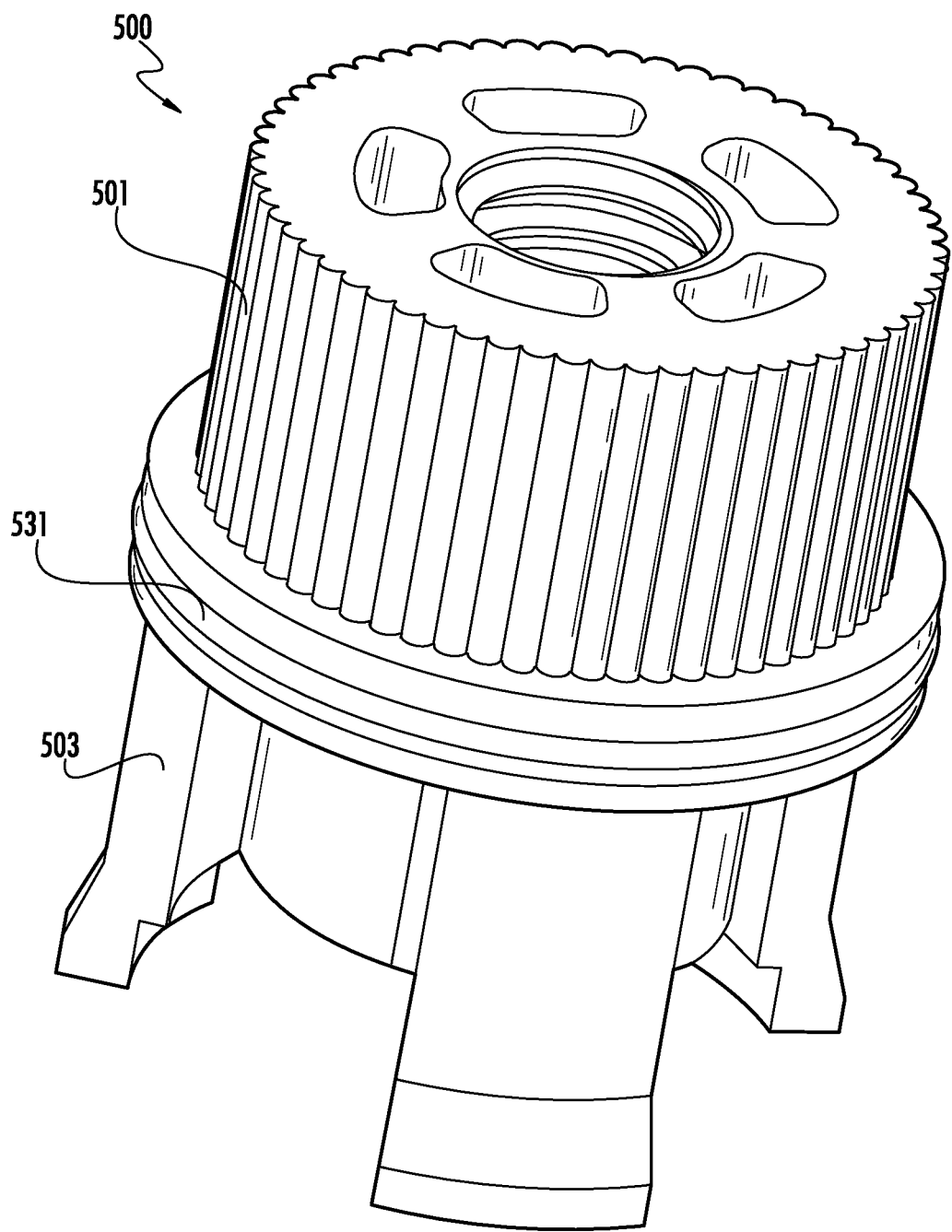
FIG. 5A, FIG. 5B, FIG. 5C, FIG. 5D, FIG. 5E, FIG. 5F, and FIG. 5G each illustrates an example view of at least a portion of an example upper plunger component in accordance with examples of the present disclosure.
Figure 5B:
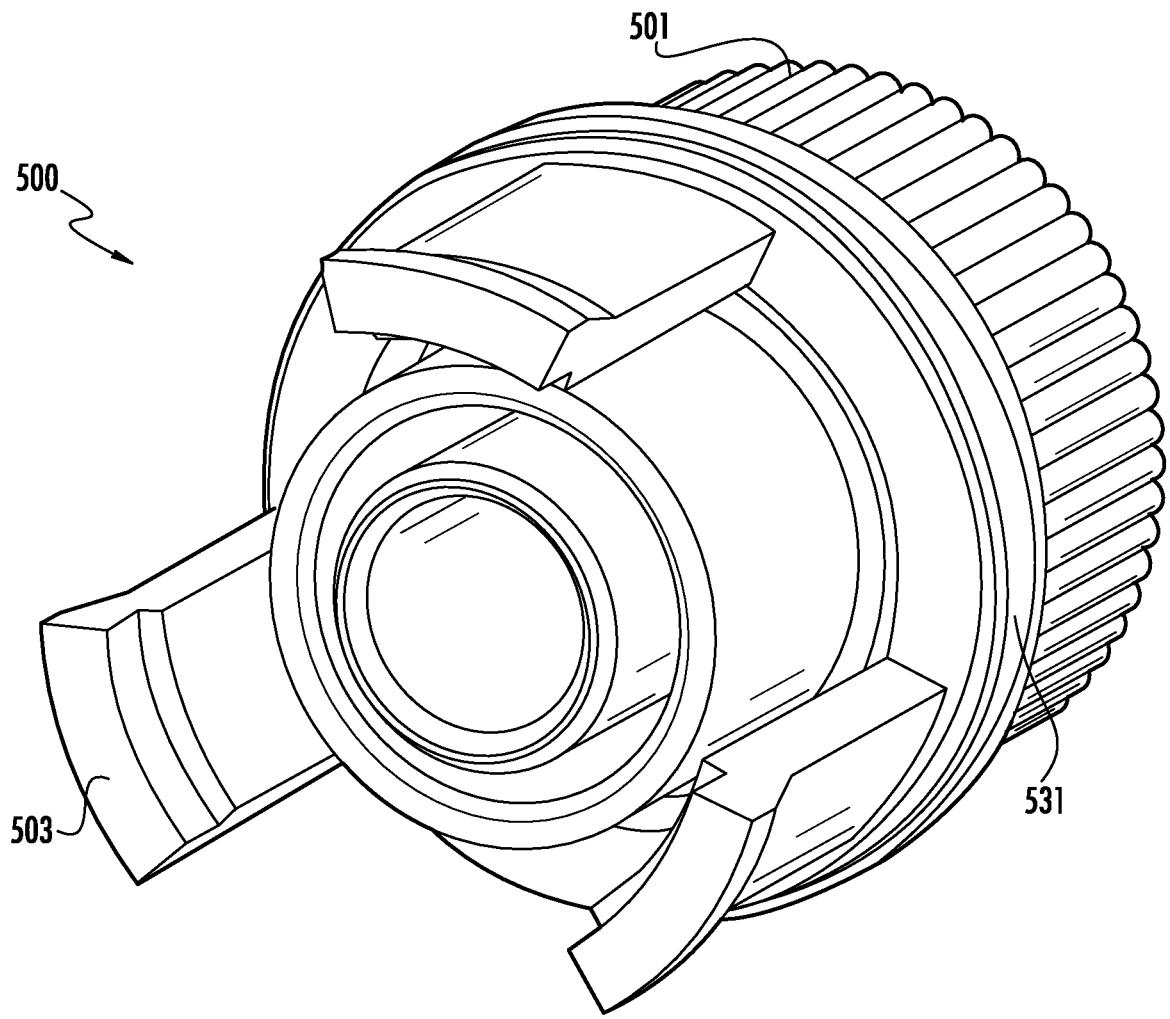
Figure 5C:
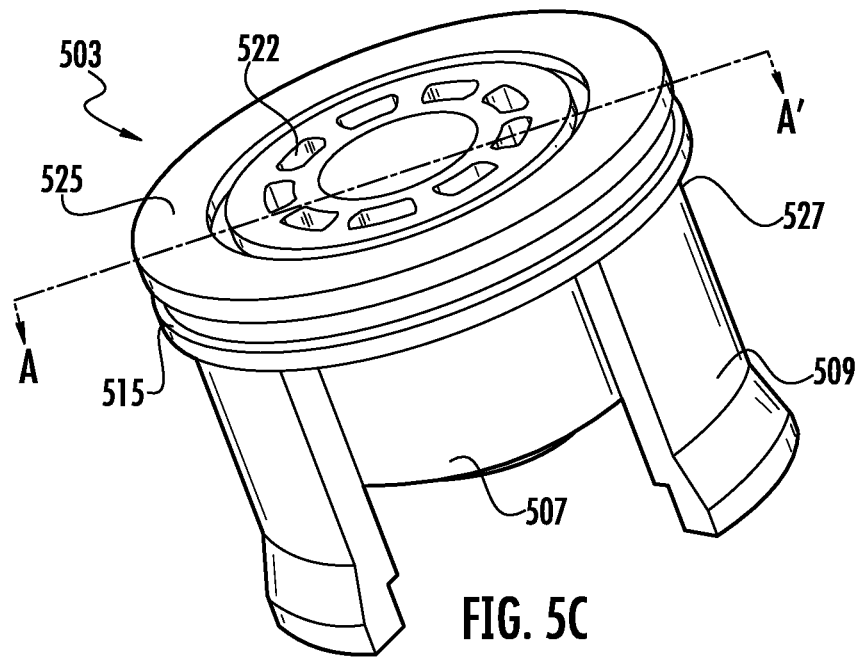
Figure 5D:
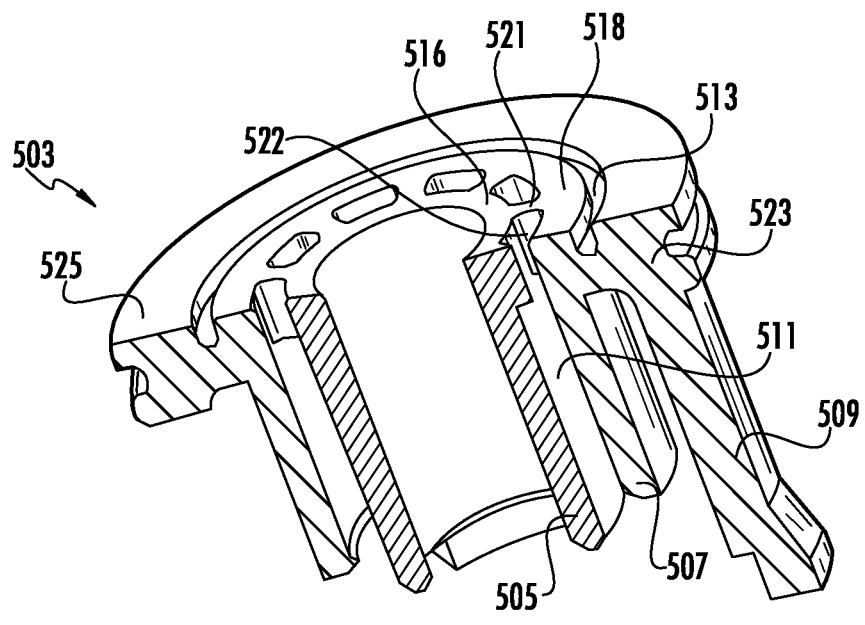
Figure 5E:
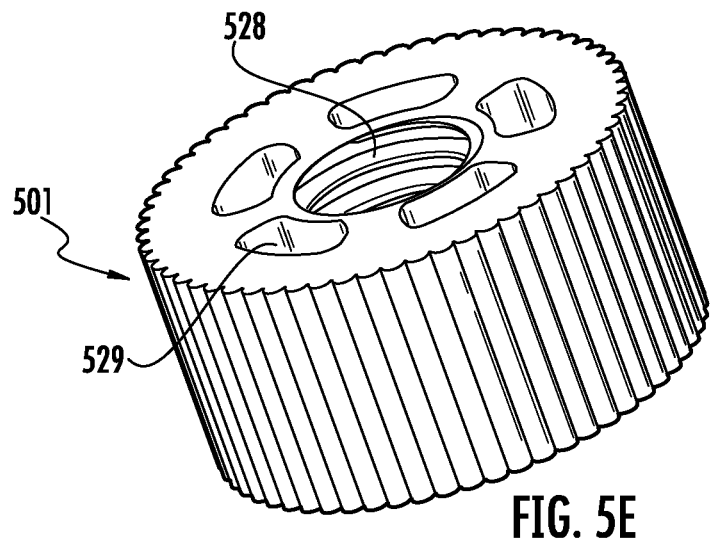
Figure 5F:
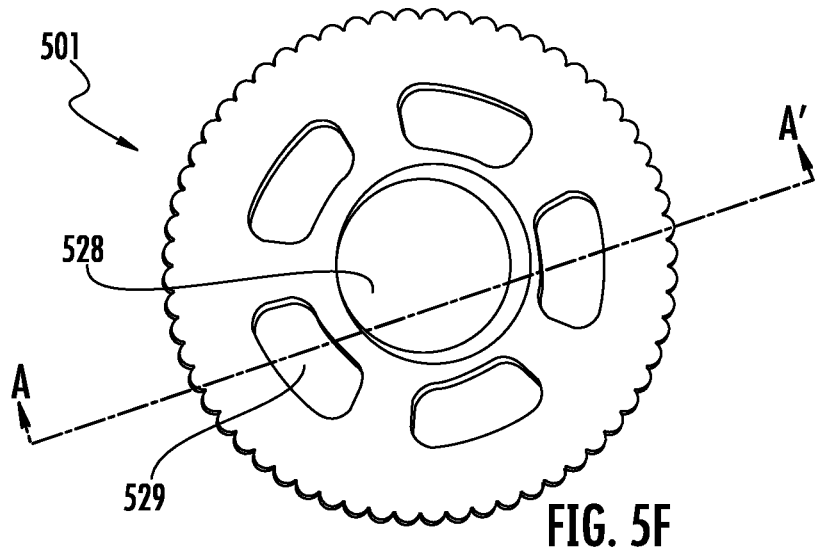
Figure 5G:
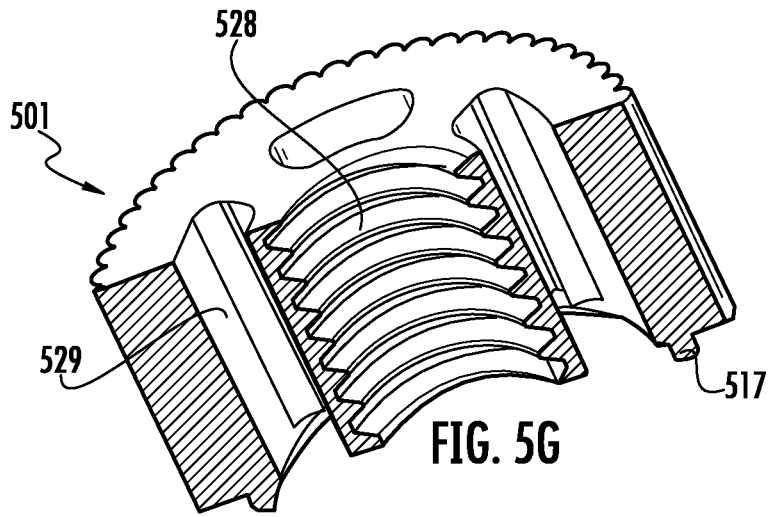

In particular, FIG. 5A and FIG. 5B illustrate different views of an example upper plunger component 500, which comprises at least an example plunger head element 501 and an example plunger body element 503. FIG. 5C and FIG. 5D illustrate example views of the example plunger body element 503. FIG. 5E, FIG. 5F, FIG. 5G illustrate example views of the example plunger head element 501.

Referring now to FIG. 5A and FIG. 5B, the example plunger head element 501 is secured to the example plunger body element 503.

In some embodiments, the example plunger head element 501 is secured to the example plunger body element 503 through chemical means, such as, but not limited to, a chemical adhesive (such as, but not limited to, cyanoacrylate). Additionally, or alternatively, the example plunger head element 501 is secured to the example plunger body element 503 through mechanical means, such as, but not limited to, through a tongue-to-groove fit, details of which are described herein. Additionally, or alternatively, the example plunger head element 501 is secured to the example plunger body element 503 through other means.

In some embodiments, an example o-ring 531 is disposed on an example o-ring groove on the example plunger head element 501, details of which are described herein.

Referring now to FIG. 5C and FIG. 5D, example views of the example plunger body element 503 are shown. In particular, FIG. 5C illustrates an example perspective view of the example plunger body element 503. FIG. 5D illustrates an example cross-sectional view of the example plunger body element 503 cut by a plane that passes the cut line A-A' in FIG. 5C and is in a parallel arrangement with the central axis of the example plunger body element 503.

In some embodiments, the example plunger body element 503 comprises at least a central annulus portion 505, an intermedial annulus portion 507, and at least one leg portion 509.

In some embodiments, the central annulus portion 505 is in a shape similar to a ring shape or a tube shape. While the figures provide an example of a central annulus portion, it is noted that the scope of the present disclosure is not limited to the figures. In some examples, an example central annulus portion may be in other shape(s).

In some embodiments, the intermedial annulus portion 507 is in a shape similar to a ring shape or a tube shape.

While the figures provide an example of an intermedial annulus portion, it is noted that the scope of the present disclosure is not limited to the figures. In some examples, an example intermedial annulus portion may be in other shape(s).

In some embodiments, the central annulus portion 505 is positioned within the intermedial annulus portion 507. In the example shown in FIG. 5D, a first end 516 of the central annulus portion 505 is at least partially connected to a second end 518 of the intermedial annulus portion 507 through at least a bridge connector 521. In some embodiments, the central annulus portion 505 is not entirely connected to the intermedial annulus portion 507, and a gap may be formed between the central annulus portion 505 and the intermedial annulus portion 507, and/or an opening/aperture on a top surface of the plunger body element 503 may be defined between the bridge connectors. For example, as shown in FIG. 5D, a portion of at least one vent channel (for example, vent channel 511) may be formed between the central annulus portion 505 and the intermedial annulus portion 507, and the opening 522 may serve as a vent port of the vent channel 511. As described in detail further herein, the vent channel 511 provides a passageway for discharging a sample from the aerosol collection device.

In some embodiments, at least one filter element may be positioned to cover the opening 522. In some embodiments, at least one filter element is positioned between the plunger head element 501 and the plunger body element 503. As the vent channel 511 is configured to discharge sample from the aer embodiments, to secure the example plunger head element 501 to the example plunger body element 503, the annulus tongue 517 is locked and/or attached to the annulus groove 513 of the plunger body element 503, with or without chemical adhesives.

Referring back to FIG. 5E, FIG. 5F, and FIG. 5G, the example plunger head element 501 defines a central bore 528 and one or more apertures (for example, an aperture 529) positioned radially outward from the central bore 528. In some embodiments, each of the plurality of apertures defines at least a portion of a vent channel, details of which are described herein.

In some embodiments, at least one filter element may be positioned to cover each of the plurality of apertures. As described above, the vent channel is configured to discharge sample from the aerosol collection device. As such, the at least one filter element is configured to remove containment, aerosol, bacteria, virus, and/or the like from the sample before it is discharged, so that the sample discharged from the aerosol collection device does not cause health or environment hazard.

FIG. 6A, FIG. 6B, FIG. 6C, FIG. 6D, FIG. 6E, FIG. 6F, FIG. 6G, FIG. 6H, FIG. 6I, and FIG. 6J illustrate an example method for assembling an example aerosol collection device in accordance with examples of the present disclosure.

Figure 6A:
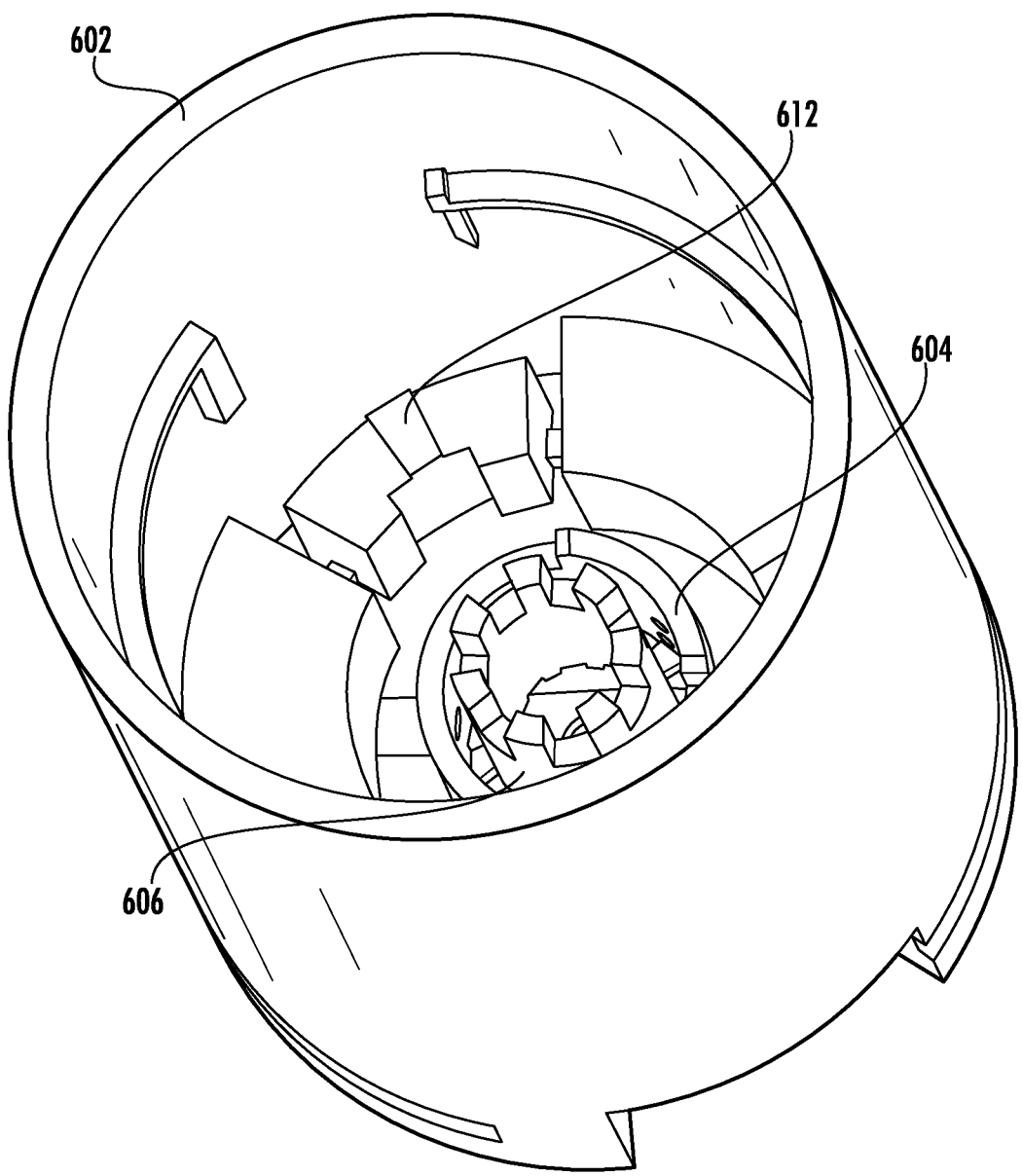
FIG. 6A, FIG. 6B, FIG. 6C, FIG. 6D, FIG. 6E, FIG. 6F, FIG. 6G, FIG. 6H, FIG. 6I, and FIG. 6J illustrate an example method for assembling an example aerosol collection device in accordance with examples of the present disclosure.

Referring now to FIG. 6A, the example method for assembling an example aerosol collection device in accordance with examples of the present disclosure comprises providing (for example, but not limited to, molding) a vessel component 602. As described above, the vessel component 602 comprises at least a valve support annulus element 606 and a sample distribution annulus element 604.

Figure 6B:
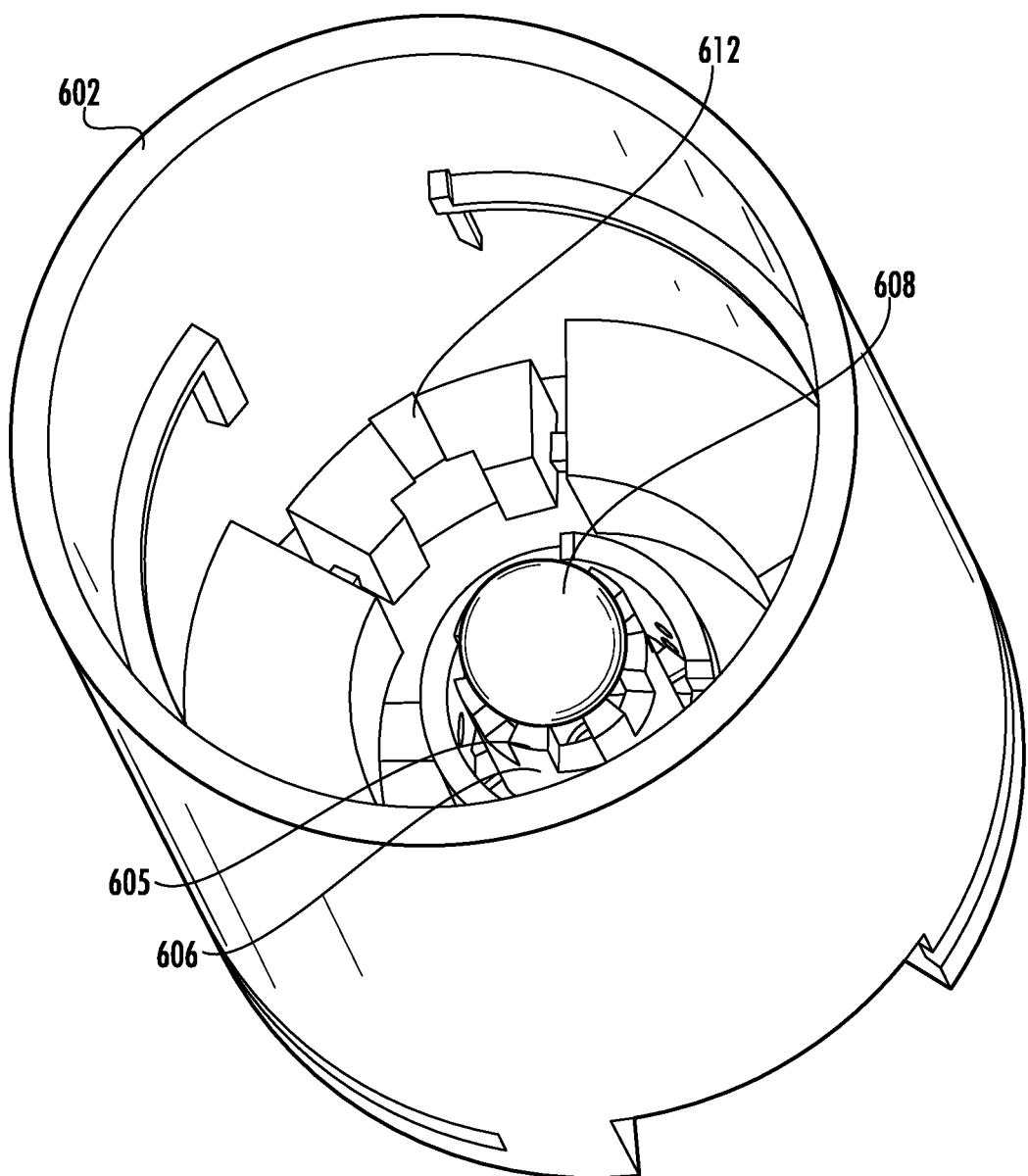

Referring now to FIG. 6B, the example method for assembling an example aerosol collection device in accordance with examples of the present disclosure comprises positioning a valve component 608 on the valve support annulus element 606.

In some embodiments, the valve component 608 is a sphere object. In some embodiments, the valve component 608 is in other shape(s) and/or form(s). In some embodiments, the valve component 608 may comprise material such as, but not limited to, plastics including PVC and CPVC.

As described above, the valve support annulus element 606 may comprise a plurality of supporting beams 605. In some embodiments, the valve component 608 is placed on top of and supported by the plurality of supporting beams 605.

Figure 6C:
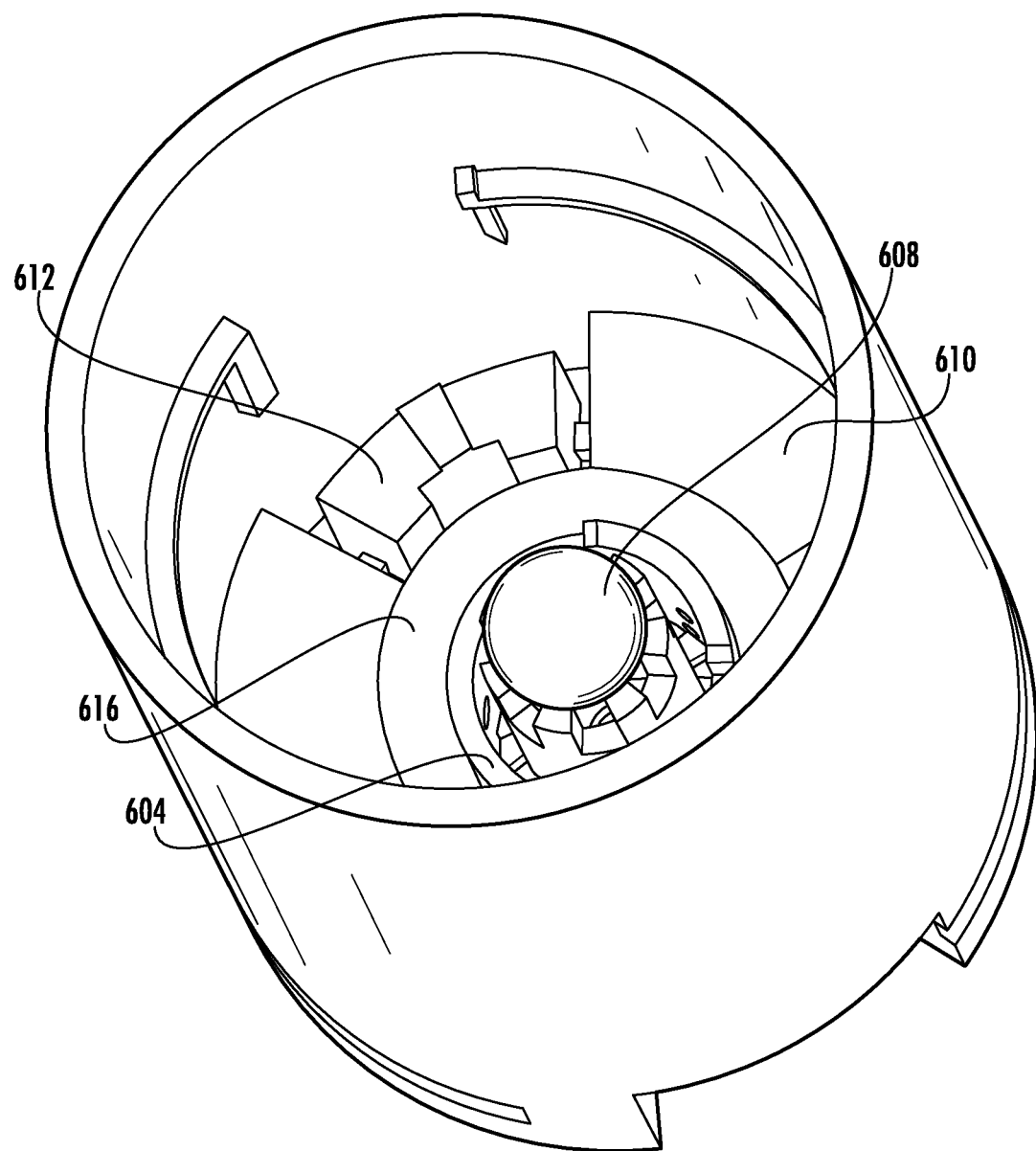

Referring now to FIG. 6C, the example method for assembling an example aerosol collection device in accordance with examples of the present disclosure comprises inserting a filter component 616 between the sample distribution annulus element 604 and at least one of a filter support body element 610 or a capsule extraction body element 612 of the vessel component 602. In some embodiments, the filter component 616 is positioned in the aerosol collection device prior to positioning the valve component 608. In some embodiments, the filter component 616 is positioned in the aerosol collection device subsequent to positioning the valve component 608.

In some embodiments, the filter component 616 is in a ring or a tube shape. In some embodiments, the filter component 616 is in other shape(s) and/or form(s). In some embodiments, the filter component 616 is a dry filter. During the operation of the aerosol collection device, a buffer solution is released and wets the filter component 616, details of which are described herein.

In some embodiments, the filter component 616 may be manufactured or provided in a rectangular shape having a dimension of 2.1" (length)×0.5" (width)×0.125" (thickness), and two edges of the rectangular shape may be connected to one another to form the ring/tube shape. In some embodiments, the filter component 616 may have other dimensional measurement(s).

In some embodiments, the filter component 616 may comprise material such as, but not limited to, one or more of 2122K302 (a Merv 6 polyester), 2173K133 (a sparse fiberglass filter), and/or 2182K51 (a polyester based Merv 6 with a tacky surface treatment). In some embodiments, the filter component 616 may comprise other material(s).

Figure 6D:
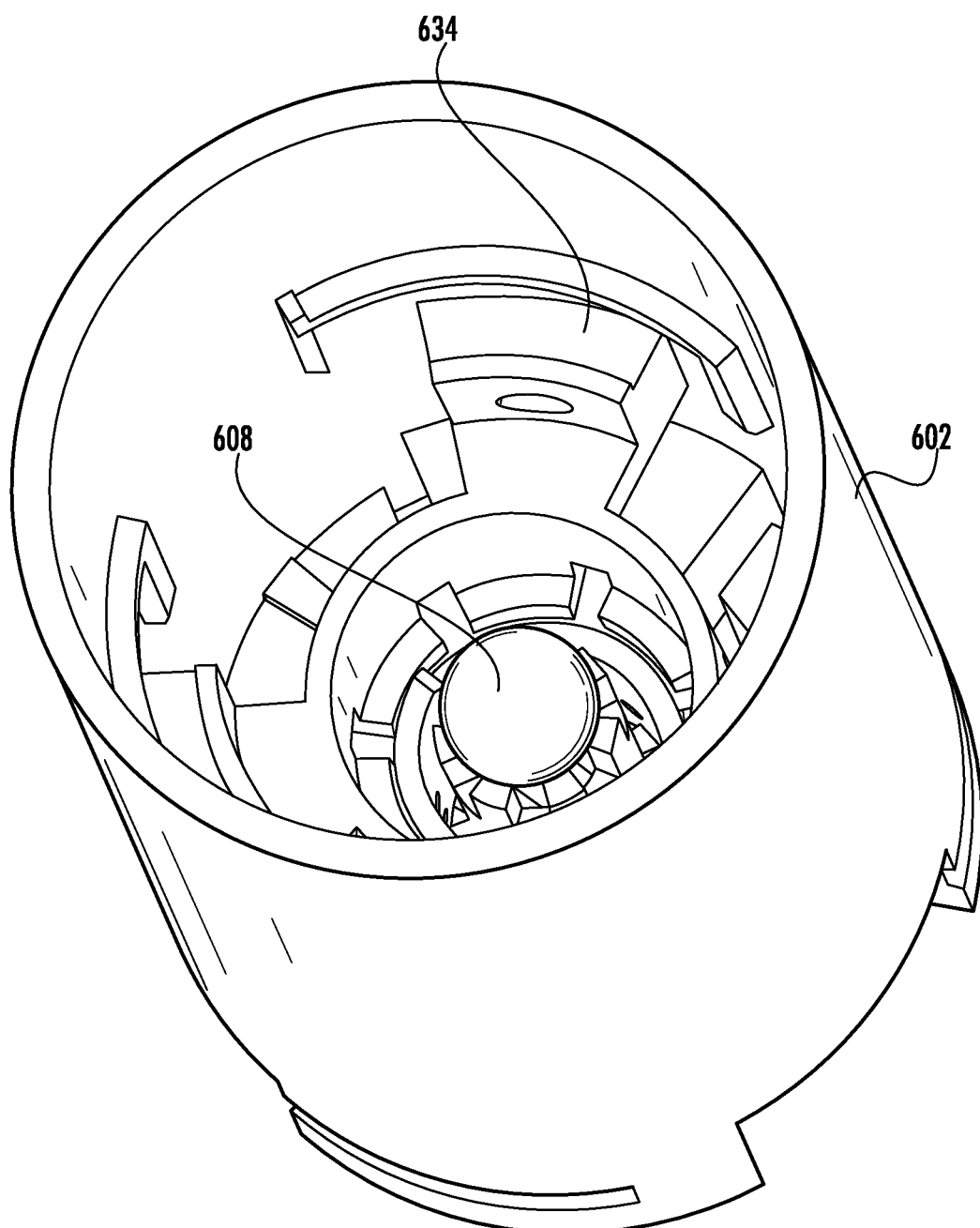

Referring now to FIG. 6D, the example method for assembling an example aerosol collection device in accordance with examples of the present disclosure comprises positioning a lower plunger component 634 on a top surface of the filter component 616. In some embodiments, the lower plunger component 634 is positioned prior to positioning a tube component in the aerosol collection device, details of which are described herein. In some embodiments, the lower plunger component 634 is placed on the top surface of the filter component 616 prior to positioning the valve component 608 on the valve support annulus element 606. In some embodiments, the lower plunger component 634 is placed on the top surface of the filter component 616 subsequent to positioning the valve component 608 on the valve support annulus element 606.

Figure 6E:
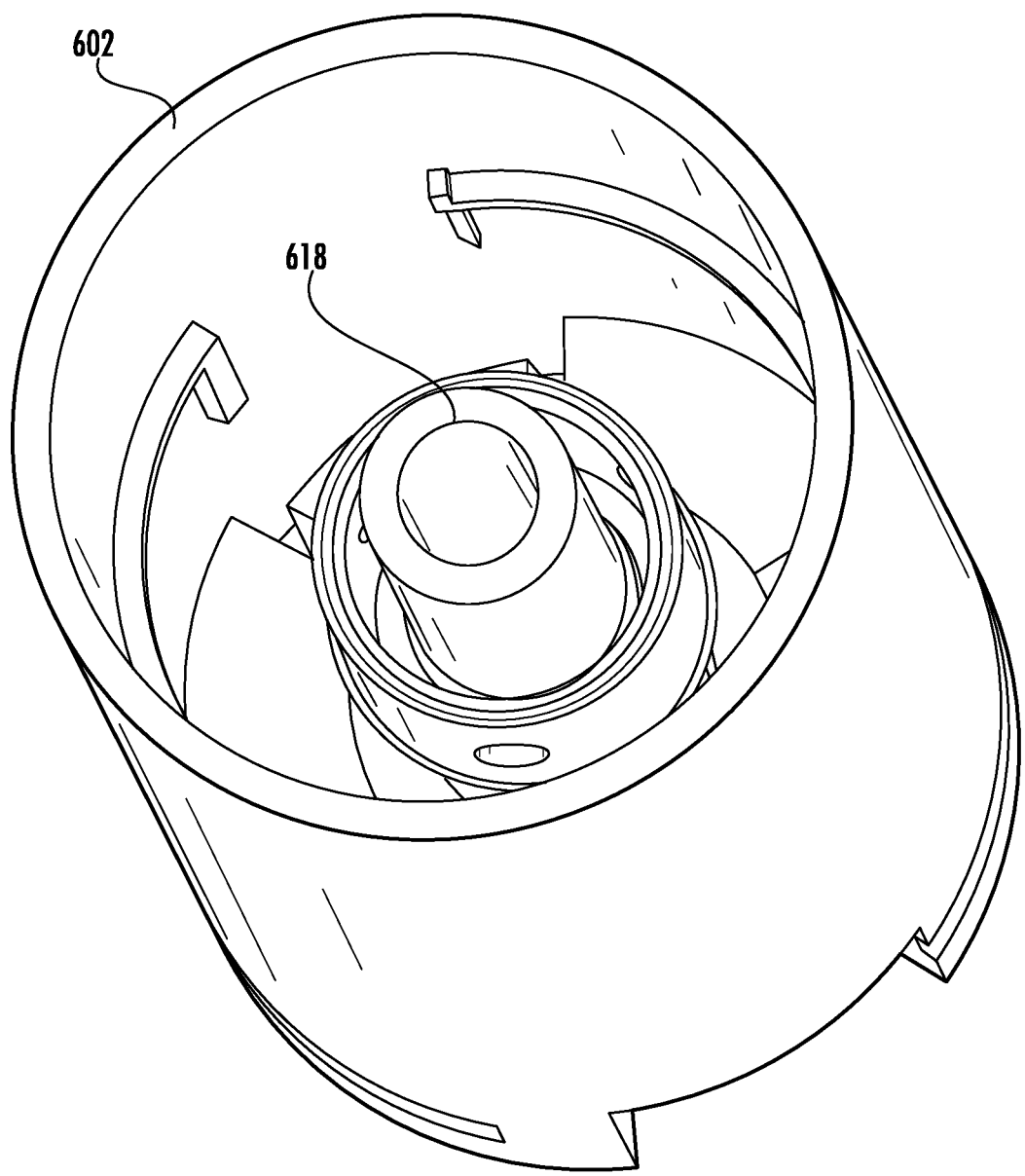
Figure 6F:
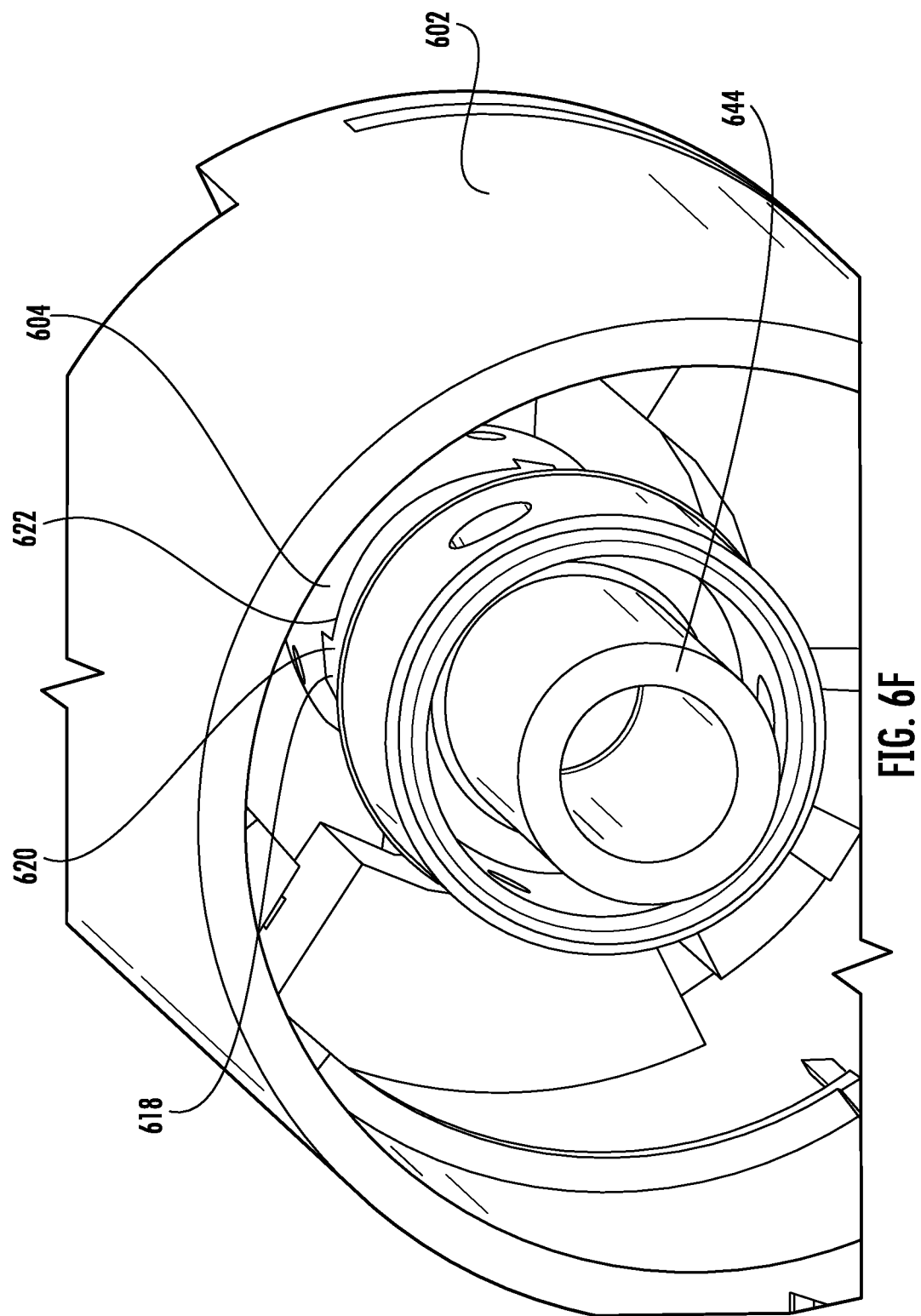

Referring now to FIG. 6E and FIG. 6F the example method for assembling an example aerosol collection device in accordance with examples of the present disclosure comprises securing a tube component 618 to the sample distribution annulus element 604.

As shown in FIG. 6F, the tube component 618 may comprise a notch 620 and the sample distribution annulus element 604 may comprise a notch 622. In some embodiments, the tube component 618 is secured to the sample distribution annulus element 604 through a slide interference fit between the notch 620 and the notch 622, as shown in FIG. 6F. Additionally, or alternatively, the tube component 618 is secured to the sample distribution annulus element 604 through other means, including, but not limited to chemical means such as an adhesive glue.

Figure 6G:
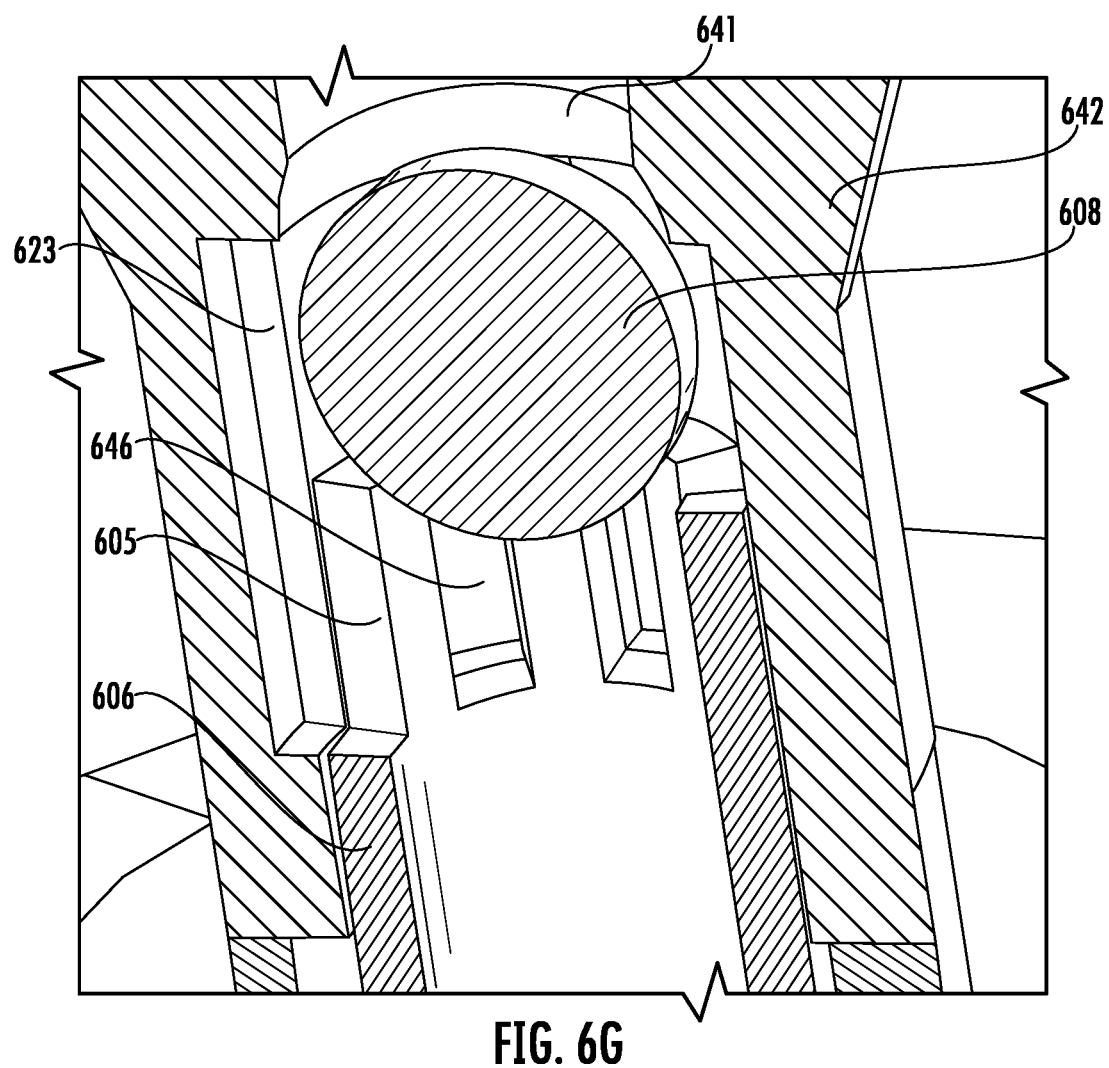

FIG. 6G illustrates a portion of an example cross-sectional view of the example device shown in FIG. 6E and FIG. 6F. In the example shown in FIG. 6G, the valve component 608 is positioned between the plurality of supporting beams 605 of the valve support annulus element 606 and an inner surface 641 of a middle portion 642 of a pipe element 644 of the tube component 618.

In some embodiments, the inner surface 641 of the middle portion 642 may comprise a curved surface corresponding to the surface of the valve component 608. As described above, the pipe element 644 defines at least a portion of a flow channel for receiving a sample, and the valve component 608 is configured to prevent a user from accidentally sucking a buffer solution from the aerosol collection device through the flow channel. For example, when a user sucks air through the pipe element 623, the valve component 608 moves towards the middle portion 642 of the pipe element 644 and becomes in contact with the inner surface 641, which may seal the flow channel and prevent the buffer solution from being sucked out of the aerosol collection device through the flow channel.

In some embodiments, a sample flows through the gap between the inner surface 641 of the middle portion 642, through the gaps between the plurality of supporting beams 605, and through the valve support annulus element 606 towards a bottom of the vessel component 602.

In some embodiments, the inner surface of the bottom portion of the pipe element 644 may comprise one or more indentation portions (for example, an indentation portion 646) corresponding to the gaps between the plurality of supporting beams 605. As such, the sample may flow through the gaps between the plurality of supporting beams 605 and the one or more indentation portions.

Figure 6H:
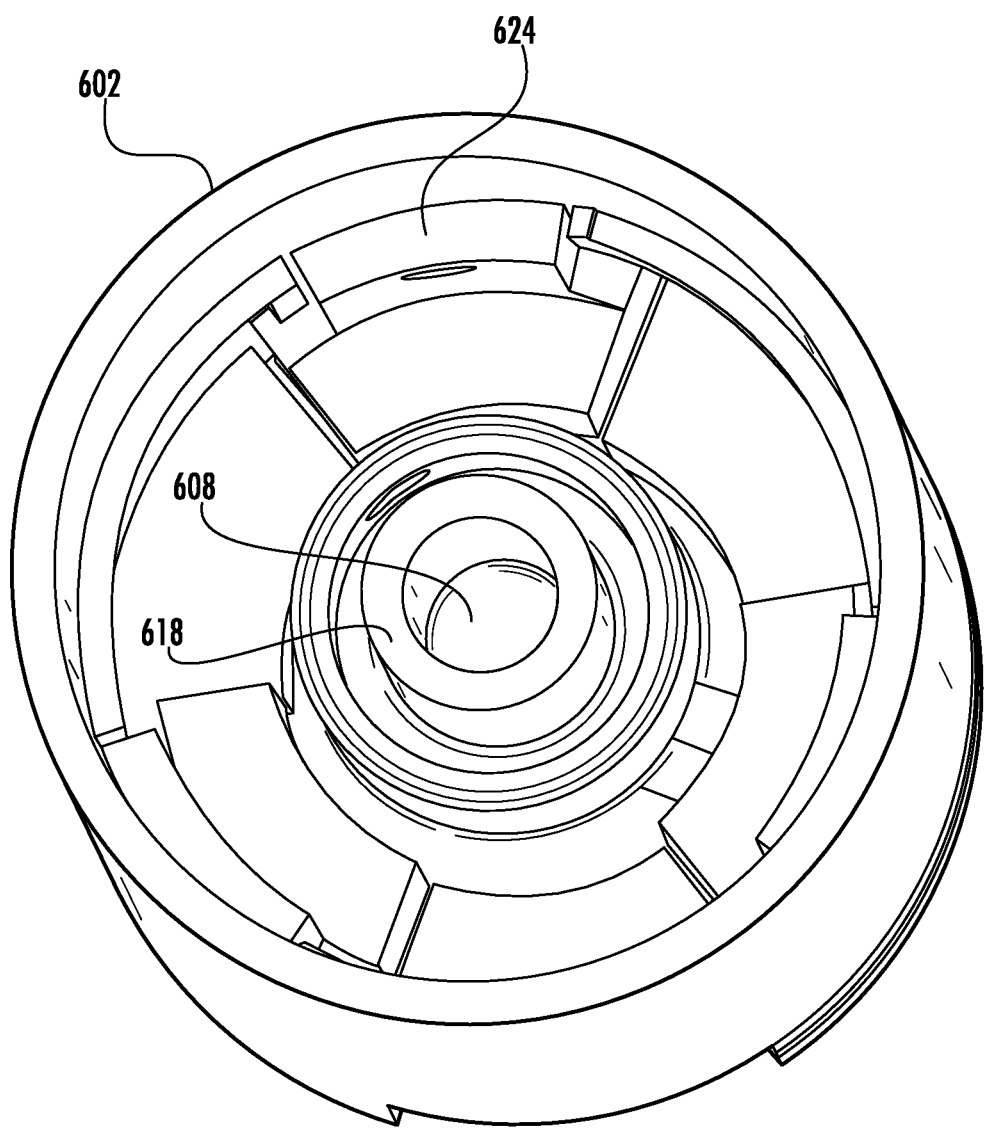
Figure 6I:
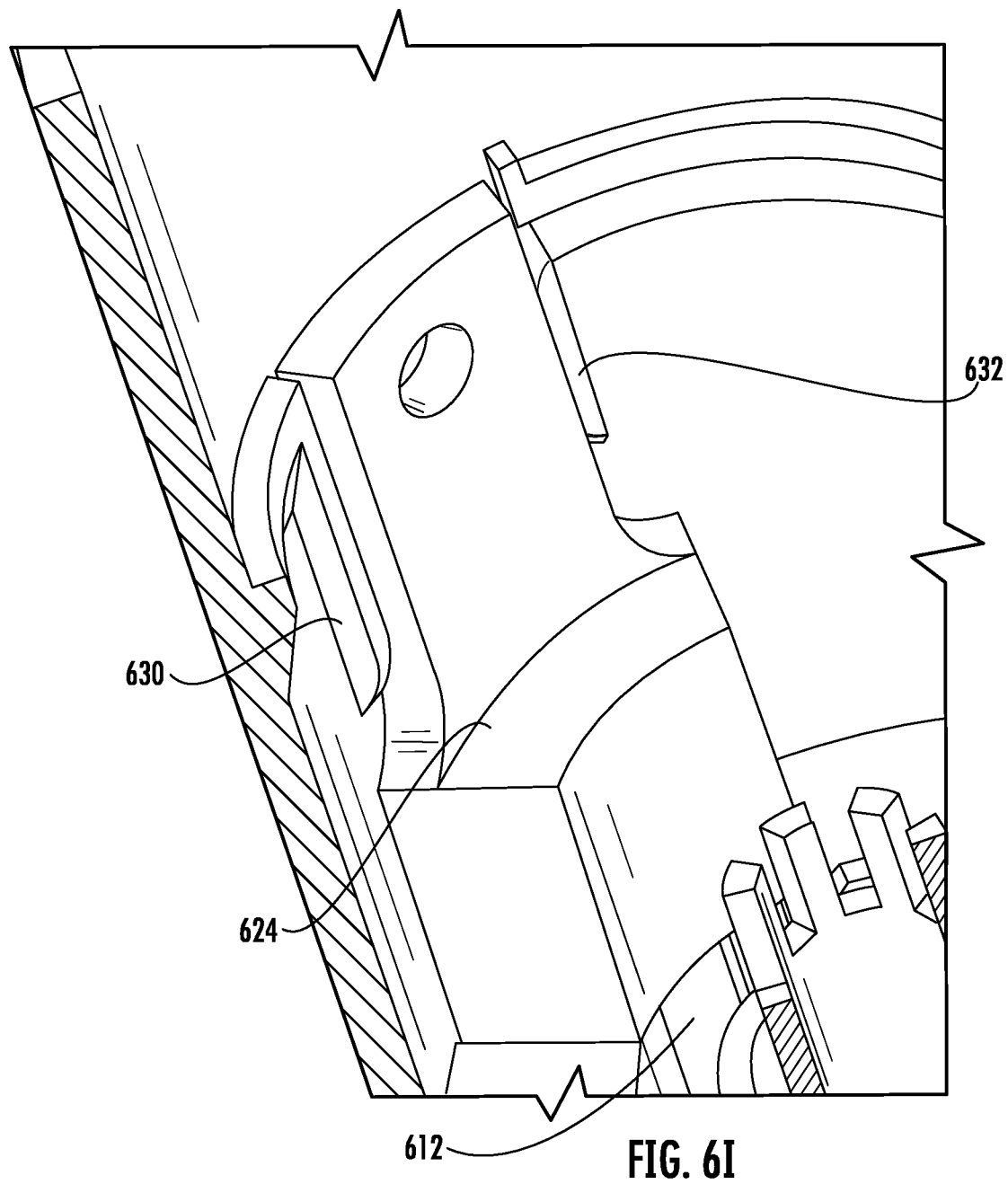

Referring now to FIG. 6H and FIG. 6I, the example method for assembling an example aerosol collection device in accordance with examples of the present disclosure comprises positioning at least one capsule component 624 on a top surface of the capsule extraction body element 612. In some embodiments, the at least one capsule component 624 can be positioned on a top surface of the capsule extraction body element 612 at any step of the example method prior to the step of positioning the upper plunger component into the example aerosol collection device (details of which are described herein). In some embodiments, the at least one capsule component is secured between at least two vertical ridge elements of the vessel component. In the example shown in FIG. 6H, the at least one capsule component 624 is secured between the a first vertical ridge element 630 (for example, a vertical stop ridge element as described herein) and the second vertical ridge element 632 (for example, a vertical lock ridge element as described herein).

Figure 6J:
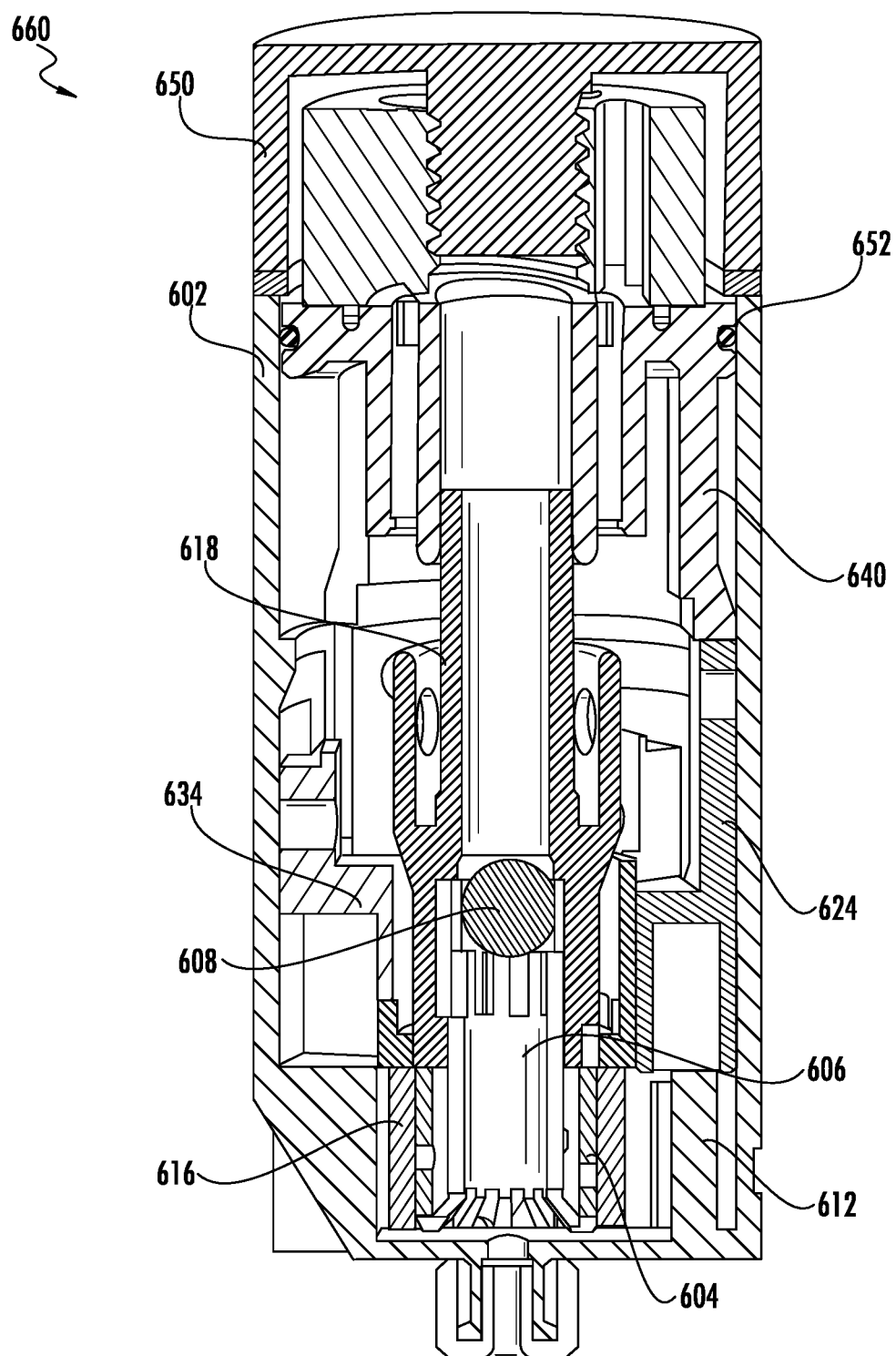

Referring now to FIG. 6J, the example method for assembling an example aerosol collection device in accordance with examples of the present disclosure comprises securing a upper plunger component 640 on a top surface of the at least one capsule component 624, and optionally securing a cap component 650 on the upper plunger component 640. In some embodiments, the upper plunger component 640 is secured to an inner lateral surface of the vessel component 602 through an o-ring 652.

FIG. 6J illustrates an example of an assembled aerosol collection device 660. As shown in FIG. 6J, the assembled aerosol collection device 660 comprises a vessel component 602. In some embodiments, the vessel component 602 comprises a sample distribution annulus element 604, a valve support annulus element 606 within the sample distribution annulus element 604, at least one capsule extraction body element (for example, capsule extraction body element 612) positioned radially outward from the sample distribution annulus element 604.

In some embodiments, the assembled aerosol collection device 660 comprises a valve component 608 supported by the valve support annulus element 606. In some embodiments, the assembled aerosol collection device 660 comprises a tube component 618 secured to the sample distribution annulus element 604.

In some embodiments, the assembled aerosol collection device 660 comprises at least one capsule component 624 positioned on a top surface of the at least one capsule extraction body element (for example, capsule extraction body element 612).

In some embodiments, the assembled aerosol collection device 660 comprises the upper plunger component 640 positioned on a top surface of the at least one capsule component 624.

In some embodiments, the assembled aerosol collection device 660 comprises the filter component 616 inserted between the sample distribution annulus element 604 and the at least one capsule extraction body element (for example, capsule extraction body element 612) (and/or a filter support body element).

In some embodiments, the assembled aerosol collection device 660 comprises a lower plunger component 634 positioned on a top surface of the filter component 616.

In some embodiments, the assembled aerosol collection device 660 comprises a cap component 650 secured to the upper plunger component 640. For example, the upper plunger component 640 comprises a plunger head element defining a central bore having threads on the inner surface, and the cap component 650 comprises an extended portion having threads on the outer surface. The extended portion of the cap component 650 may be fasten to the central bore of the plunger head element of the upper plunger component 640 through threads.

In some embodiments, the cap component 650 is configured to seal the flow channel and the vent channel of the aerosol collection device (details of the flow channel and the vent channel are described further herein). In some embodiments, the cap component 650 may prevent contamination.

FIG. 7A, FIG. 7B, FIG. 7C, FIG. 7D, and FIG. 7E illustrate an example method for operating an example aerosol collection device in accordance with examples of the present disclosure.

Figure 7A:
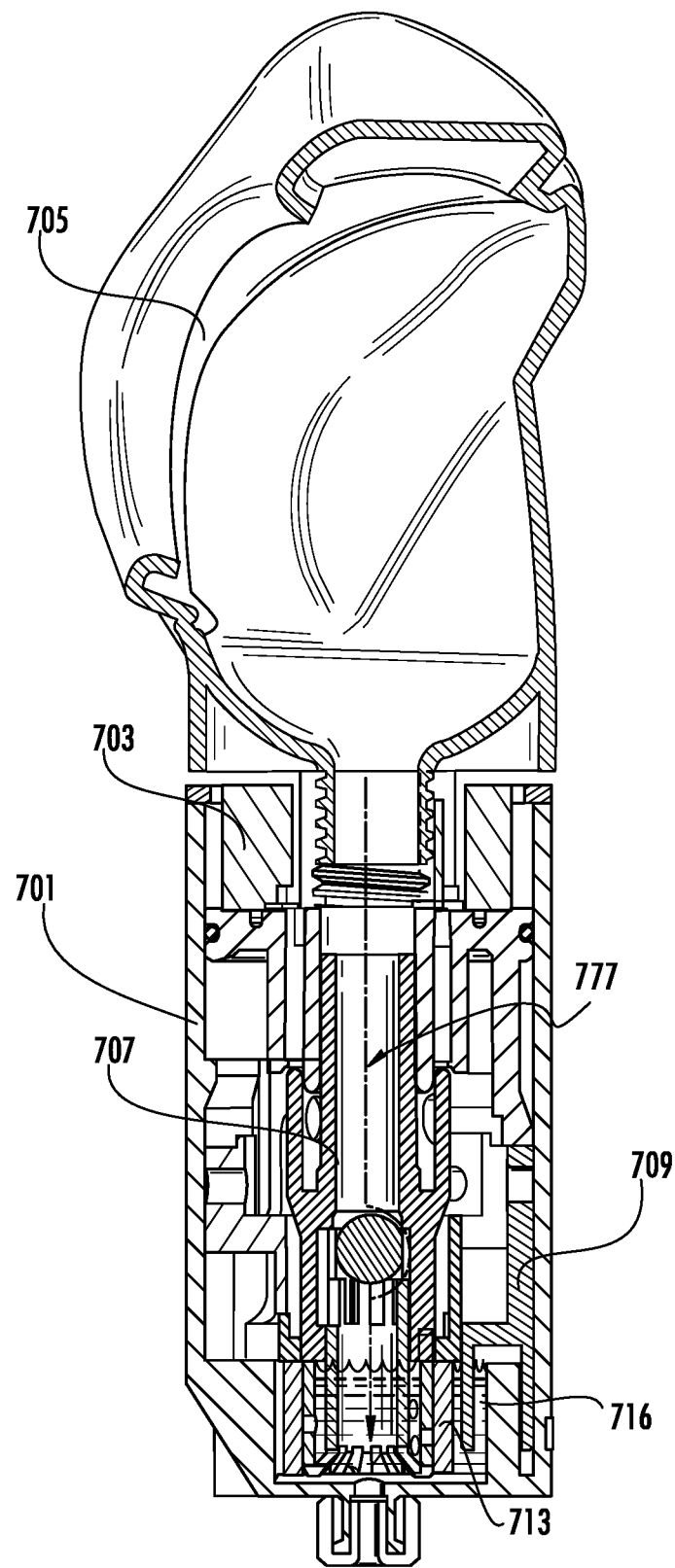
FIG. 7A, FIG. 7B, FIG. 7C, FIG. 7D, and FIG. 7E illustrate an example method for operating an example aerosol collection device in accordance with examples of the present disclosure.

Referring now to FIG. 7A, the example method for operating an example aerosol collection device in accordance with examples of the present disclosure comprises removing a cap component of the device body 701 from an upper plunger component 703 of the device body 701 and connecting a sample transfer adapter 705 to a flow channel defined by at least the upper plunger component 703 and a tube component 707.

As described above, the upper plunger component 703 comprises a plunger head element defining a central bore having threads on the inner surface, and the sample transfer adapter 705 comprises an extended portion having threads on the outer surface. The extended portion of the sample transfer adapter 705 may be fasten to the central bore of the plunger head element of the upper plunger component 703 through threads.

In some embodiments, the device body 701 comprises at least one capsule component 709 storing buffer solution. In some embodiments, connecting the sample transfer adapter 705 to the upper plunger component 703 causes a vertically downward force exerted on the upper plunger component 703. In some embodiments, the upper plunger component 703 is positioned on a top surface of the at least one capsule component 709, and the vertically downward force in turn causes a release of the buffer solution 716 from at least one capsule component 709 to a filter component 713 within the device body 701, details of which are described herein.

In some embodiments, the example method for assembling an example aerosol collection device in accordance with examples of the present disclosure comprises causing sample flow into the device body 701 through the flow channel. For example, the sample flows into the device body 701 when a user exhales or coughs into the sample transfer adapter 705. In the example shown in FIG. 7A, the flow direction of the sample in the flow channel is shown by the dashed arrow 777. In some embodiments, the sample is in contact with the buffer solution 716 within the device body 701. For example, as the user exhales or coughs into the sample transfer adapter 705, the air may be blown into the buffer solution 716, forming one or more bubbles.

Figure 7B:
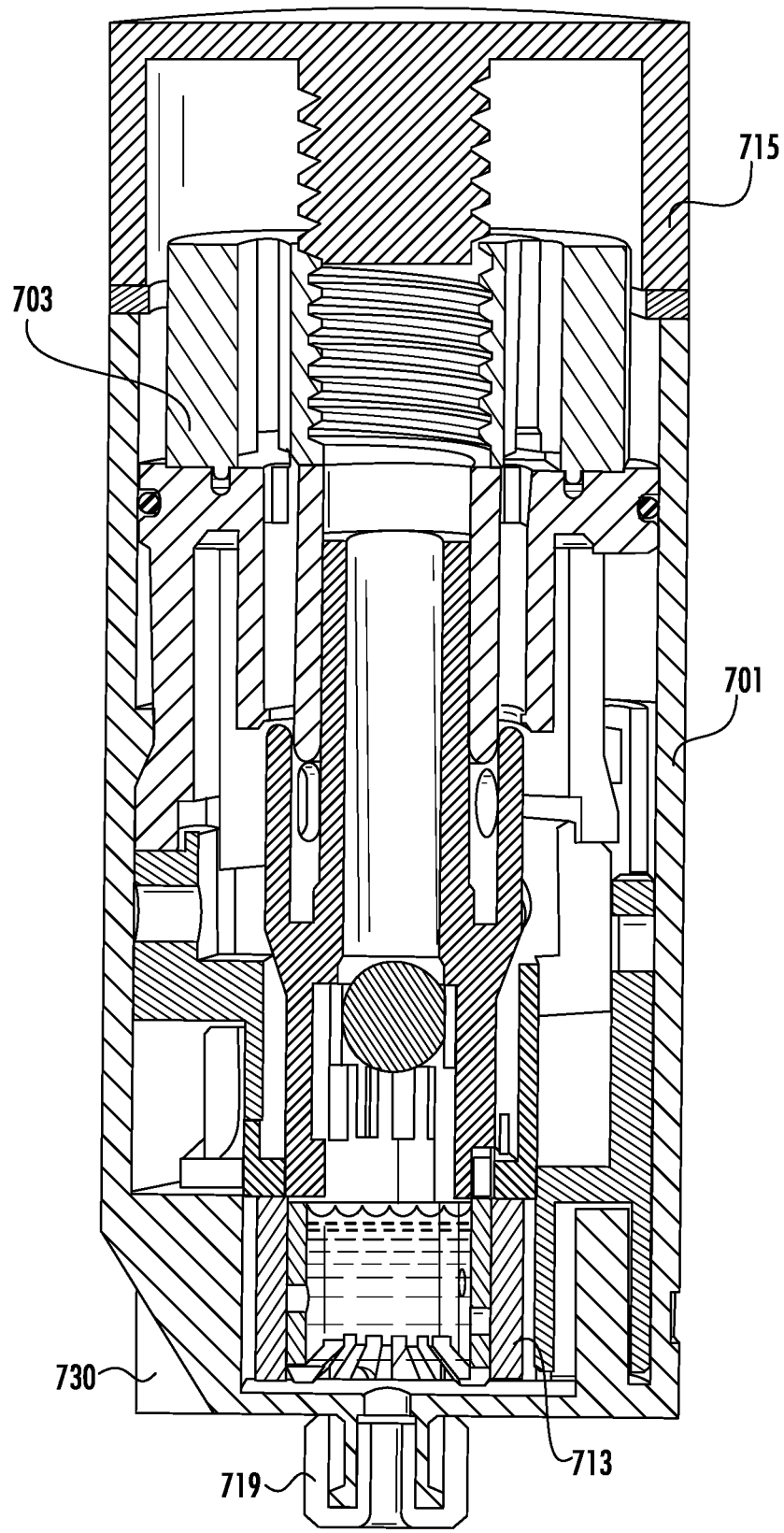

Referring now to FIG. 7B, the example method for operating an example aerosol collection device in accordance with examples of the present disclosure comprises disconnecting the aerosol collection device from the upper plunger component 703 of the device body 701 and connecting/reconnecting the cap component 715 to the upper plunger component 703 of the device body 701 to seal the device body 701.

As described above, the upper plunger component 703 comprises a plunger head element defining a central bore having threads on the inner surface, and the cap component 715 comprises an extended portion having threads on the outer surface. The extended portion of the cap component 715 may be fasten to the central bore of the plunger head element of the upper plunger component 703 through threads. In some embodiments, the cap component 715 is configured to seal the flow channel.

Figure 7C:
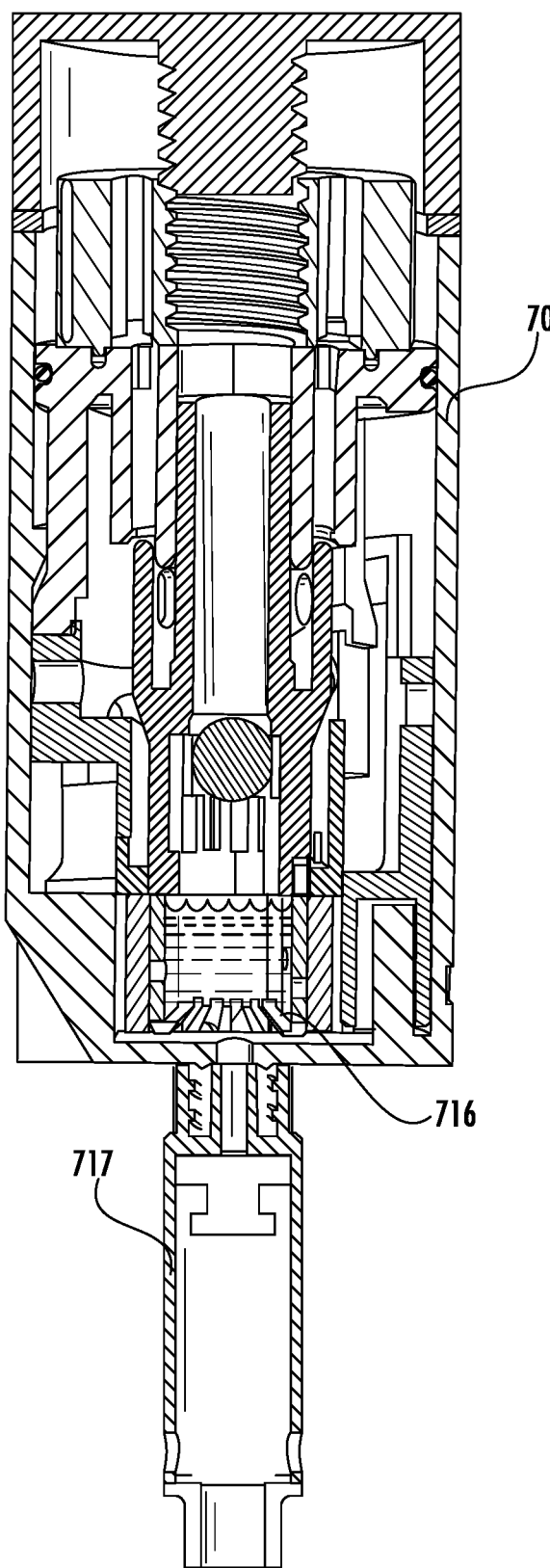

Referring now to FIG. 7C, the example method for operating an example aerosol collection device in accordance with examples of the present disclosure comprises connecting a extraction cartridge 717 to the device body 701.

In some embodiments, the device body 701 comprises a lock component 719 sealing a bottom hole of the device body 701. In some embodiments, the lock component 719 prevents contamination. In some embodiments, connecting the extraction cartridge 717 comprises disconnecting the lock component 719 from a bottom of the vessel component 730 shown in FIG. 7B and connecting the extraction cartridge 717 to an opening on the bottom of the vessel component 730 (after the lock component 719 is removed), details of which are described herein. In some embodiments, the opening on the bottom of the vessel component 730 (after the lock component 719 is removed) may be connected to an inlet (for example, an inlet of a waveguide cartridge) for further diagnostics.

Figure 7D:
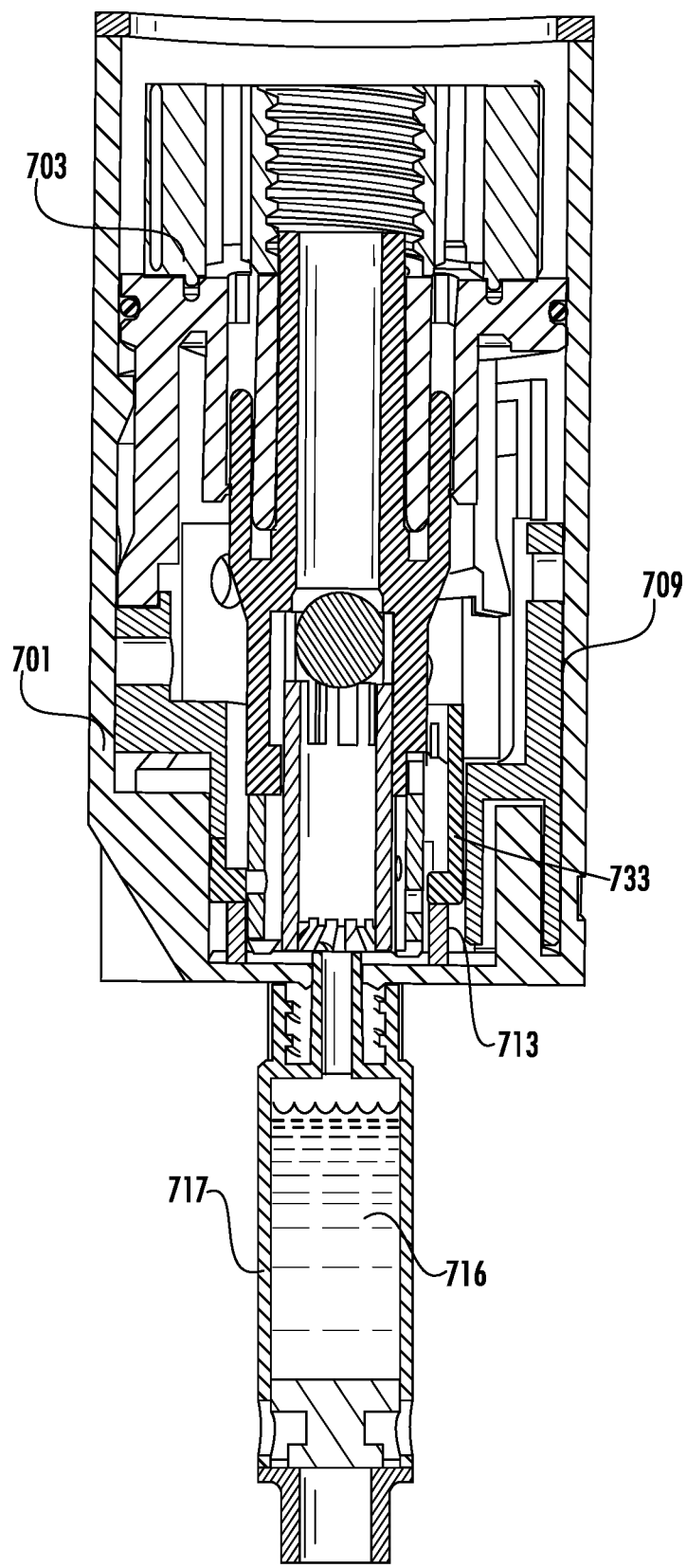

Referring now to FIG. 7D, the example method for operating an example aerosol collection device in accordance with examples of the present disclosure further comprises exerting a rotational force on the upper plunger component 703, causing the upper plunger component 703 to translate from a first configuration to a second configuration. In the first configuration, a bottom surface of the upper plunger component 703 is in contact with a top surface of the at least one capsule component 709. In the second configuration, the bottom surface of the upper plunger component 703 is in contact with a top surface of a lower plunger component 733.

In some embodiments, the example method for operating an example aerosol collection device in accordance with examples of the present disclosure further comprises exerting a vertically downward force on a top surface of the upper plunger component 703, which in turn causes the lower plunger component 733 to press on the filter component 713, thereby squeezing the sample liquid out of the filter component 713.

In some embodiments, the example method for operating an example aerosol collection device in accordance with examples of the present disclosure comprises extracting the buffer solution 716 from the device body 701 to the extraction cartridge 717, details of which are described herein.

Figure 7E:
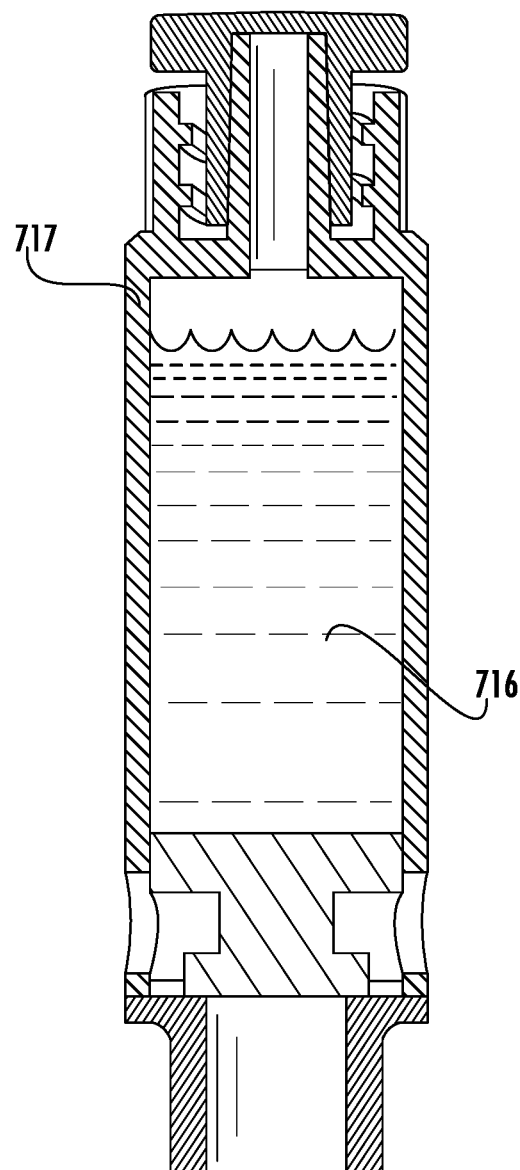

Referring now to FIG. 7E, the example method for operating an example aerosol collection device in accordance with examples of the present disclosure comprises disconnecting the extraction cartridge 717 from the device body 701. In some embodiments, the extraction cartridge 717 stores the buffer solution 716 containing aerosols that has been extracted from the device body 701. In some embodiments, the buffer solution 716 comprising aerosols captured from the sample may be provided to downstream diagnostics for detecting pathogen in the sample. For example, the buffer solution 716 comprising aerosols captured from the sample may be provided to a waveguide (such as, but not limited to, a waveguide cartridge) for further analysis and downstream diagnostics.

As such, in accordance with various examples of the present disclosure, an example aerosol collection device and example methods associated with the aerosol collection device are provided. In some embodiments, the aerosol collection device may function as an aerosol collector utilizing a wet filter-based capture system. In some embodiments, buffer solution is contained in capsule component(s) that are perforated before the sample is collected. In some embodiments, the aerosol collection device is self-contained and single use. In some embodiments, the use intent of the aerosol collection device is designed into the aerosol collection device so as to reduce user errors in using the aerosol collection device.

In some embodiments, prior to using the aerosol collection device, the aerosol collection device is sealed with the cap component secured. In some embodiments, the cap component is removed and a sample transfer adapter (such as, but not limited to, mask, straw or hood connector) is screwed into the aerosol collection device. In some embodiments, the aerosol collection device is pressed down, which presses the capsule component down onto an capsule extraction body element, liberating the buffer solution onto a filter component. In some embodiments, the sample is taken through the sample transfer adapter and passes through the wetted filter. Once this is completed, in some embodiments, the sample transfer adapter is removed, and the cap component is reattached to the aerosol collection device, which seals the aerosol collection device. Subsequently, the sample is extracted from the aerosol collection device.

Referring now to FIG. 8 to FIG. 14B, an example aerosol collection device 800 in accordance with example embodiments of the present disclosure is illustrated.

Figure 8:
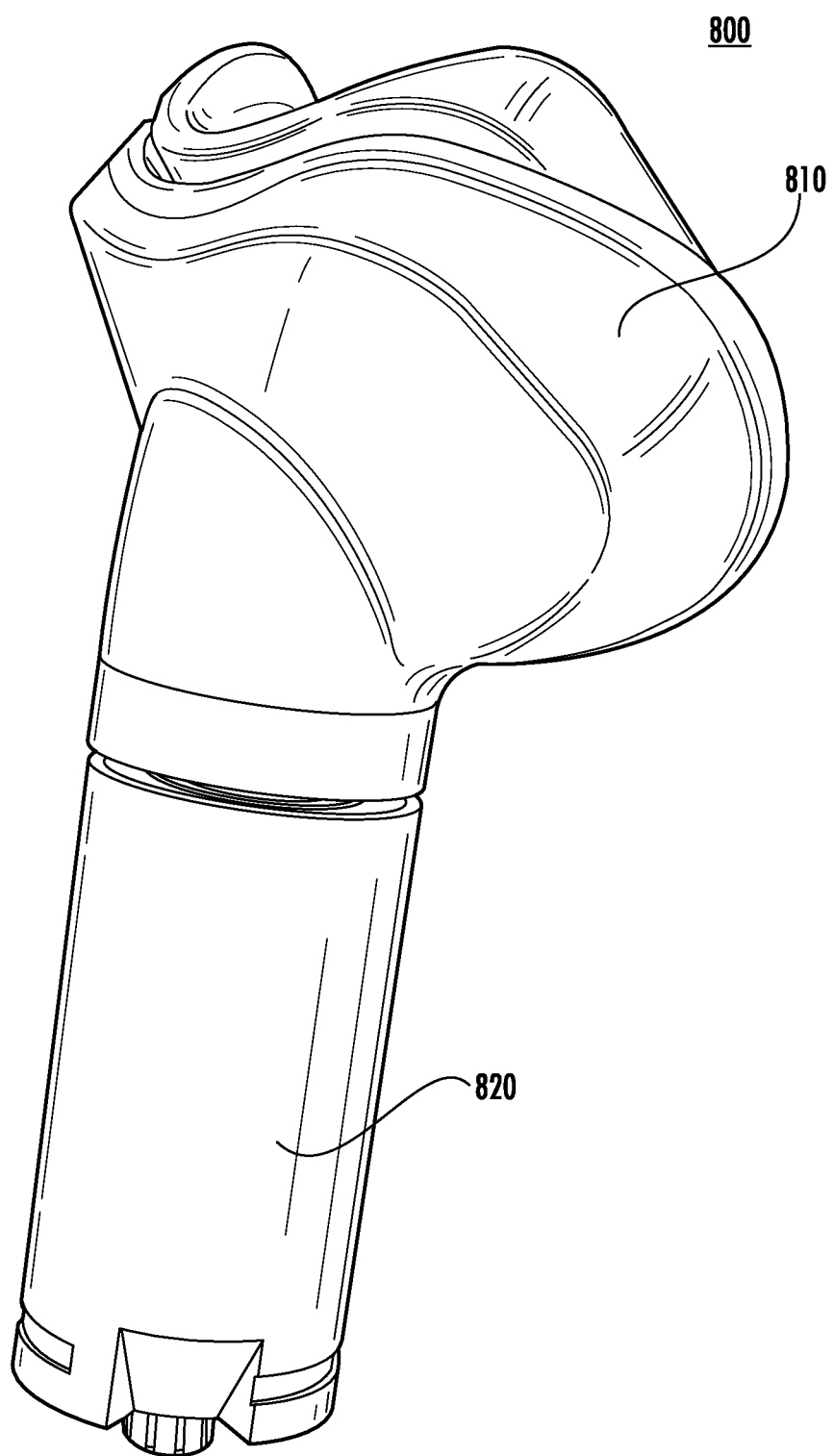
FIG. 8 illustrates an example view of an example aerosol collection device in accordance with various examples of the present disclosure.

Referring now to FIG. 8, an example view of the example aerosol collection device 800 is illustrated. In the example shown in FIG. 8, the example aerosol collection device 800 may comprise a sample transfer adapter and a device body. As illustrated, the sample transfer adapter may comprise a mask component 810 configured to attach to a device body 820.

In various embodiments, a mask component 810 may comprise a facial interface element, an exterior shell, an interior cavity, and a sampling channel. As illustrated in FIG. 8, mask component 810 comprises a facial interface element 811, a mask exterior shell 812, a mask interior cavity 813, and a sampling channel 814. In various embodiments, the mask component 810 may comprise a mask exterior shell 812 that defines at least a portion of the structural exterior of the mask component 810 and a facial interface element 811 including one or more contoured surfaces arranged about a portion of the mask exterior shell 812 and defining an opening therein. For example, the one or more contoured surfaces of the facial interface element 811 may be configured to engage a portion of a face of a user. In particular, the one or more contoured surfaces of the facial interface element 811 may be configured to be pressed against a portion of the user's face that surrounds the user's mouth and/or nose such that the opening defined by the facial interface element 811 may be configured to receive the mouth and/or nose of the user. In such an exemplary circumstance, a user's mouth and/or nose is positioned within the opening defined by the facial interface element 811, and the one or more contoured surfaces of the facial interface element 811 may be configured such that an at least substantially air-tight seal may be present along the one or more contoured surfaces pressed against the user's face. As such, the mask component 810 may be configured such that a user's face being engaged with the facial interface element 811 (e.g., such that the user's mouth and/or nose is arranged within the opening defined by the facial interface element 811) may enable a user's mouth and/or nose to be in fluid communication with a mask interior cavity 813. For example, an air sample provided by a user (e.g., a breath or cough from the user) may be administered into the mask interior cavity 813 of the exemplary mask component 810 via the facial interface element 811. As described in further detail herein, in some embodiments, the sample may comprise air and aerosol (which may contain pathogen particles).

In various embodiments, the mask exterior shell 812 may comprise a substantially hollow exterior housing that at least partially defines a mask interior cavity 813 of the mask component 810. For example, the mask interior cavity 813 may comprise the interior volume within the mask exterior shell 812, as defined by the hollow configuration of the mask exterior shell 812. In various embodiments, the mask interior cavity 813 may be configured to receive an air sample though the opening defined by the facial interface element 811. For example, in an exemplary circumstance where the facial interface element 811 is engaged with the face of a user, the mask interior cavity 813 may be configured to receive a sample from the mouth and/or nose of the user (e.g., an exhaled breath) through the opening defined by the facial interface element 811. In various embodiments, the mask interior cavity 813 may be fluidly connected with the sampling channel 814 of the mask component 810, such that an air sample within the mask interior cavity 813 (e.g., a breath provided from the user) may further flow into the sampling channel 814 for delivery from the mask component 810 to the device body 820, as described in further detail herein.

In various embodiments, the sampling channel 814 of an exemplary mask component 810 may comprise a conduit element configured to facilitate the delivery of an air sample provided to the mask component 810 to a downstream component of the exemplary aerosol collection device 800. For example, in various embodiments described herein, the sampling channel 814 may be configured to facilitate the delivery of an air sample present within the mask interior cavity 813 to a device body 820 (for example, into a flow channel described herein).

Figure 9:
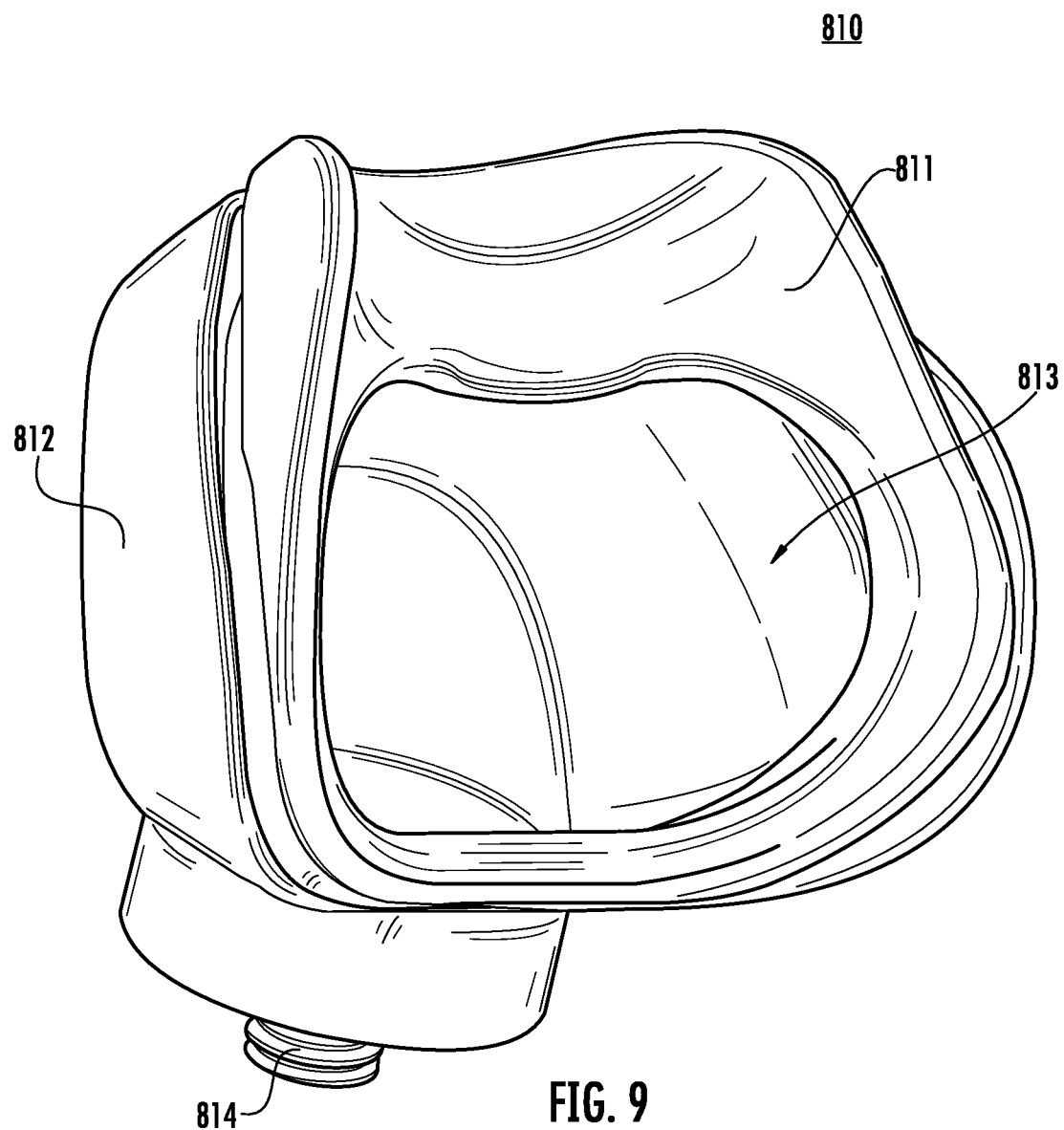
FIG. 9 illustrates an example view of an example sample transfer adapter in accordance with various examples of the present disclosure.
Figure 10:
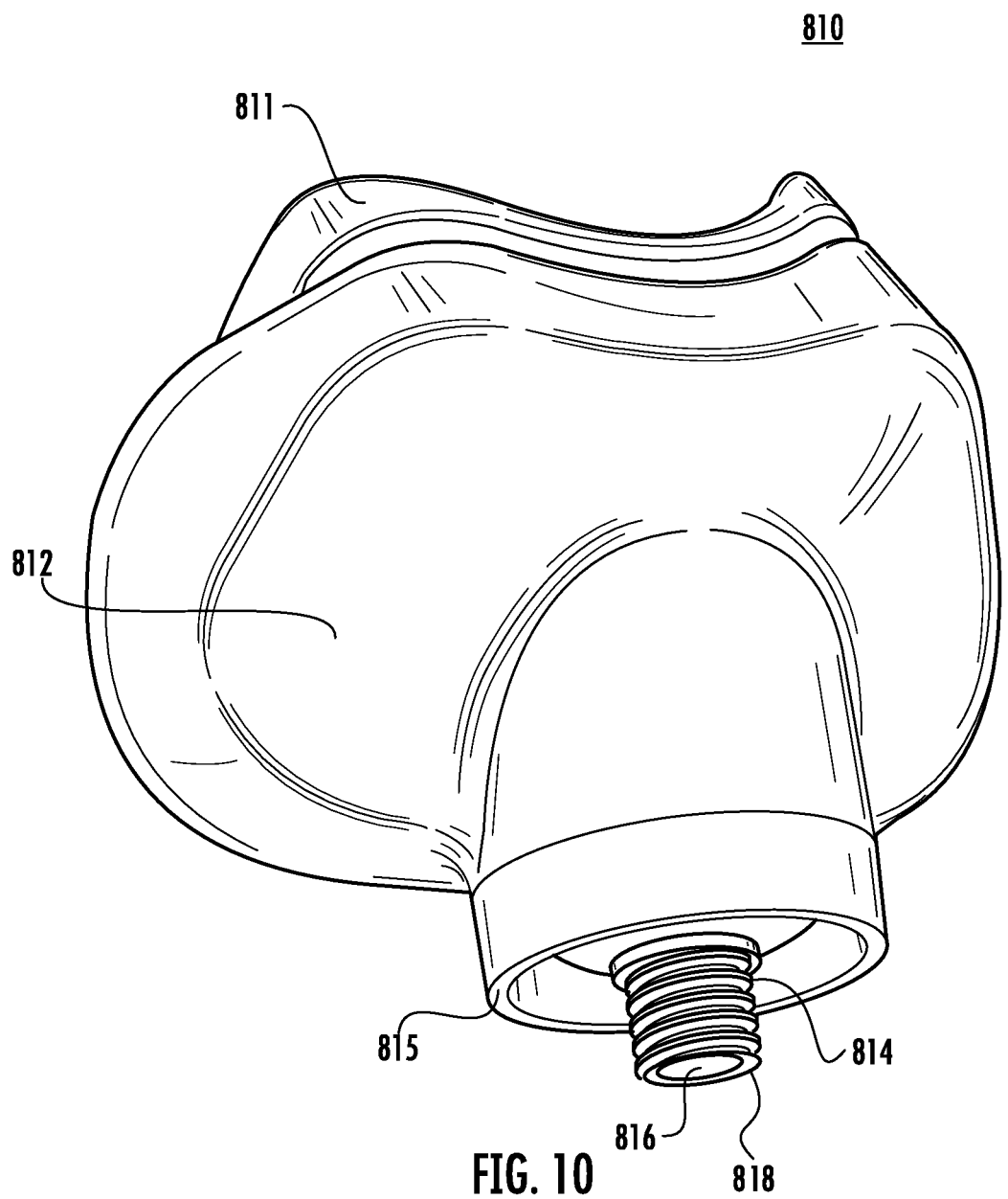
FIG. 10 illustrates an example view of an example sample transfer adapter in accordance with various examples of the present disclosure.
Figure 11:
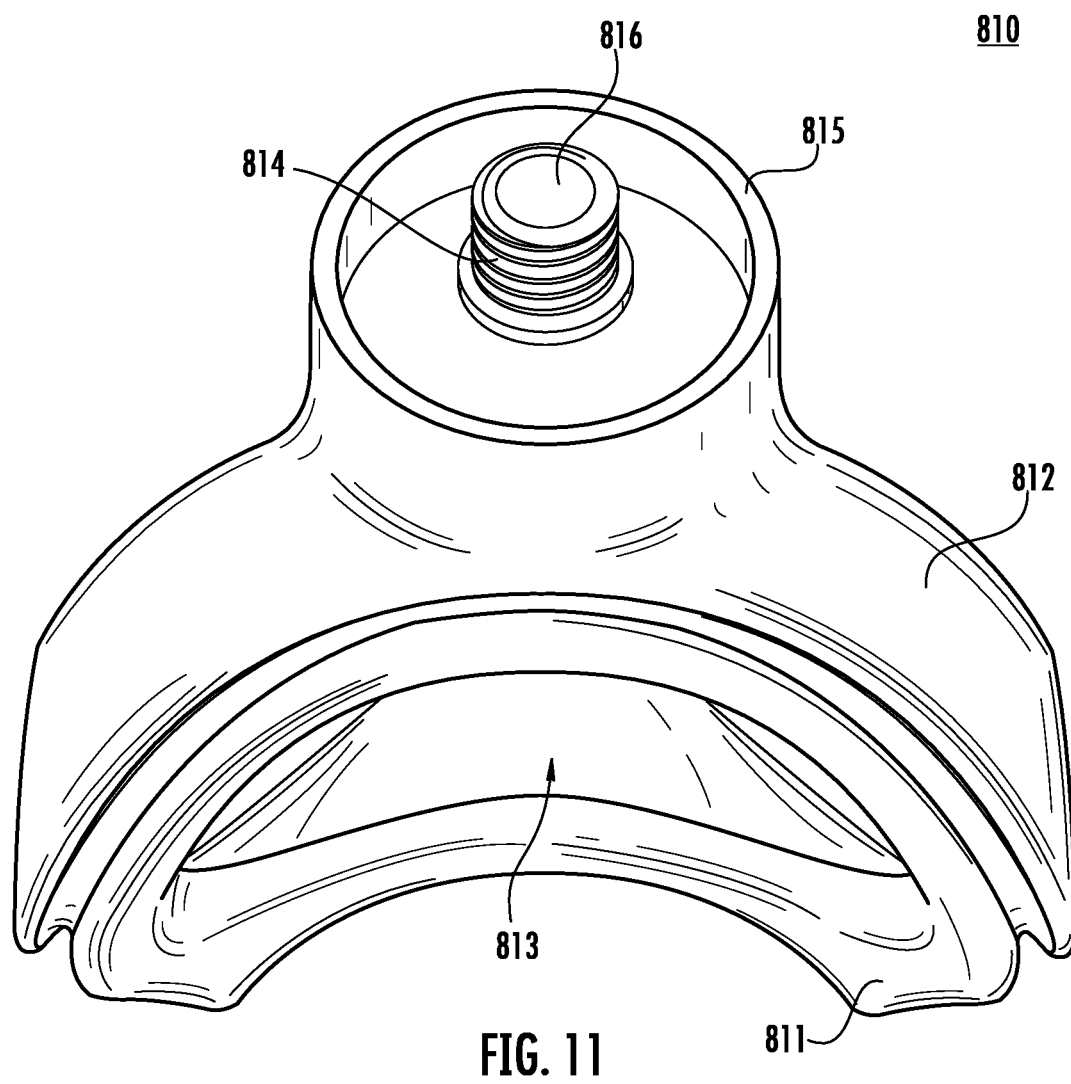
FIG. 11 illustrates an example view of an example sample transfer adapter in accordance with various examples of the present disclosure.
Figure 12B:
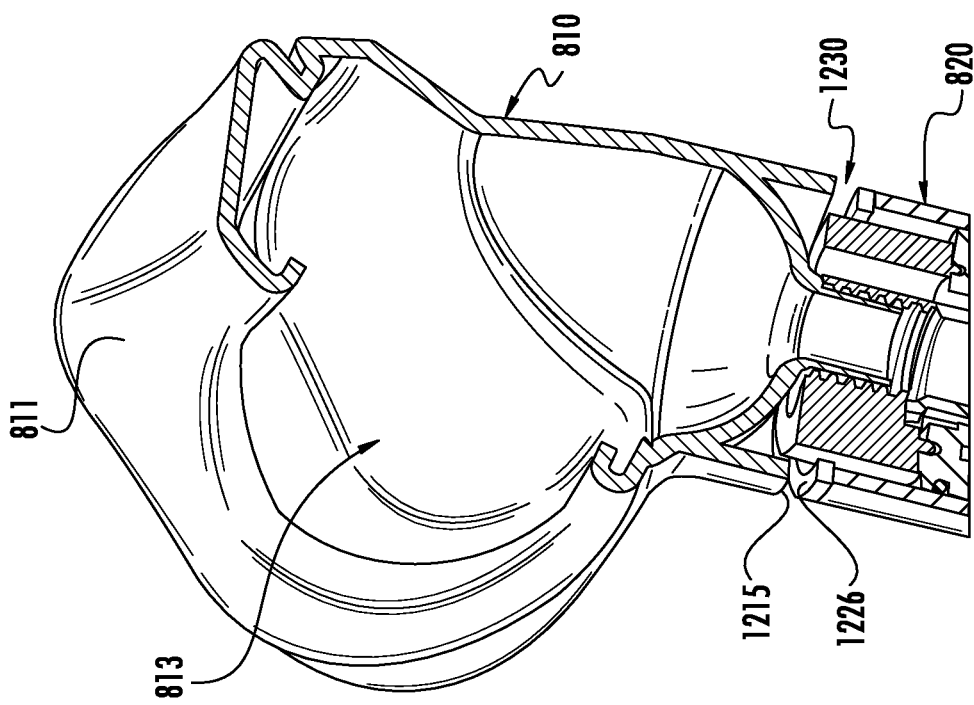
FIG. 12A and FIG. 12B illustrate example views of an example sample transfer adapter connected to an example device body in accordance with various examples of the present disclosure.
Figure 12A:
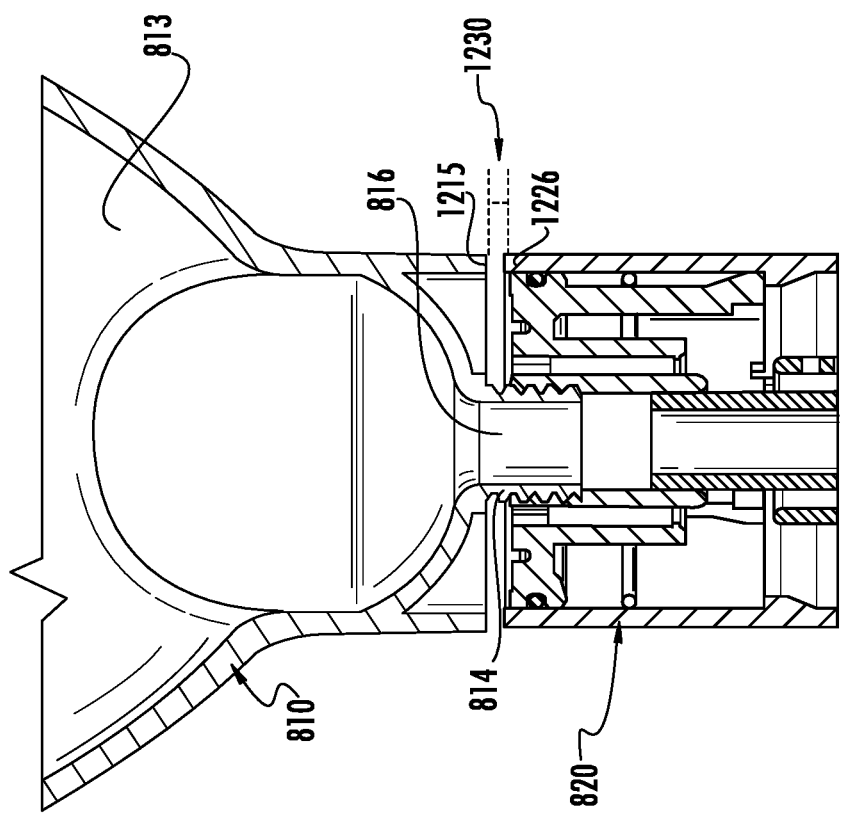

As illustrated in FIG. 9 and FIG. 10, the sampling channel 814 may comprise a tubular structure having a hollow central portion throughout the length of the structure that allows air to pass therethrough. In various embodiments, sampling channel 814 may comprise a first end that is arranged adjacent to and/or within the mask interior cavity 813, such that the sampling channel 814 is in fluid communication with the mask interior cavity 813 and configured to receive an air sample therefrom. Further, sampling channel 814 may comprise a second end at an opposite, distal end of the tubular structure. In various embodiments, at least a distal portion of the sampling channel, such as, for example, the second end of the sampling channel 814, may protrude from the mask exterior shell 812 in an outward direction so as to extend away from the surface of the mask exterior shell 812. In various embodiments, sampling channel 814 may further comprise a sample outlet 818 through which a sample traveling along the hollow interior of the sampling channel 814 may be dispensed therefrom. For example, the sample outlet 818 may be defined by an orifice positioned at the second end of the tubular structure of the sampling channel 814. As described herein, in various embodiments, the sample outlet 818 of the sampling channel 814 may embody a sample outlet of the mask component 810. In such an exemplary circumstance, a sample of air received by the mask component 810 may be dispensed from the mask component 810 to a fluidly downstream component of the aerosol collection device 800 (e.g., a flow channel of the device body 820) via the sample outlet 818.

In various embodiments, the sampling channel 814 may be attached to at least a portion of the device body 820 so as to secure the mask component 810 relative to the device body 820. For example, in some embodiments, the sampling channel 814 may be attached to a flow channel (e.g. defined by at least an upper plunger component) of the device body 820 via various means, including but not limited to, mechanical means (for example, the sampling channel 814 may be screwed into the device body 820 via threads provided about an exterior surface of the distal portion of the sampling channel 814). In various embodiments, the sampling channel 814 may be attached to the device body 820 such that an air flow path extending from the sample outlet 818 of the sampling channel 814 to the central bore of the device body 820, as described herein, may remain at least substantially unobstructed.

While the description above provides an example of the sampling channel 814, it is noted that the scope of the present disclosure is not limited to the description above. In some examples, the sampling channel 814 may be embodied as, such as but not limited to, an orifice extending through the mask exterior shell 812 that is configured to fluidly connect the mask interior cavity 813 to a downstream component of the aerosol collection device 800 (e.g., the device body 820) such that a sample present within the mask interior cavity 813 may flow through the orifice in the mask exterior shell 812 directly to the downstream component of the aerosol collection device 800. Further, in various embodiments, one or more components of an exemplary mask component 810 such as, for example, a sampling conduit 816 may be selectively removable from the mask exterior shell 812 of the mask component 810.

In various embodiments, the exemplary mask component 810 may comprise one or more adapter ventilation elements configured to enable a volume of air dispensed from an exhaust outlet of a device body 820 coupled to the mask component 810 (for example, from an opening/vent port of a plunger head element of the upper plunger component described herein) to flow into the ambient environment. For example, the mask exterior shell 812 of an exemplary mask component 810 may be defined in part by a mask ventilation surface 815. In various embodiments, a mask ventilation surface 815 may be configured such that, in an exemplary circumstance where the sampling channel 814 of the mask component 810 is attached to device body 820 (e.g., at a upper plunger component of device body 820), the mask ventilation surface 815 is positioned a distance away from the device body 820 so as to provide an opening (e.g., an adapter ventilation opening) between the mask component 810 and the device body 820 through which at least a portion of the aerosol-removed sample dispensed from an exhaust outlet of the device body 820 (for example, from an opening/vent port of a plunger head element of the upper plunger component described herein) may be exhausted into the ambient environment. As illustrated further in FIG. 12A and FIG. 12B, the exemplary mask component 810 may be configured such that the mask exhaust surface 1215 of the mask component 810 is positioned a perpendicular distance away from an exterior surface 1226 of the device body 820 (e.g., an exterior surface of the aerosol collection device 800 through which air samples are dispensed through exhaust outlets) so as to provide a ventilation opening 1230 through which at least a portion of the aerosol-removed sample dispensed from exterior surface 1226 may be exhausted into the ambient environment. As described herein, prior to being dispensed from the aerosol collection device 800, the sample may travel along the vent channel and through the filter element in the upper plunger component. As such, aerosols may be removed from the sample by the filter element prior to being released into the ambient environment.

While the description above provides an example of the ventilation opening 1230 defined, at least in part, by the mask exhaust surface 1215, it is noted that the scope of the present disclosure is not limited to the description above. In some examples, the ventilation opening 1230 may be embodied as an adapter ventilation element of an exemplary mask component 810, the adapter ventilation element comprising one or more tubular channels configured to at least partially define an air flow path that extends between the exhaust outlet of the aerosol collection device 800 and the ambient environment so as to facilitate the delivery of an air sample exhausted from the aerosol collection device 800 to the ambient environment via the adapter ventilation channels.

While the description above provides an example of a sample transfer adapter as exemplary mask component 810, it is noted that the scope of the present disclosure is not limited to the description above. In some examples, the sample transfer adapter may be embodied as, such as but not limited to a sampling tunnel, sampling hood, and/or other device(s). In some embodiments, the sample transfer adapter may be in the form of a nasal swab that can provide biological samples.

For example, as illustrated in FIG. 13A and FIG. 13B, an exemplary aerosol collection device 1300 may comprise a sample transfer adapter embodied as a sampling tunnel 1310. In various embodiments, a sampling tunnel 1310 may be in the form of a tubular structure having a sample inlet 1311 configured to receive a sample from, for example, a user, and a sampling tunnel body 1312 configured to deliver the received sample from the sample inlet 1311 to a device body 1320 (to which the sampling tunnel 1310 may be attached). For example, the sampling tunnel body 1312 may be in a tube shape and/or comprise a hollow portion in the center that allows air to pass. In some embodiments, the sampling tunnel 1310 may be embodied as a breathing straw. As such, sample (for example, breath from a user) may be administered into the example device body 1320 via the sampling tunnel 1310.

In various embodiments, sampling tunnel 1310 may be configured to be attached to an exemplary device body 1320 via a means at least substantially similar to that of the exemplary mask component 810 described above. Further, in various embodiments, the exemplary sampling tunnel 1310 may comprise one or more adapter ventilation elements configured to enable a volume of air dispensed from an exhaust outlet of a device body 1320 (for example, from an opening/vent port of a plunger head element of the upper plunger component described herein) coupled to the sampling tunnel 1310 to flow into the ambient environment. For example, sampling tunnel 1310 may comprise a sampling tunnel ventilation surface 1315. In various embodiments, the sampling tunnel ventilation surface 1315 may be configured such that, in an exemplary circumstance where the sampling tunnel 1310 is attached to a device body 1320, as described herein, the sampling tunnel ventilation surface 1315 is positioned a distance away from the device body 1320 so as to provide an opening (e.g., an adapter ventilation opening) between the sampling tunnel 1310 and the device body 1320 through which at least a portion of the aerosol-removed sample dispensed from an exhaust outlet of the device body 1320 1320 (for example, from an opening/vent port of a plunger head element of the upper plunger component described herein) may be exhausted into the ambient environment. As illustrated in FIG. 13A and FIG. 13B, the exemplary sampling tunnel 1310 may be configured such that the sampling tunnel ventilation surface 1315 is positioned at a perpendicular distance away from an exterior surface 1326 of the device body 1320 (e.g., an exterior surface of the device body 1320 through which air samples are dispensed through exhaust outlets) so as to provide an adapter ventilation opening 1330 through which at least a portion of the aerosol-removed sample dispensed from exterior surface 1326 may be exhausted into the ambient environment.

As another example, FIG. 14A and FIG. 14B illustrate an exemplary aerosol collection device 1400 comprising a sample transfer adapter embodied as a sampling hood 1410. In various embodiments, a sampling hood 1410 may define a sampling channel 1414 having a sample inlet 1411 configured to receive a sample from, for example, a user. The sampling channel 1414 may be embodied as a tubular structure configured to deliver the received sample from the sample inlet 1411 to a device body 1420 to which the sampling channel 1414 may be attached. For example, the sampling channel 1414 may be in a tube structure and/or comprise a hollow portion in the center that allows air to pass. In various embodiments, sampling channel 1414 may further comprise a sampling channel outlet 1416 through which a sample traveling along the hollow interior of the sampling channel 1414 may be dispensed therefrom. For example, the sampling hood outlet 1417 may be defined by an orifice positioned at an opposite end of the tubular structure of the sampling channel 1414 relative to the sample inlet 1411. In various embodiments, a sample of air received by the sampling hood 1410 may be dispensed from the sampling hood 1410 to a fluidly downstream component of the aerosol collection device 1400 (e.g., a flow channel of the device body 1420) via the sampling channel outlet 1416.

In various embodiments, sampling hood 1410 may be configured to be attached to an exemplary device body 1420 via a means at least substantially similar to that of the exemplary mask component 810 and/or the sampling tunnel 1310 described above. Further, in various embodiments, the exemplary sampling hood 1410 may comprise one or more adapter ventilation elements configured to enable a volume of air dispensed from an exhaust outlet of a device body 1420 coupled to the sampling hood 1410 to flow into a downstream environment fluidly connected thereto. For example, sampling hood 1410 may comprise a hood cover 1412 embodied as a substantially hollow shell housing that at least partially defines a hood interior cavity 1413 of the sampling hood 1410. For example, the hood interior cavity 1413 of the sampling hood 1410 may comprise at least a portion of the interior volume within the hood cover 1412, as defined by the hollow configuration of the hood cover 1412. In various embodiments, the sampling hood 1410 may comprise a sampling hood outlet 1417 through which a sample received within the hood interior cavity 1413 may flow so as to be dispensed from the sampling hood 1410. For example, sampling hood outlet 1417 may be an orifice extending through the hood cover 1412 that is configured to fluidly connect the hood interior cavity 1413 to a downstream environment connected to the sampling hood outlet 1417 such that an air sample within the hood interior cavity 1413 (e.g., a sample dispensed from the device body 1420) may flow through the sampling hood outlet 1417 to the downstream environment (for example, a flow channel).

In various embodiments, the hood interior cavity 1413 may be configured to receive a volume of air dispensed from an exhaust outlet of a device body 1420. For example, in an exemplary circumstance where the sampling hood 1410 is attached to a device body 1420 (e.g., via an attachment means at a distal end of the sampling channel 1414), the hood interior cavity 1413 may be configured to receive a sample dispensed from an exhaust outlet of the device body 1420. As illustrated in FIG. 14A and FIG. 14B, the hood cover 1412 may comprise a hood cover seal surface 1415 configured to engage a surface of a device body 1420 so as to generate an at least substantially air-tight seal between the sampling hood 1410 and a device body 1420 along the hood cover seal surface 1415. For example, the sampling hood 1410 may be configured such that, in an exemplary circumstance where the sampling channel 1414 of the sampling hood 1410 is attached to a device body 1420 (e.g., at a upper plunger component of device body 1420), the hood cover seal surface 1415 is physically engaged with one or more exterior surfaces 1426 of the device body 1420 (e.g., an exterior surface of the device body 1420 through which air samples are dispensed through vent channels) to provide a sealed perimeter about the one or more exterior surfaces 1426 of the device body 1420. The hood cover seal surface 1415 may be configured to prevent the sample dispensed from the device body 1420 (e.g., via one or more vent channels arranged about an exterior surface 1426) from flowing directly into an ambient environment without passing through at least a portion of the sampling hood 1410 (e.g., the sampling hood outlet 1417). For example, as illustrated in FIG. 14B, the sampling hood 1410 may be attached to the device body 1420 such that the sealed perimeter provided by the hood cover seal surface 1415 extends along the exterior surface 1426 so as to surround each of the one or more outlets of one or more vent channels of the device body 1420 (for example, surrounding one or more openings/vent ports of a plunger head element of the upper plunger component described herein). In such an exemplary configuration, the sampling hood 1410 may be configured such that the entirety of the sample dispensed from the device body 1420 (e.g., via the one or more vent channels) is received by the hood interior cavity 1413 and directed toward the sampling hood outlet 1417.

In various embodiments, a portion of hood cover 1412 at least substantially adjacent the sampling hood outlet 1417 may be configured to mechanically attach to one or more external components defining one or more downstream environments. For example, the hood cover 1412 may be configured to mechanically attach to an external component defining a downstream controlled environment in order to fluidly connected the sampling hood outlet 1417 to the downstream controlled environment. In such an exemplary circumstance, the sampling hood outlet 1417 may be configured to fluidly connect the hood interior cavity 1413 to the downstream controlled such that a sample dispensed from the device body 1420 into the hood interior cavity 1413 may further flow through the sampling hood outlet 1417 to the downstream controlled environment. In various embodiments, a controlled environment may exhibit one or more predefined environmental conditions, such as, for example, a known pressure, temperature, volume, aerosol composition, and/or the like. For example, a controlled environment disposed downstream from the sampling hood outlet 1417 may be utilized to enable the experimentation, observation, and/or analysis of a sample of air dispensed from the device body 1420 in a controlled environment.

Various embodiments the present disclosure may provide technical advantages and benefits in sample collection, such as, but not limited to, breath-aerosol collection. As described above, an example aerosol collection device in accordance with examples of the present disclosure may comprise a buffer solution. In some embodiments, the buffer solution may be tailored to specific subsequent pathogen detection techniques.

When a specimen is collected with nasal swabs, it requires an intermediate steps to extract the pathogen from the swab into a liquid medium. The liquid medium may be a buffered solution but the exact makeup of the medium differs depending on the immediate plans for the sample. For example, a stabilization medium can be used if the sample is going to be transferred via mail or stored before analysis. If the sample is going to be analyzed immediately (for example, within a few hours), the medium can contain chemicals meant to extract and preserve the RNA/DNA context for PCR-type assays.

In accordance with examples of the present disclosure, implementing the aerosol collection device may eliminate the need for nasal swabs, and the physics of the aerosol collection device is not impacted by the additional chemical constituents of the liquid medium. For example, specific liquid media for specific downstream analysis may be used as the buffer solution. Various embodiments of the present disclosure may combine the specimen collection step with the pathogen extraction step, which may save additional labor and reduce the risk of contamination of the specimen. In some embodiments, different liquids may be stored in a set of capsule components in a single aerosol collection device so that the liquids may be combined and react at the moment of use.

Figure 15A:
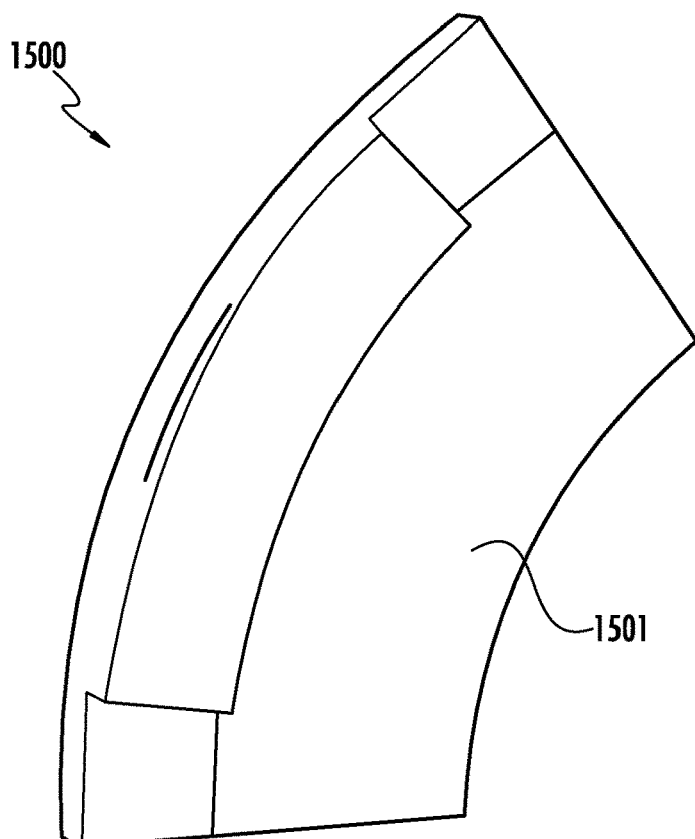
FIG. 15A, FIG. 15B, FIG. 15C, and FIG. 15D illustrate example views of an example capsule component in accordance with various examples of the present disclosure.
Figure 15B:
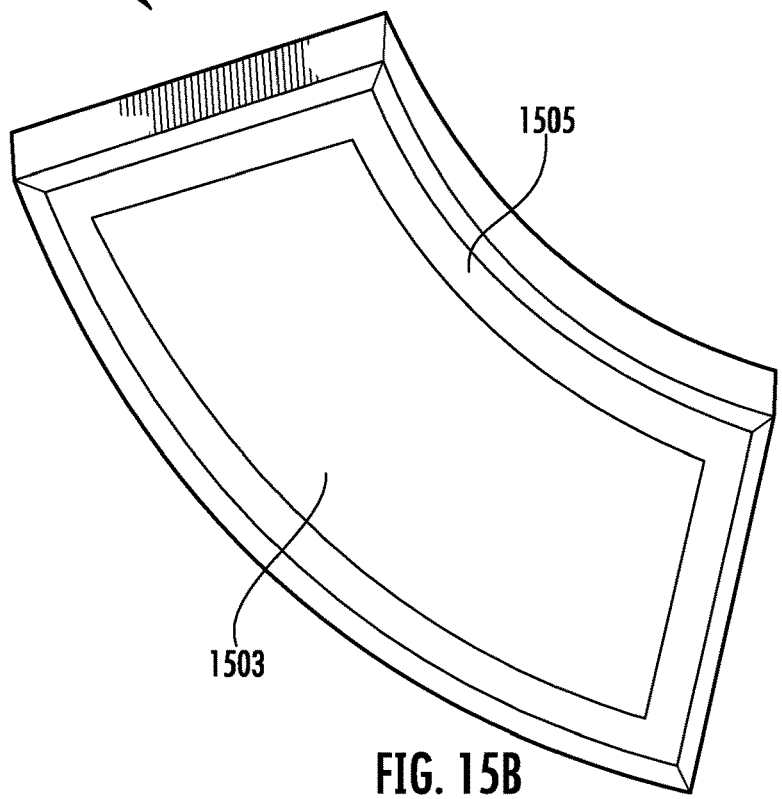
Figure 15D:
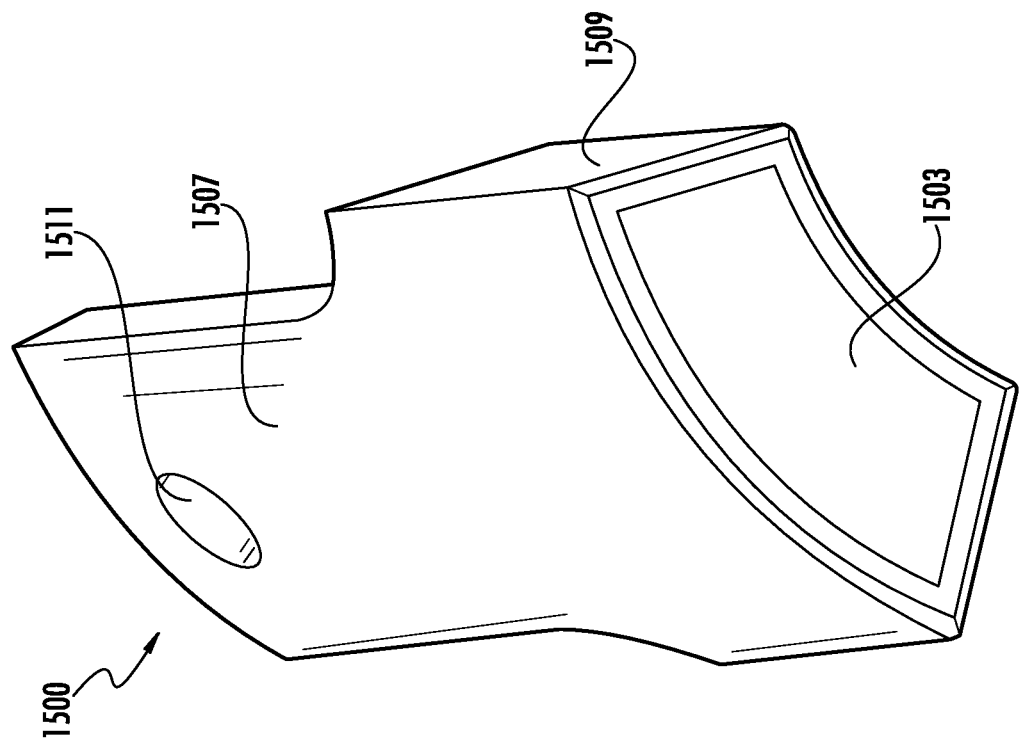
Figure 15C:
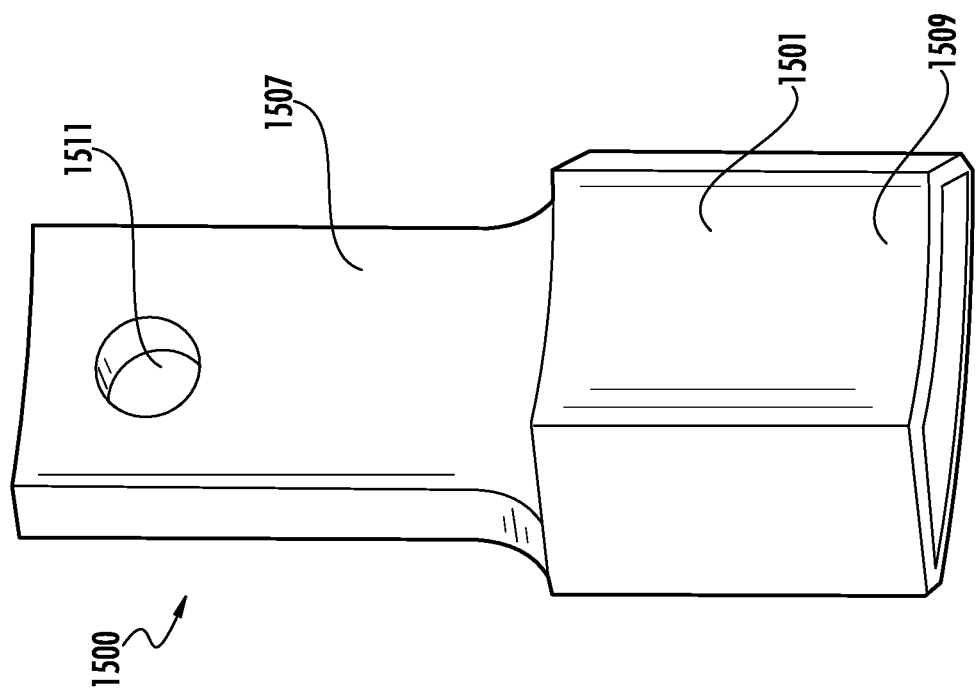
Figure 16:
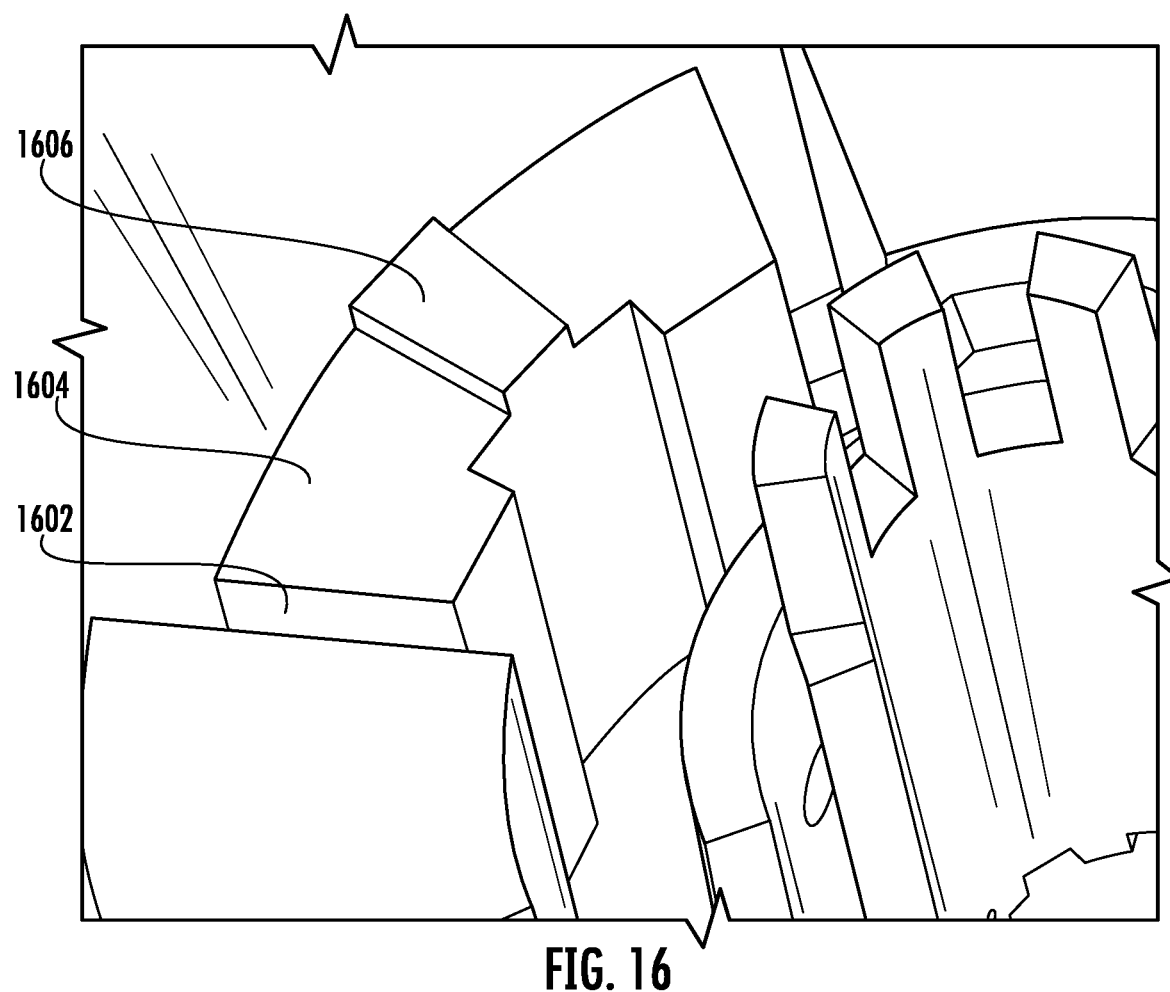
FIG. 16 illustrates an example view of at least a portion of an example capsule extraction body element in accordance with example embodiments of the present disclosure.
Figure 17B:
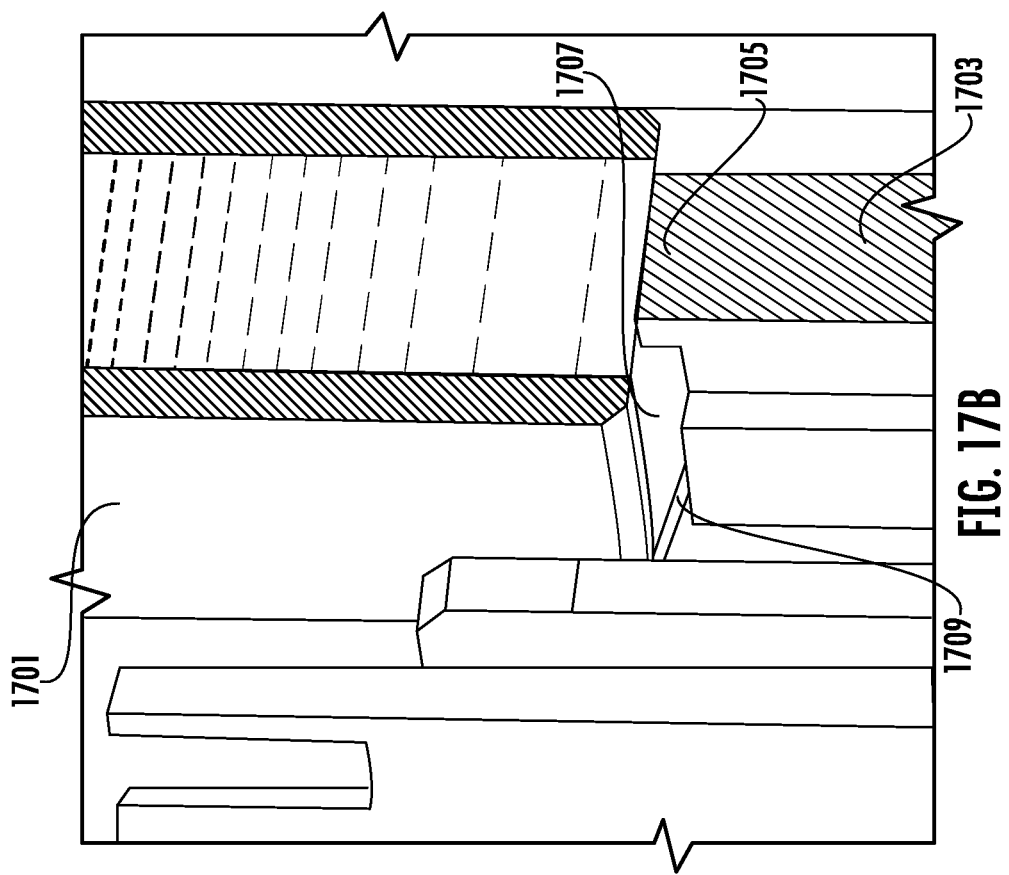
FIG. 17A and FIG. 17B illustrate example views of at least a portion of an example capsule component and an example capsule extraction body element in accordance with example embodiments of the present disclosure.
Figure 17A:
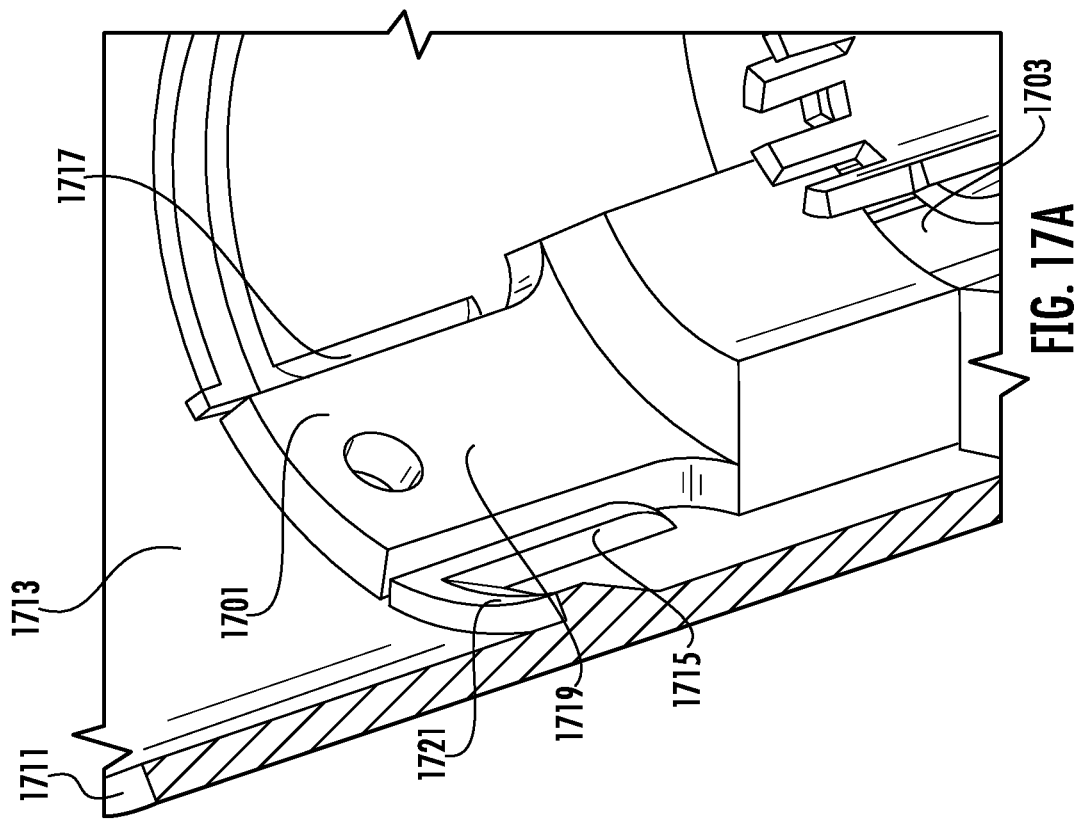
Figure 19:
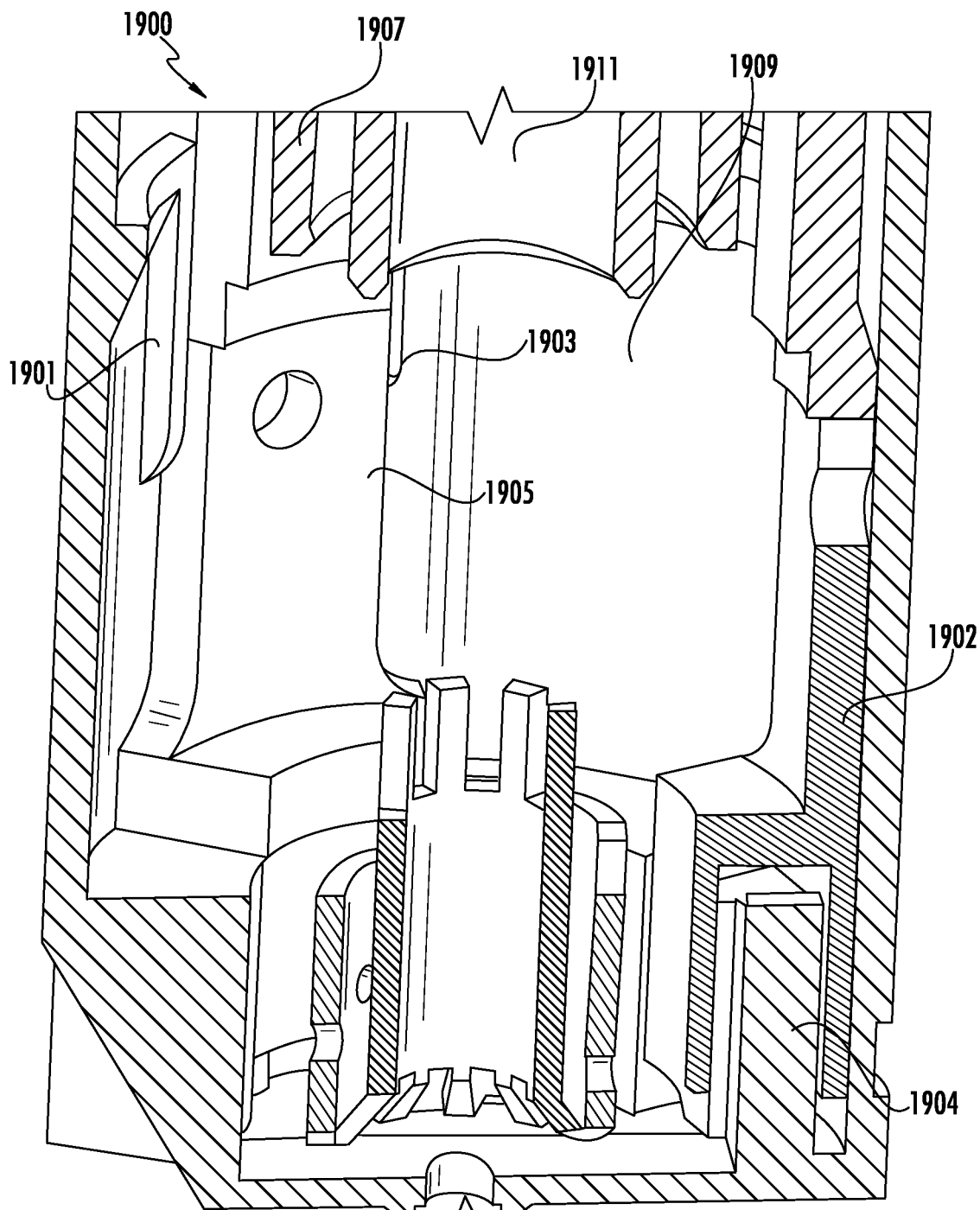
FIG. 19 illustrates an example view of an example aerosol collection device in accordance with examples of the present disclosure.
Figure 20:
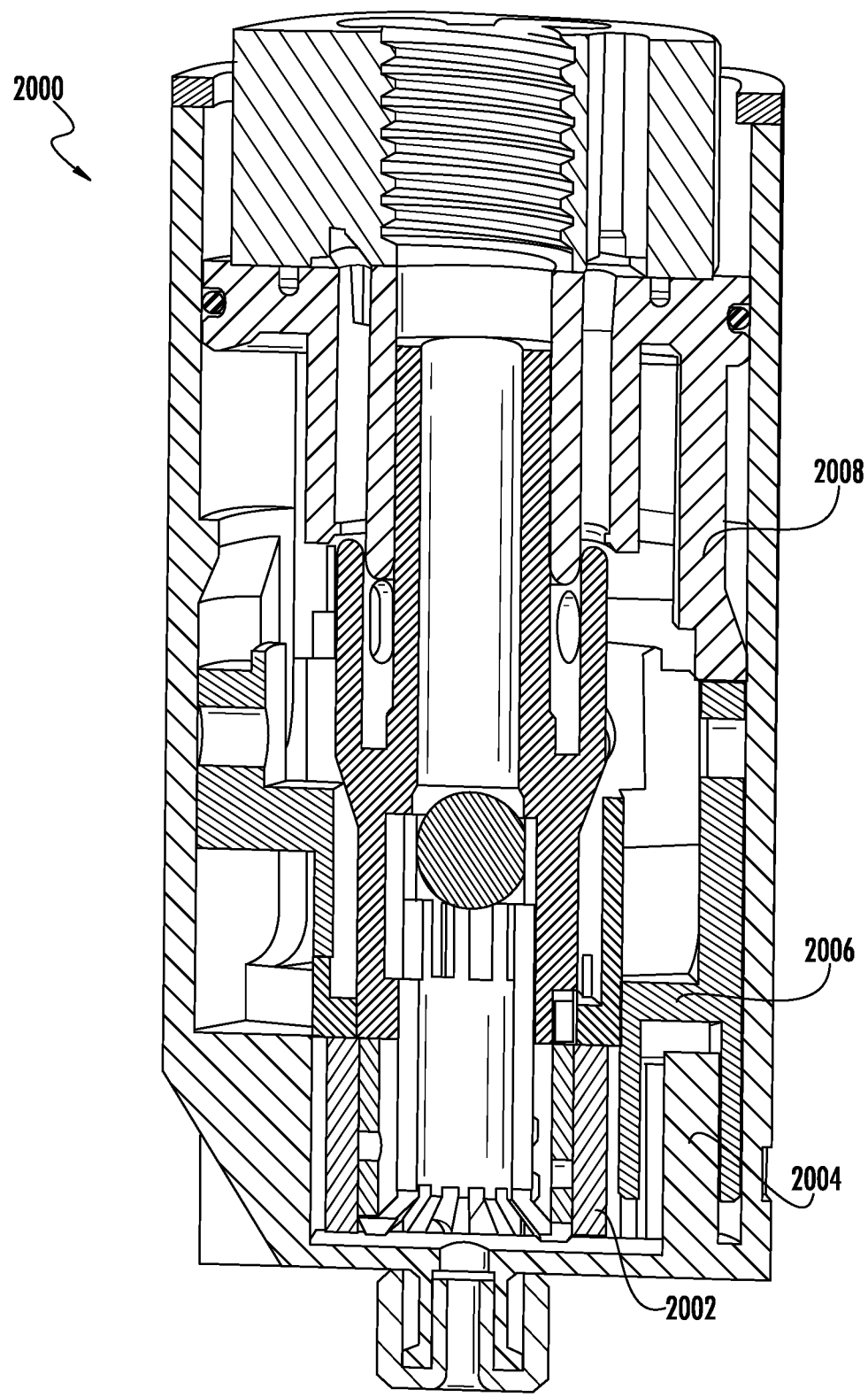
FIG. 20 illustrates an example view of an example aerosol collection device in accordance with examples of the present disclosure.

FIG. 15A, FIG. 15B, FIG. 15C, and FIG. 15D illustrate example views of an example capsule component 1500 in accordance with various examples of the present disclosure. In particular, FIG. 15A illustrates an example top view of the example capsule component 1500. FIG. 15B illustrates an example bottom view of the example capsule component 1500. FIG. 15C illustrates an example perspective view of the example capsule component 1500. FIG. 15D illustrates another example perspective view of the example capsule component 1500.

As shown in the example capsule component 1500 illustrated in FIG. 15A, FIG. 15B, FIG. 15C, and FIG. 15D, the example capsule component 1500 comprises a holder element 1501 and a cap element 1503.

In some embodiments, the buffer solution is hermetically sealed in the holder element 1501 by the cap element 1503. For example, the holder element 1501 defines a cavity having an opening on the bottom surface 1505 of the holder element 1501. In some embodiments, the buffer solution is disposed within the cavity defined by the holder element 1501. In some embodiments, the cap element 1503 seals the opening on the bottom surface 1505 of the holder element 1501.

In some embodiments, the cap element 1503 is attached to the holder element 1501 through a chemical adhesive, such as, but not limited to, a chemical glue. In some embodiments, the cap element 1503 is attached to the holder element 1501 through other means.

Referring now to FIG. 15C and FIG. 15D, the holder element 1501 may comprise a handle portion 1507 and a body portion 1509. In the example shown in FIG. 15C and FIG. 15D, the body portion 1509 stores the buffer solution. In some embodiments, the handle portion 1507 extends from a top surface of the body portion 1509.

In some embodiments, the handle portion 1507 may define an opening 1511. In some embodiments, after the aerosol collection device is used, a hook (such as a hex key) may be used to engage with the opening 1511 to pull the capsule component 1500 out from the aerosol collection device.

In some embodiments, an example aerosol collection device may comprise one or more capsule components. For example, the example aerosol collection device may comprise a first capsule component storing a first buffer solution and a second capsule component storing a second buffer solution. In some embodiments, the first buffer solution is the same as the second buffer solution. In some embodiments, the first buffer solution is different from the second buffer solution.

For example, the first buffer solution and/or the second buffer solution may contain chemicals that extract and/or preserve the genetic proteins collected from the sample. In some embodiments, the first buffer solution and/or the second buffer solution may contain chemicals that may assist the downstream analysis of the collected sample. In some embodiments, the first buffer solution and the second buffer solution may combine and react when they are released. In some embodiments, the buffer solution may have pH level(s) and ion concentration level(s) that are similar to human cells. In such embodiments, the buffer solution is a fluid that preserves biological samples.

In some embodiments, an example buffer solution may comprise two reagents that will interact with biological cells or proteins to produce either a color change or other property changes, indicating the presence of the target cells or proteins. Additionally, or alternatively, the capsule component may contain buffer solution for positive and negative controls that are targeted for biological elements for downstream analysis. For example, some buffer solutions may assist in identifying and/or detecting a biological element when there is a target virus in the sample. Additionally, or alternatively, some buffer solution may assist in identifying and/or detecting a biological element when there is no target virus in the sample. In some embodiments, some elements may contain the same positive and/or negative controls and, as such, the capsule component may contain different solutions. In some embodiments, a capsule component may store 0.7 milliliters of buffer solution. In some embodiments, the capsule component may store less than or more than 0.7 milliliters of buffer solution (for example, approximately 0.1 milliliters).

In some embodiments, an example aerosol collection device may comprise three capsule components: a first capsule component, a second capsule component, and a third capsule component. In some embodiments, the buffer solutions stored within each of the first capsule component, a second capsule component, and a third capsule component are the same. In some embodiments, two of the buffer solutions stored within each of the first capsule component, a second capsule component, and a third capsule component are the same. In some embodiments, the buffer solutions stored within each of the first capsule component, a second capsule component, and a third capsule component are different. In some embodiments, an example aerosol collection device may comprise less than or more than three capsule components.

FIG. 16 illustrates an example view of at least a portion of an example capsule extraction body element 1602 in accordance with example embodiments of the present disclosure. In the example shown in FIG. 16, the capsule extraction body element 1602 comprises a protrusion 1606 positioned on a top surface 1604 of the capsule extraction body element 1602.

FIG. 17A and FIG. 17B illustrate example views of at least a portion of an example capsule component 1701 and an example capsule extraction body element 1703 in accordance with example embodiments of the present disclosure.

As described above, an example aerosol collection device in accordance with examples of the present disclosure may comprise a capsule extraction body element 1703 and at least one capsule component (for example, a capsule component 1701). In some embodiments, the capsule component 1701 stores buffer solution, as described above. In some embodiments, the capsule component 1701 is positioned on the capsule extraction body element 1703.

In some embodiments, the aerosol collection device comprises a vessel component 1711 having an inner lateral surface 1713. In some embodiments, the vessel component 1711 comprises at least two vertical ridge elements disposed on the inner lateral surface 1713 of the vessel component 1711. In the example shown in FIG. 17A, the example vessel component 1711 comprises a first vertical ridge element 1715 and a second vertical ridge element 1717.

In some embodiments, at least a portion of each of the at least one capsule component is positioned between the at least two vertical ridge elements. In the example shown in FIG. 17A, a handle portion 1719 of the capsule component 1701 is positioned between the first vertical ridge element 1715 and the second vertical ridge element 1717. As such, in some embodiments, the first vertical ridge element 1715 and the second vertical ridge element 1717 secure the position of the capsule component 1701 and prevent the capsule component 1701 from sliding along the inner lateral surface 1713 of the vessel component 1711.

In some embodiments, the vessel component 1711 comprises at least one horizontal ridge element (for example, a horizontal ridge element 1721) disposed on the inner lateral surface 1713 of the vessel component 1711. In some embodiments, at least a top surface of each of the at least one capsule component is on a same plane as a top surface of the at least one horizontal ridge. In the example shown in FIG. 17A, a top surface of the capsule component 1701 (e.g. a top surface of the handle portion 1719 of the capsule component 1701) is on a same plane as a top surface of the horizontal ridge element 1721.

In the example shown in FIG. 17B, the capsule extraction body element 1703 comprises a protrusion 1705 extending from the top surface of the capsule extraction body element 1703. In some embodiments, the cap element 1707 of the capsule component 1701 is positioned on top of the protrusion 1705. Because the protrusion 1705 extends from the top surface of the capsule extraction body element 1703, only a portion of the cap element 1707 is in contact with the protrusion 1705 of the capsule extraction body element 1703, and an air gap 1709 is formed between the top surface of the capsule extraction body element 1703 (other than the protrusion 1705) and the cap element 1707 of the capsule component 1701.

Various embodiments of the present disclosure may provide various technical advantages and benefits. For example, an example aerosol collection device in accordance with examples of the present disclosure may comprise at least one capsule component. In some embodiments, the at least one capsule component is engaged and punctured during operation of the aerosol collection device to provide liquid insertion to a filter component at the moment of use, which may prevent prematurely providing the liquid insertion and may extend the shelf life of the aerosol collection device.

FIG. 18A and FIG. 18B each illustrates at least a portion of an example capsule component and/or a portion of an example upper plunger component in accordance with example embodiments of the present disclosure. In particular, FIG. 18A illustrates a bottom portion of the example upper plunger component 1803 and a top portion of a capsule component 1801. FIG. 18B illustrates a bottom portion of the capsule component 1801 and a top portion of capsule extraction body element 1805.

As described above, an example aerosol collection device in accordance with examples of the present disclosure may comprise at least one capsule component and an upper plunger component. In the example shown in FIG. 18A and FIG. 18B, the example aerosol collection device may comprise at least a capsule component 1801 and an upper plunger component 1803.

In some embodiments, the capsule component 1801 stores buffer solution. In some embodiments, a top surface of the capsule component 1801 is in contact with a bottom surface of the upper plunger component 1803 (for example, a bottom surface of the at least one leg portion), as shown in FIG. 18A.

As described above, the capsule component 1801 may comprise a holder element 1807 and a cap element 1809. In some embodiments, the holder element 1807 of the capsule component 1801 defines a cavity having an opening on a bottom surface of the capsule component 1801 and storing the buffer solution. In some embodiments, the cap element 1809 hermetically seals the opening of the holder element 1807.

In some embodiments, at least a portion of the cap element 1809 is in contact with the capsule extraction body element 1805. For example, a portion of the cap element 1809 is in contact with the protrusion 1813 of capsule extraction body element 1805, and an air gap 1811 is formed between the cap element 1809 and the top surface of the capsule extraction body element 1805, similar to those described above.

In some embodiments, the upper plunger component 1803 is in contact with a top surface of the holder element of the capsule component 1801 (for example, a top surface of a handle portion of the holder element).

In some embodiments, a vertically downward force may be exerted on a top surface of the upper plunger component 1803. The vertical force may be trigger by, for example, but not limited to, connecting an aerosol collection device to the upper plunger component 1803 as described above.

In some embodiments, in response to receiving a vertically downward force exerted on a top surface of the upper plunger component 1803, the upper plunger component 1803 is configured to transfer the vertically downward force to the capsule component 1801 and causing a vertical movement of the capsule component 1801. In some embodiments, the vertical movement of the capsule component 1801 causes the capsule extraction body element 1805 (for example, the protrusion 1813) to break the cap element 1809 of the capsule component 1801. Subsequent to the cap element 1809 being broken, the buffer solution that was stored in the holder element 1807 of the capsule component 1801 flows on the capsule extraction body element 1805. In some embodiments, the cap element 1809 may comprise material such as, but not limited to, polypropylene (for example, the cap element 1809 may be in the form of a polypropylene film). Additionally, or alternatively, the cap element 1809 may comprise other materials.

FIG. 19 and FIG. 20 each illustrates an example view of at least a portion of an example aerosol collection device subsequent to the buffer solution being released in accordance with examples of the present disclosure.

Referring now to FIG. 19, an example cross-sectional view of an example aerosol collection device 1900 in accordance with examples of the present disclosure is illustrated.

In the example shown in FIG. 19, the example aerosol collection device 1900 comprises a first vertical ridge element 1901 and a second vertical ridge element 1903 disposed on an inner lateral surface 1909 of the example aerosol collection device 1900. As described above, the handle portion of the holder element of the capsule component 1902 may be positioned and secured between the first vertical ridge element 1901 and the second vertical ridge element 1903. In the example shown in FIG. 19, when a vertically downward force is exerted on a top surface of the upper plunger component 1911, the leg portion 1907 of the upper plunger component 1911 travels downwards between the first vertical ridge element 1901 and the second vertical ridge element 1903, and pushes the handle portion of the holder element of the capsule component 1905 to travel downwards.

In some embodiments, after the cap element of the capsule component being broken by the capsule extraction body element (for example, a protrusion on a top surface of the capsule extraction body element), the capsule component travels downwards until stopped by the capsule extraction body element. In the example shown in FIG. 19, the capsule component 1902 is stopped at least partially by the capsule extraction body element 1904. In this state, the capsule extraction body element 1904 is at least partially within the cavity of the capsule component 1902 (where the buffer solution was previously stored).

As described above, in accordance examples of the present disclosure, a filter component is positioned adjacent to the capsule extraction body element of the vessel component of an example aerosol collection device. Referring now to FIG. 20, an example cross-sectional view of at least a portion of an example aerosol collection device 2000 is shown.

In the example shown in FIG. 20, a filter component 2002 is positioned adjacent to the capsule extraction body element 2004. After receiving a vertically downward force, the upper plunger component 2008 pushes the capsule component 2006 downwards, causing the capsule extraction body element 2004 to break the seal component of the capsule component 2006 and release the buffer solution from the capsule component 2006. Because the filter component 2002 is positioned adjacent to the capsule extraction body element 2004, the buffer solution flows to the filter component 2002 and wets the filter component 2002.

As such, in accordance with examples of the present disclosure, an example method for operating an aerosol collection device is provided. In some embodiments, the example method comprises exerting a vertically downward force on a top surface of an upper plunger to cause releasing buffer solution from at least one capsule component to a filter component. As described above, the example method may further comprise providing a sample to the filter component (for example, but not limited to, a user coughing to the aerosol collection device through a sample transfer adapter described herein).

As described above, example embodiments of the present disclosure provide various technical advantages and benefits. For example, example embodiments of the present disclosure provide an aerosol collection device that may define a flow channel for collecting aerosol from a sample and/or may define a vent channel for discharging the sample from the aerosol collection device.

Figure 21:
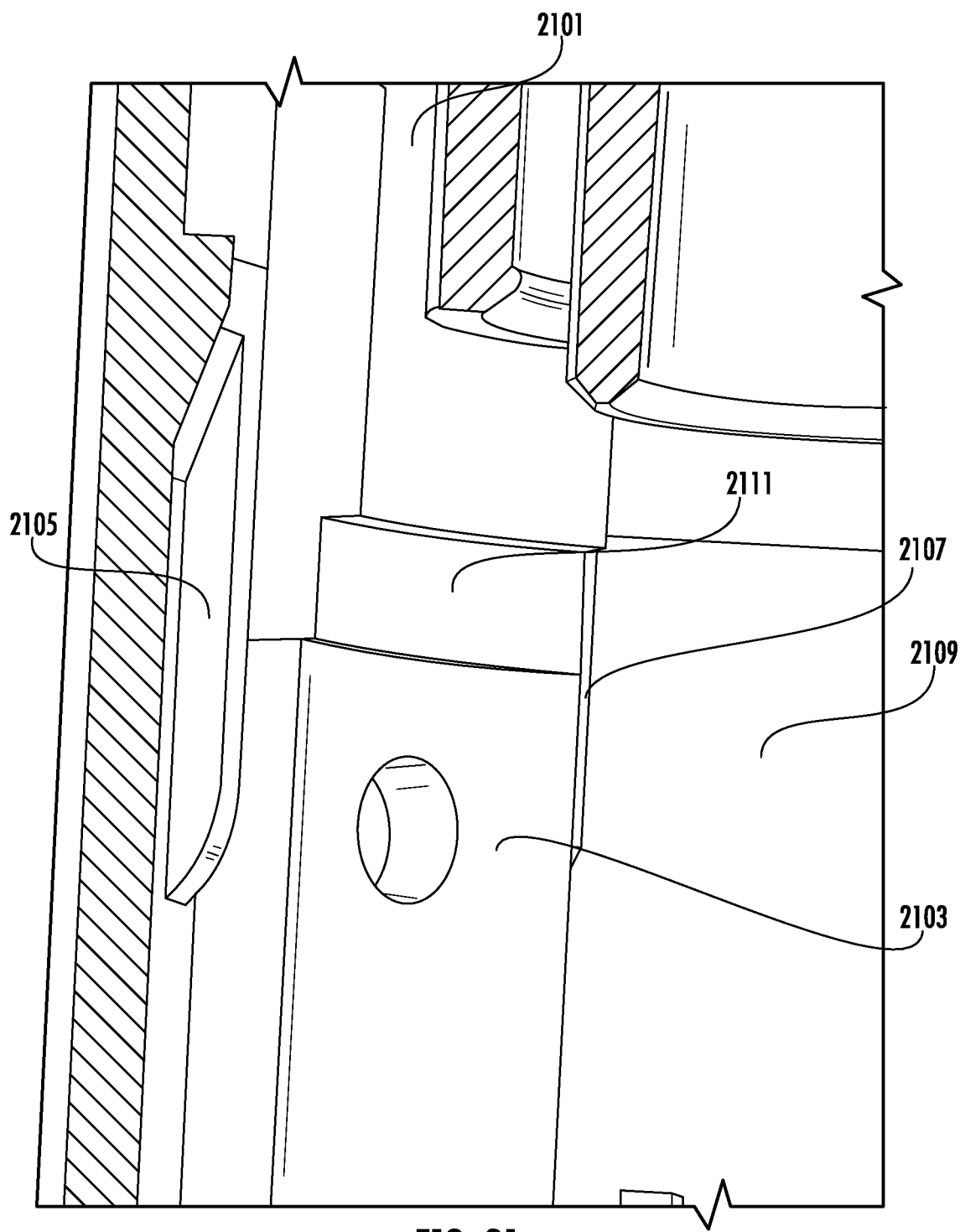
FIG. 21 illustrates an example view of at least a portion of an example upper plunger component and at least a portion of an example capsule component in accordance with examples of the present disclosure.

FIG. 21 illustrates at least a portion of an example upper plunger component 2101 and at least a portion of an example capsule component 2103 in accordance with examples of the present disclosure.

In the example configuration shown in FIG. 21, a bottom surface of the upper plunger component 2101 is in contact with a top surface of a capsule component 2103. For example, a bottom surface of a leg portion 2111 of the upper plunger component 2101 is in contact with the top surface of the capsule component 2103. As described above, the example upper plunger component 2101 may receive a vertically downward force exerted on a top surface of the example upper plunger component 2101. The vertically downward force may cause the example upper plunger component 2101 to travel downwards between a first vertical ridge element 2105 and a second vertical ridge element 2107, which are disposed on an inner lateral surface 2109 of an vessel component. The vertically downward force may further cause the cap element of the capsule component 2103 to be broken, and the buffer solution to be released from the capsule component 2103.

Figure 22:
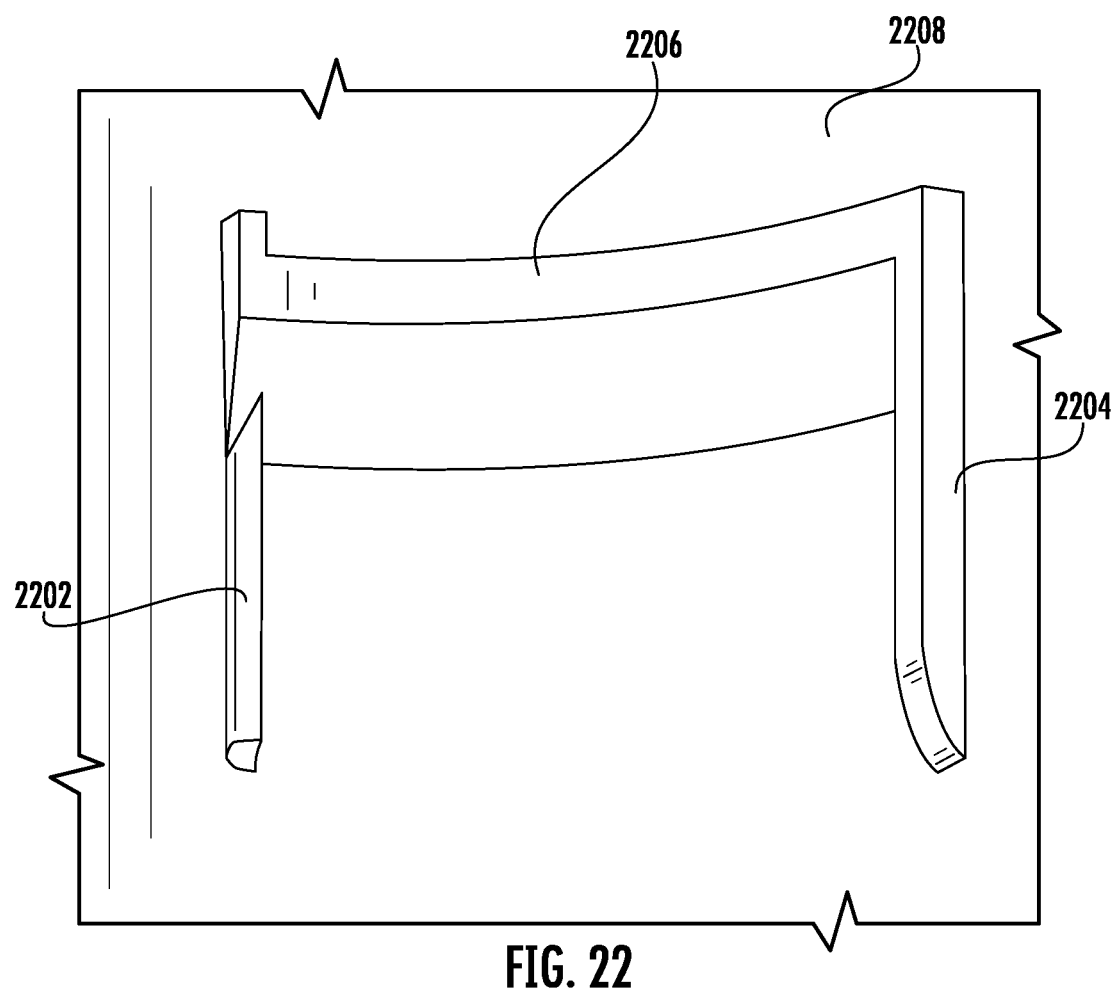
FIG. 22 illustrates an example view of example ridge elements disposed on an inner lateral surface of an example vessel component in accordance with examples of the present disclosure.

As described above, the first vertical ridge element 2105 and the second vertical ridge element 2107 may comprise at least one vertical lock ridge element and at least one vertical stop ridge element. Referring now to FIG. 22, example ridge elements positioned on an inner lateral surface 2208 of an example vessel component in accordance with examples of the present disclosure are illustrated.

In the example illustrated in FIG. 22, a vertical lock ridge element 2202, a vertical stop ridge element 2204, and a horizontal ridge element 2206 are disposed on the inner lateral surface 2208 of an vessel component. In the example shown in FIG. 22, the vertical lock ridge element 2202 is connected to and in an orthogonal arrangement with the horizontal ridge element 2206. Additionally, or alternatively, the vertical stop ridge element 2204 is connected to and in an orthogonal arrangement with the horizontal ridge element 2206.

In some embodiments, the vertical lock ridge element 2202 may comprise a slope surface that extends from the inner lateral surface 2208 at an angle less than 90 degrees. In some embodiments, the angle is 45 degrees. In some embodiments, the angle is 51 degrees. In some embodiments, the angle may be of other values. The angle allows for the vertical lock ridge element 2202 to deflect inwards instead of stopping rotation of a leg portion of an upper plunger component. In other words, the slope surface enables a leg portion of an upper plunger component to rotate and slide past the vertical lock ridge element 2202, but prevents the leg portion of the upper plunger component from rotating back after the leg portion rotates past the vertical lock ridge element 2202. For example, prior to sliding past the vertical lock ridge element 2202, the upper plunger component may be in a first configuration where it is in contact with a capsule component. Subsequent to sliding past the vertical lock ridge element 2202, the upper plunger component may be in a second configuration where it is in contact with a lower plunger component. Details of the first configuration and the second configuration are described further herein.

In some embodiments, the vertical stop ridge element 2204 may comprise two side surfaces, each having an orthogonal arrangement with the inner lateral surface 2208. In some embodiments, the vertical stop ridge element 2204 comprises a top surface that is connected to the two side surfaces and has the same curvature as the inner lateral surface 2208. In some embodiments, the vertical stop ridge element 2204 does not comprise a slope surface that extends from the inner lateral surface 2208 at an angle less than 90 degrees. As such, the vertical stop ridge element 2204 prevents a leg portion of an upper plunger component to rotate and slide past the vertical stop ridge element 2204.

In some embodiments, the height of the vertical lock ridge element 2202 (e.g. a distance between the top point of the vertical lock ridge element 2202 and the point on the inner lateral surface 2208 where the vertical lock ridge element 2202 protrudes from) is less than (for example, half of) the height of the vertical stop ridge element 2204 (e.g. a distance between the top surface of the vertical stop ridge element 2204 and the inner lateral surface 2208 where side surfaces of the vertical stop ridge element 2204 protrude from), so that the leg portion of the upper plunger component may slide past the vertical lock ridge element 2202 but may not past the vertical stop ridge element 2204.

Additionally, or alternatively, the height of the vertical lock ridge element 2202 (e.g. a distance between the top point of the vertical lock ridge element 2202 and the point on the inner lateral surface 2208 where the vertical lock ridge element 2202 protrudes from) is less than (for example, half of) the height of the horizontal ridge element 2206 (e.g. a distance between the top point of the horizontal ridge element 2206 and the point on the inner lateral surface 2208 where the horizontal ridge element 2206 protrudes from).

Figure 23:
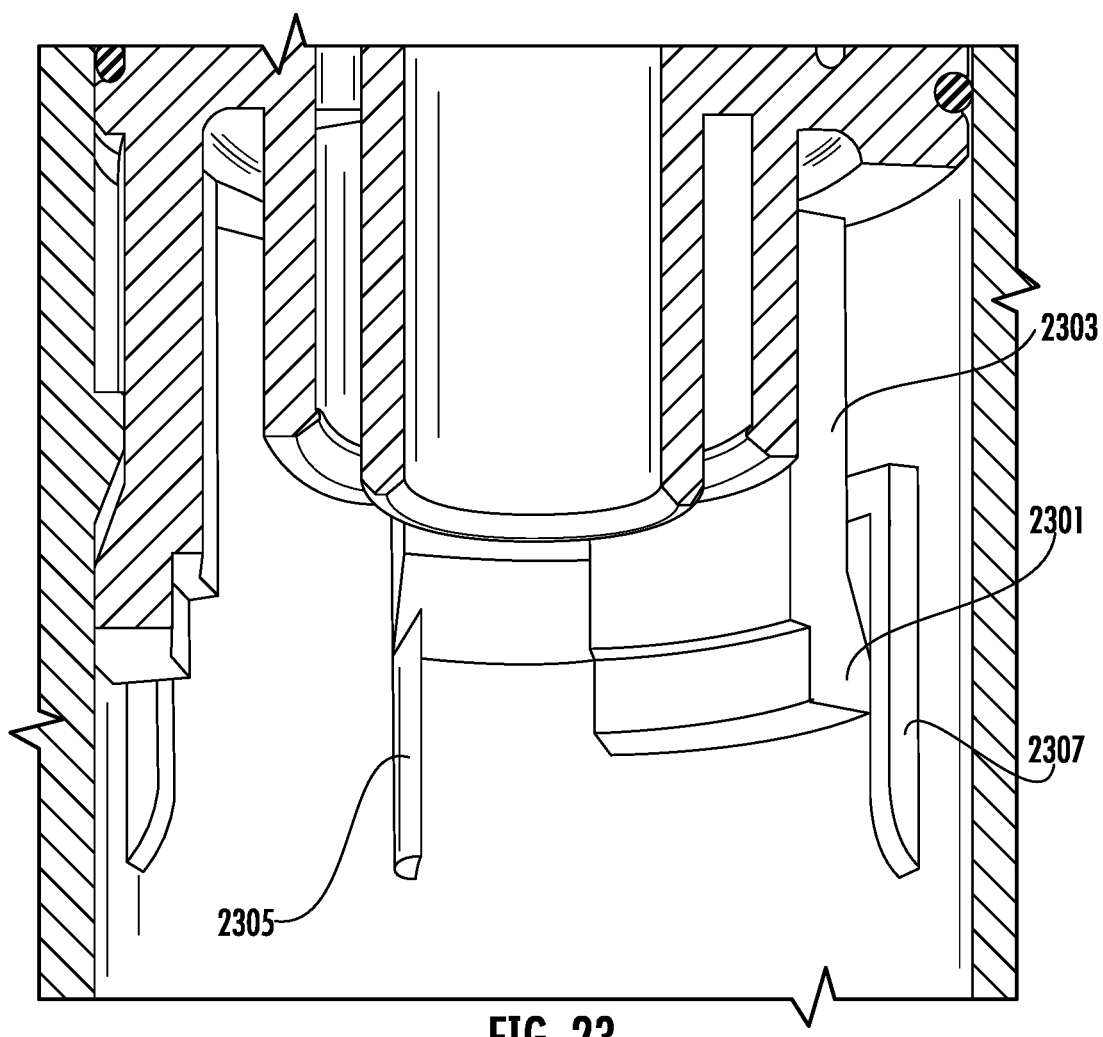
FIG. 23 illustrates an example view of an example portion of an example aerosol collection device in accordance with examples of the present disclosure.
Figure 24:
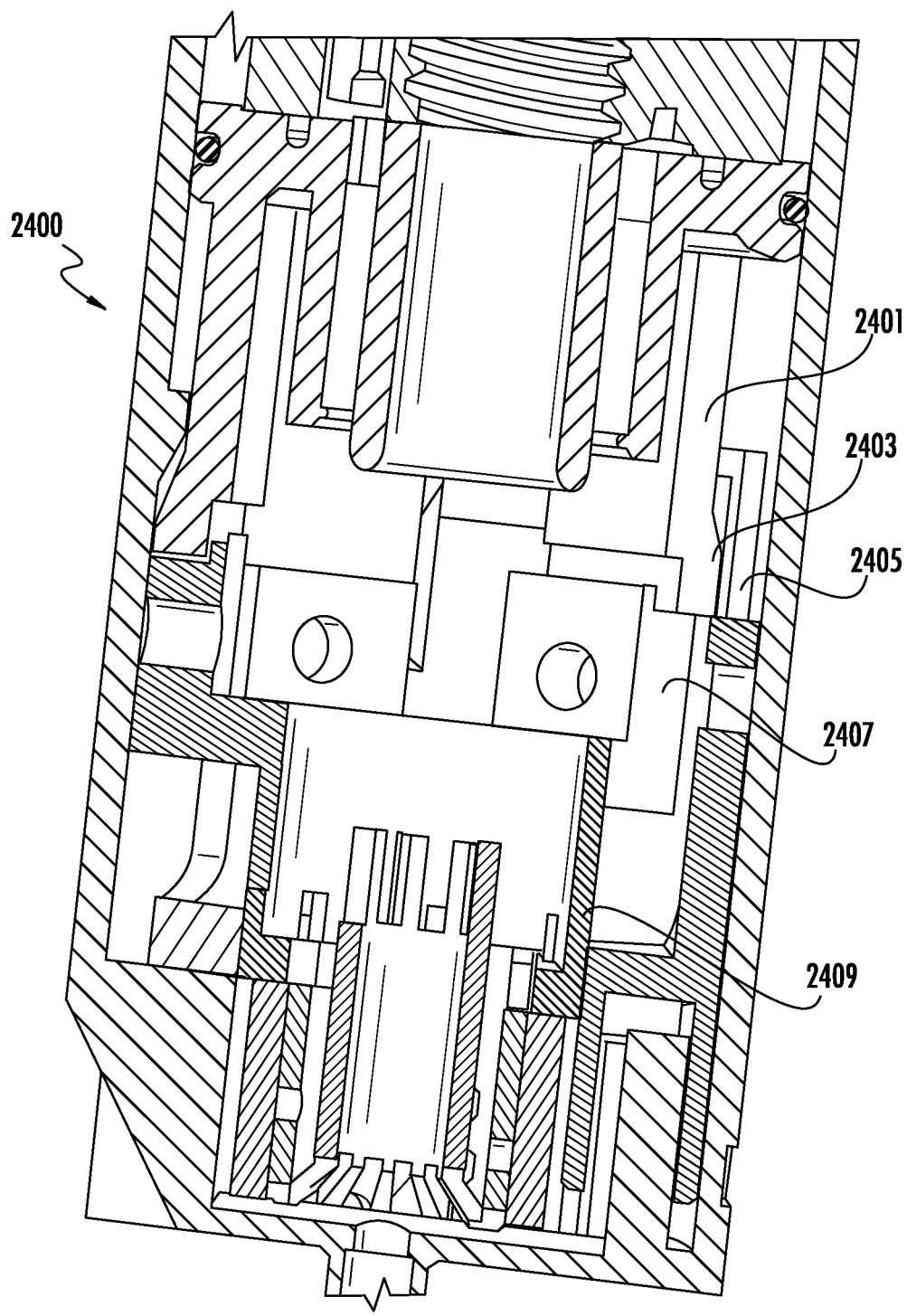
FIG. 24 illustrates an example view of an example portion of an example aerosol collection device in accordance with examples of the present disclosure.

FIG. 23 and FIG. 24 illustrate example views of at least portions of an example aerosol collection device after the upper plunger component is rotated.

In particular, FIG. 23 illustrates an example cross-sectional view of at least a portion of an example upper plunger component 2303. In the example shown in FIG. 23, a leg portion 2301 of the example upper plunger component 2303 has been rotated and slide past a vertical lock ridge element 2305 and stopped at a vertical stop ridge element 2307. For example, a user may rotate the plunger head element of the upper plunger component, which in turn cause the leg portion 2301 of the example upper plunger component 2303 to rotate.

In some embodiments, the rotation and sliding of the leg portion 2301 of the upper plunger component 2303 is restricted by the horizontal ridge element 2206 in the vertical direction. In some embodiments, the horizontal ridge element 2206 prevents the leg portion 2301 (and the upper plunger component 2303) from moving vertically upwards.

FIG. 24 illustrates an example cross-sectional view of an example aerosol collection device 2400 after the upper plunger component 2401 is rotated.

As described above, the leg portion 2403 of the upper plunger component 2401 is stopped by the vertical stop ridge element 2405 from further rotating. In the configuration shown in FIG. 24, the bottom surface of the upper plunger component 2401 (for example, the bottom surface of the leg portion 2403) is in contact with a top surface of a plunger support wing 2407 of the lower plunger component 2409.

As such, examples of the present disclosure may provide an example aerosol collection device that comprises a lower plunger component and an upper plunger component. Similar to those described above, the lower plunger component may comprise a plurality of plunger support wings, and each of the plurality of plunger support wings is positioned between two of a plurality of capsule components.

In some embodiments, the upper plunger component is configured to translate from a first configuration to a second configuration triggered by a rotational force (for example, a user rotating the plunger head element of the upper plunger component). In the words, the upper plunger component (which may start at a first configuration) may be rotated and arrive at a second configuration.

In the first configuration (for example, as shown in FIG. 21), a bottom surface of the upper plunger component is in contact with a top surface of each of the plurality of capsule components. For example, the bottom surface of the at least one leg portion is in contact with the top surface of each of the plurality of capsule components.

As described above, in some embodiments, the lower plunger component and the upper plunger component are housed within a vessel component having at least one vertical lock ridge element and at least one vertical stop ridge element disposed on an inner lateral surface of the vessel component. In some embodiments, the rotational force on the upper plunger component causes at least a portion of the at least one leg portion to (from the first configuration) rotate past the at least one vertical lock ridge element and stop at the at least one vertical stop ridge element (and arrive at the second configuration).

In the second configuration (for example, as shown in FIG. 24), the bottom surface of the upper plunger component is in contact with a top surface of each of the plurality of plunger support wings of the lower plunger component. For example, the bottom surface of the at least one leg portion is in contact with the top surface of each of the plurality of plunger support wings.

Accordingly, an example method for operating an aerosol collection device is provided in accordance with examples of the present disclosure. The example method may comprise exerting a rotational force on an upper plunger component, causing the upper plunger component to translate from a first configuration to a second configuration. In some embodiments, the example method further comprises exerting a vertical force on a top surface of the upper plunger subsequent to exerting the rotational force, details of which are described in connection with at least FIG. 25 to FIG. 29B.

Figure 25:
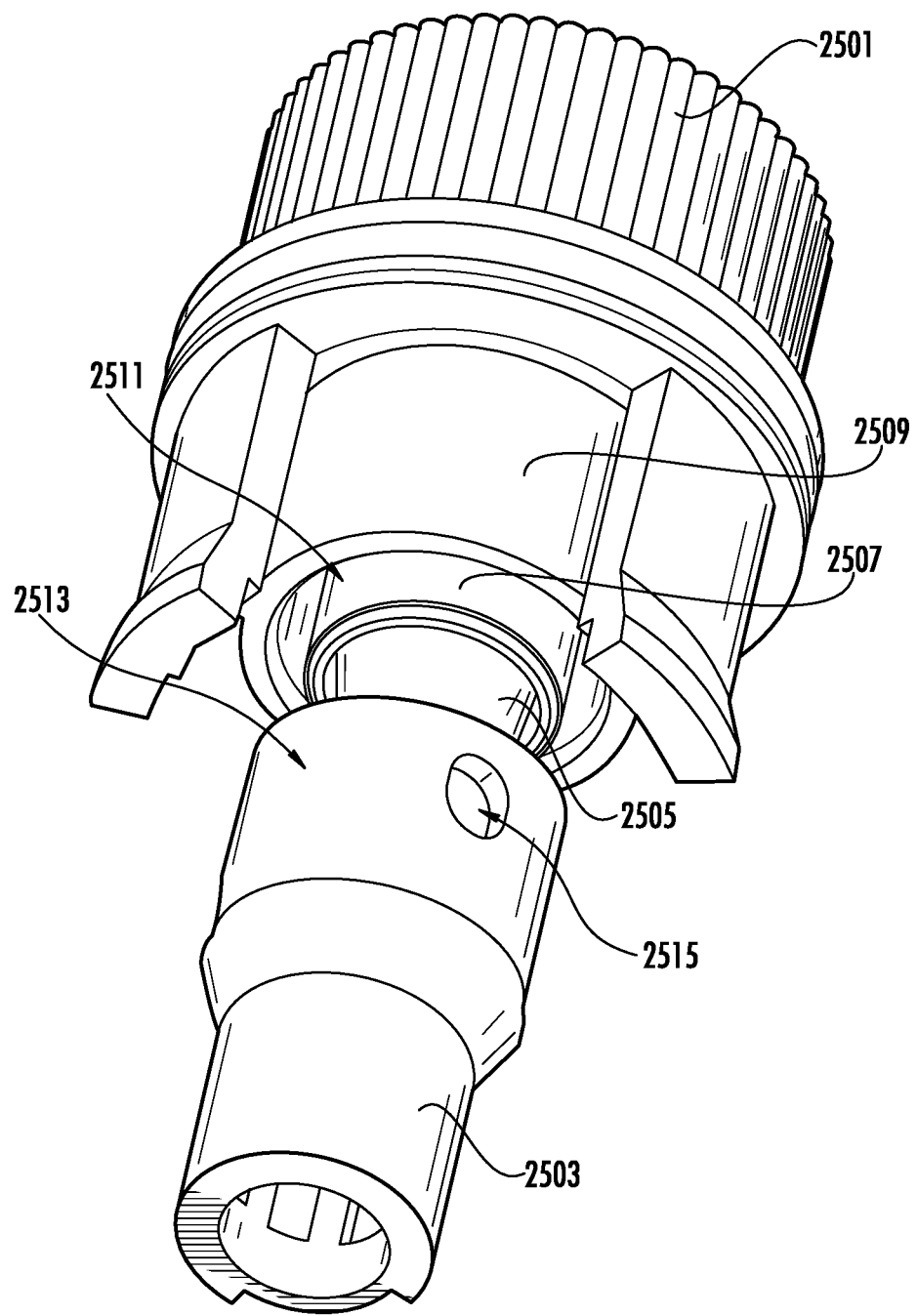
FIG. 25 illustrates an example view of an example tube component and an example upper plunger component in accordance with examples of the present disclosure.

FIG. 25 illustrates an example isolated view showing an example tube component 2503 and an example upper plunger component 2501 in accordance with examples of the present disclosure. In particular, FIG. 25 illustrates an example structural relationship between the example tube component 2503 and the example upper plunger component 2501 in accordance with examples of the present disclosure.

In the example shown in FIG. 25, the top portion of the pipe element 2505 of the tube component 2503 is positioned within the central annulus portion 2507 of the upper plunger component 2501.

In an example assembled aerosol collection device, when a vertical forced is exerted on the top surface of the upper plunger component 2501, at least a portion of the vent bluff annulus element 2513 of the tube component 2503 enters into gap 2511 between the central annulus portion 2507 of the upper plunger component 2501 and the intermedial annulus portion 2509 of the upper plunger component 2501. In the example shown in FIG. 25, the vent bluff annulus element 2513 comprises at least one opening 2515.

Figure 26A:
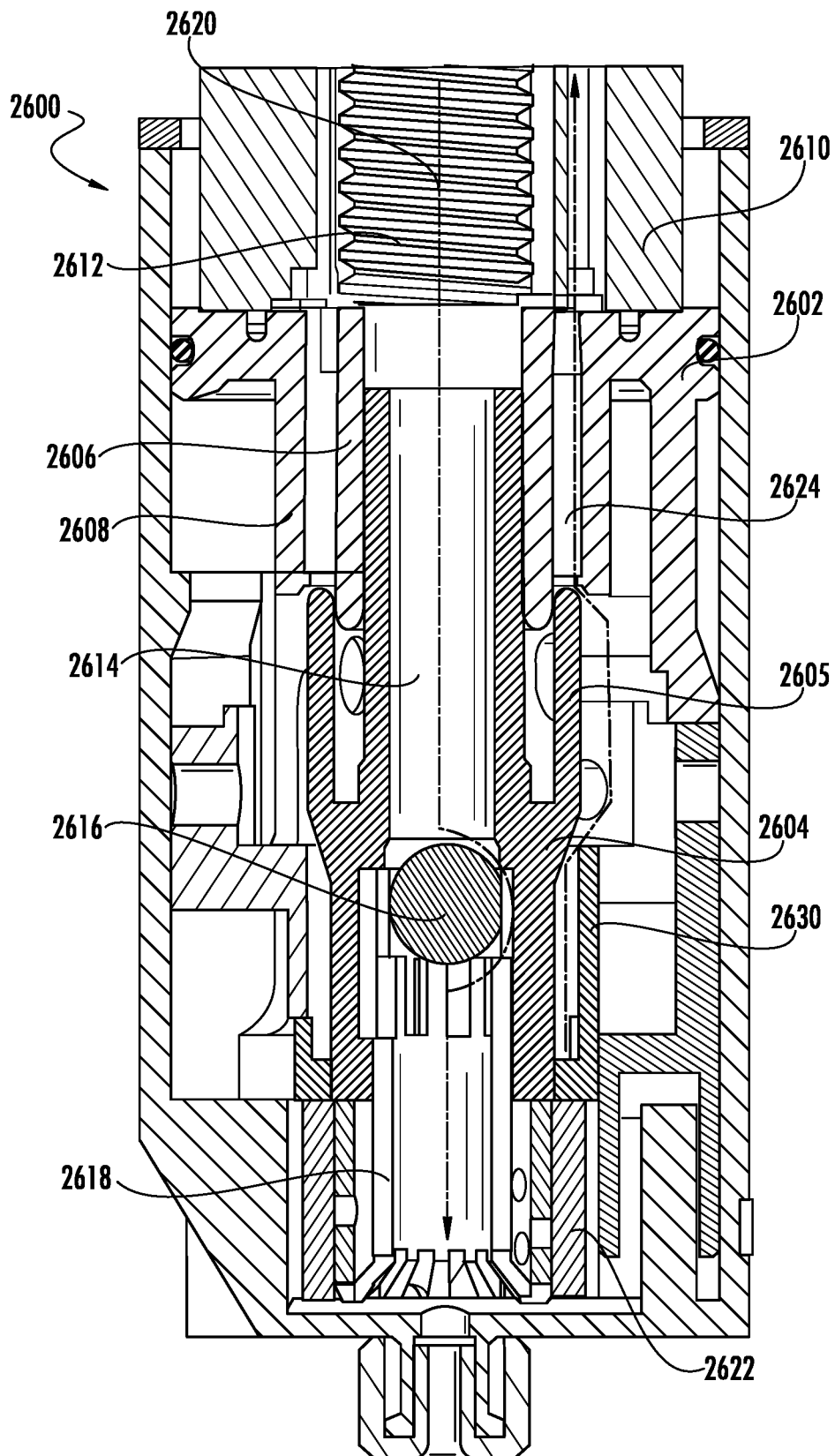
FIG. 26A, FIG. 26B, and FIG. 26C each illustrates an example view of at least a portion of an example aerosol collection device in accordance with examples of the present disclosure.
Figure 26B:
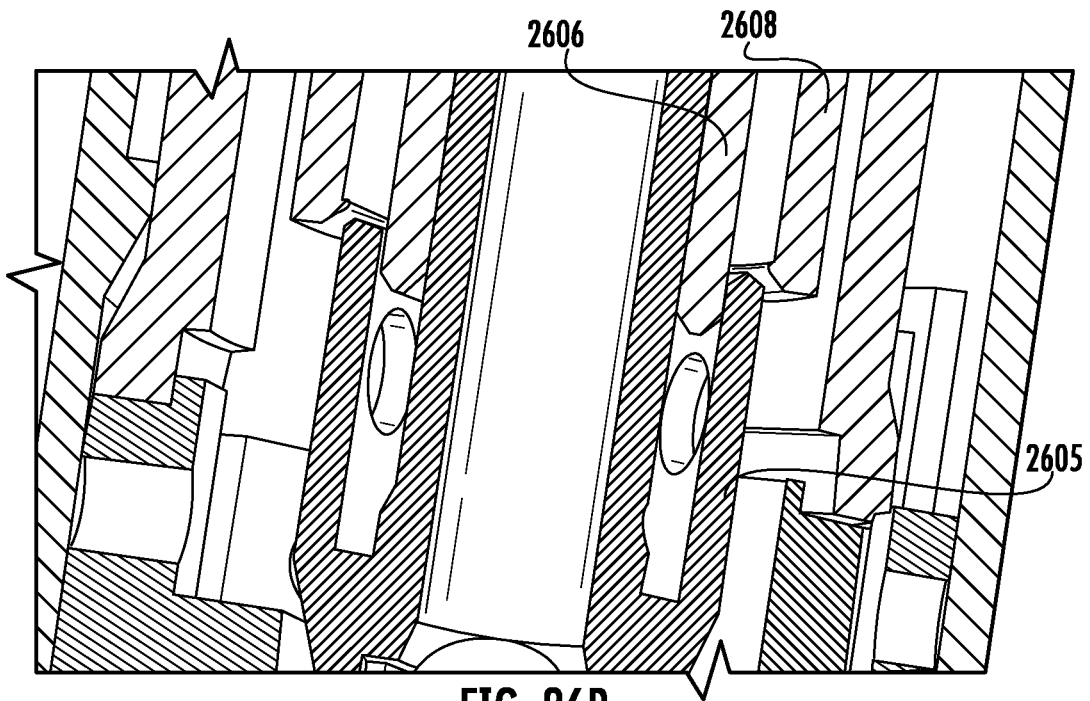
Figure 26C:
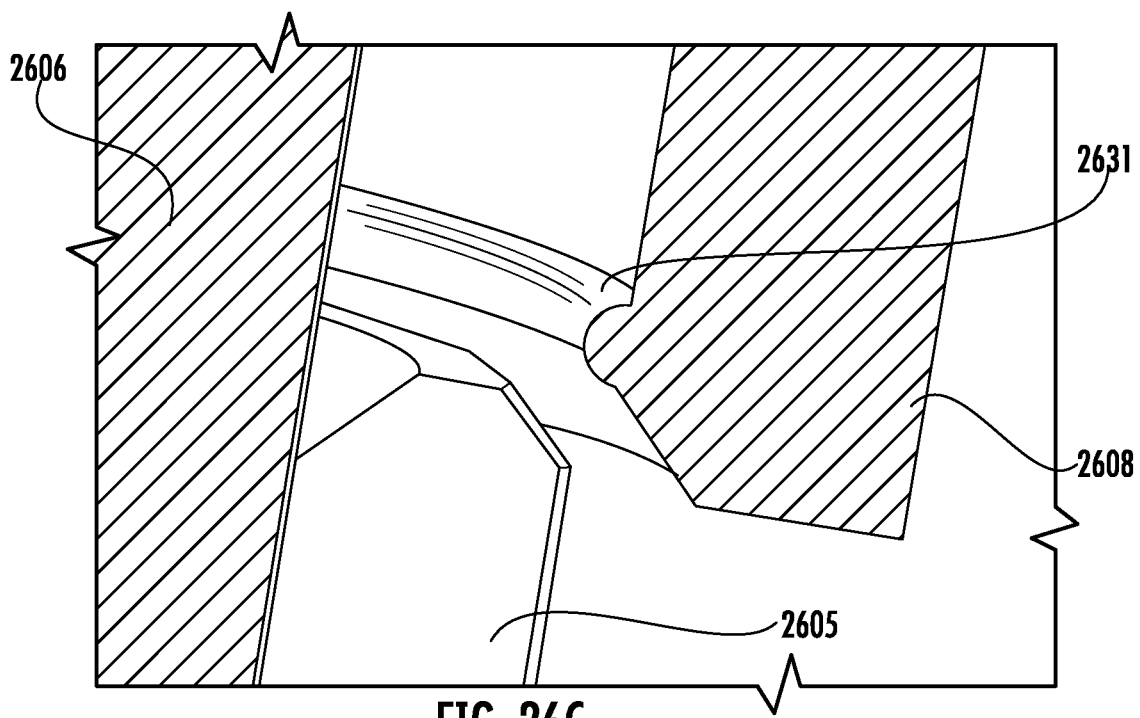

FIG. 26A, FIG. 26B, and FIG. 26C each illustrates at least a portion of an example aerosol collection device 2600 in accordance with examples of the present disclosure.

In the example shown in FIG. 26A, the example aerosol collection device 2600 comprises an upper plunger component 2602 and a tube component 2604. Similar to those described above, the upper plunger component 2602 comprises a central annulus portion 2606 and an intermedial annulus portion 2608. In the example shown in FIG. 26A, the central annulus portion 2606 is disposed within the intermedial annulus portion 2608, forming a gap between the central annulus portion 2606 and the intermedial annulus portion 2608.

In some embodiments, the tube component 2604 comprises a vent bluff annulus element 2605. In some embodiments, at least a portion of the central annulus portion 2606 of the upper plunger component 2602 is positioned within and in contact with the vent bluff annulus element 2605 of the tube component 2604.

In some embodiments, the upper plunger component 2602 comprises a plunger head element 2610 defining a central bore 2612. In some embodiments, the tube component 2604 comprises a pipe element 2614 at least partially positioned within the central annulus portion 2606 and connected to the central bore 2612, forming a portion of a flow channel for receiving sample in the aerosol collection device 2600.

For example, the sample may enter the aerosol collection device 2600 (from a sample transfer adapter and) through the central bore 2612, may travel through the pipe element 2614, may travel downwards pass the valve component 2616 and arrive within the valve support annulus element 2618. The dashed arrow 2620 in FIG. 26A indicates an example flow direction of a sample in the flow channel. For example, the flow channel may comprise portions that are defined by at least the central bore 2612, the pipe element 2614 (including the gap between the valve component 2616 and the inner surface of the pipe element 2614) and the valve support annulus element 2618. In such an example, the sample may travel through the central bore 2612, the pipe element 2614 (including through the gap between the valve component 2616 and the inner surface of the pipe element 2614) and arrive within the valve support annulus element 2618. In some embodiments, the sample may interact with the buffer solution in the filter component 2622. For example, as the user blows air in the sample transfer adapter, the air travel into the buffer solution through the flow channel and forms one or more bubbles.

In some embodiments, the sample may be discharged from the aerosol collection device 2600 through a vent channel. The vent channel may comprise portions that are defined by at least the space between the outer surface of the tube component 2604 and the lower plunger component 2630 and the gap between the central annulus portion 2606 and the intermedial annulus portion 2608. For example, the sample (for example, air) may travel from the filter component 2622 upwards along the gap between the outer surface of the tube component 2604 and the lower plunger component 2630, along the gap between the central annulus portion 2606 and the intermedial annulus portion 2608, and out of the aerosol collection device through one or more openings/ ports on the plunger head element 2610. The dashed arrow 2624 in FIG. 26A indicates an example vent direction of the sample in the vent channel.

For example, when a user provides a sample to the aerosol collection device 2600 by coughing or blowing air into the aerosol collection device 2600 through a sample transfer adapter connected to the central bore 2612, the sample travels through the aerosol collection device 2600 by flowing in the flow channel that guides the air to the filter component 2622, and then be discharged from the aerosol collection device 2600 through the vent channel.

FIG. 26B and FIG. 26C each illustrates a zoomed view of at least a portion of the aerosol collection device 2600. In the examples shown in FIG. 26B and FIG. 26C, there is a gap between the top surface of the vent bluff annulus element 2605 and a bottom surface of the intermedial annulus portion 2608, and the gap is part of the vent channel that enables the sample to be discharged from the aerosol collection device 2600. Further, as shown in FIG. 26C, a sealing ridge 2631 may be disposed on an inner surface of the intermedial annulus portion 2608. In some embodiments, the sealing ridge 2631 may be in a shape similar to a ring shape. In some embodiments, the sealing ridge 2631 may be in other shapes. When a vertically downward force is exerted on the upper plunger component, the sealing ridge 2631 is configured to seal the vent channel, details of which are described herein.

Figure 27A:
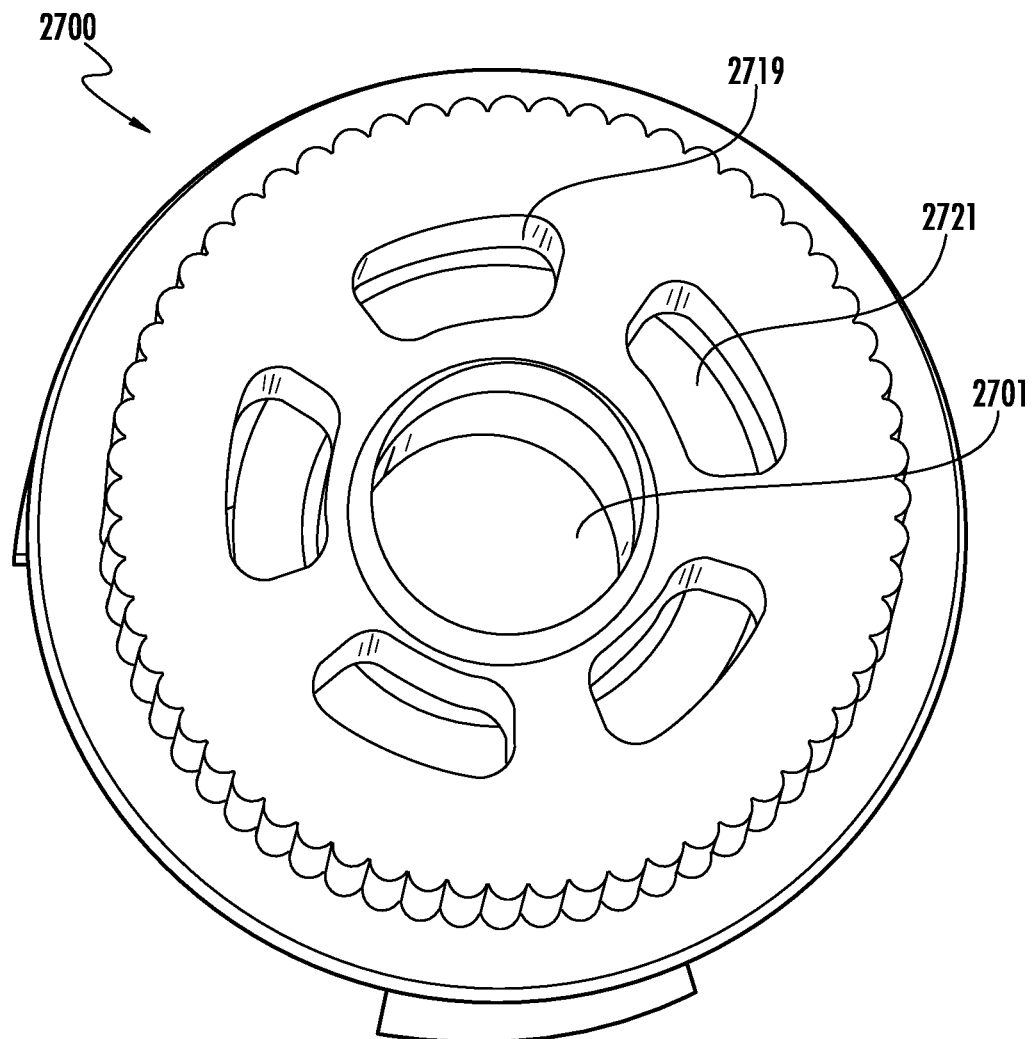
FIG. 27A and FIG. 27B each illustrates an example view of an example upper plunger component in accordance with examples of the present disclosure.
Figure 27B:
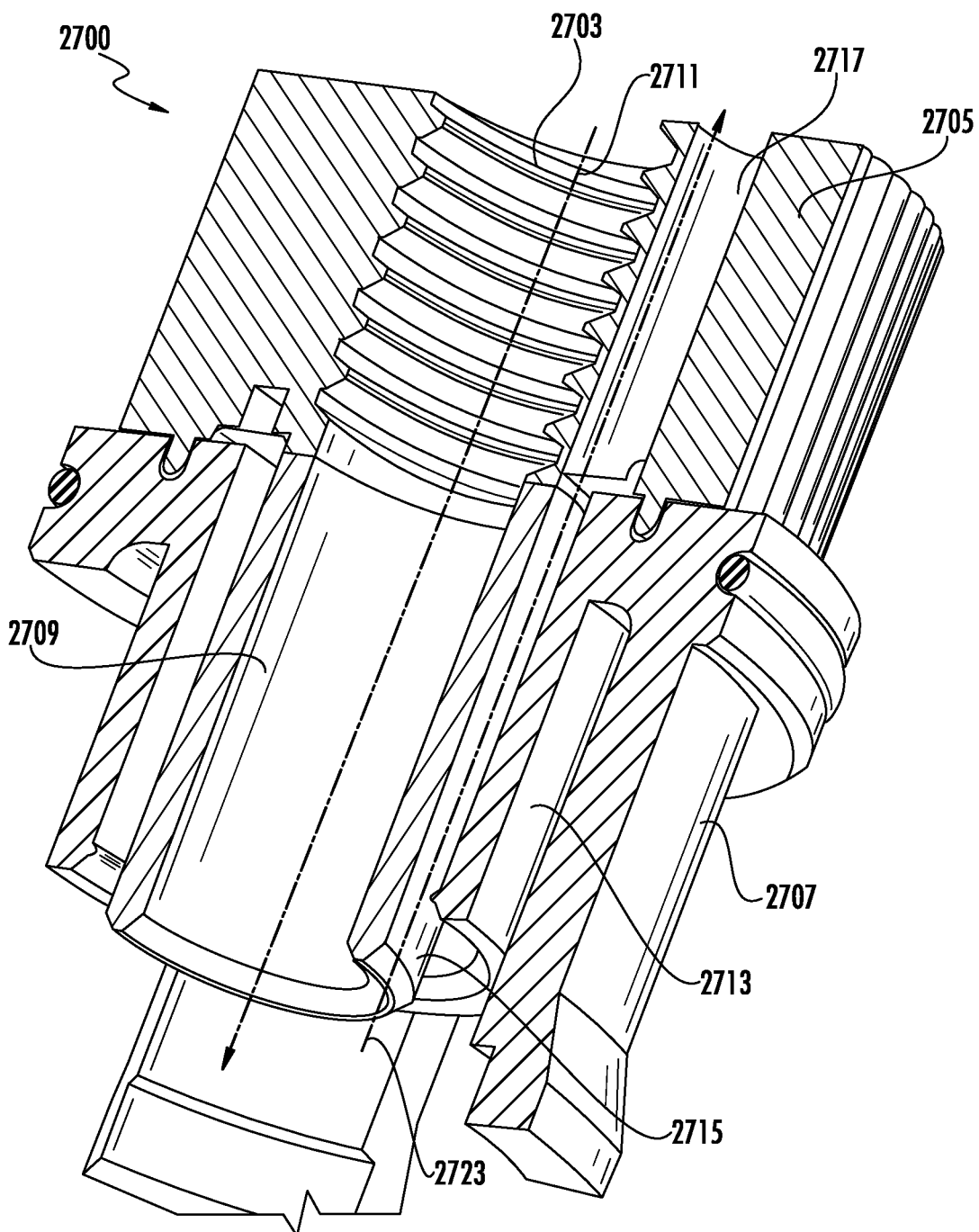

FIG. 27A and FIG. 27B illustrate example views of an example upper plunger component 2700 in connection with the flow channel and the vent channel.

As described above, a sample may enter an aerosol collection device through the opening 2701 of the central bore 2703 of the plunger head element 2705. The sample passes through a tube element 2709, which forms part of the flow channel, the flow direction of which is shown by the dashed arrow 2711 in FIG. 27B.

As described above, the central annulus portion 2715 and the intermedial annulus portion 2713 define a portion of a vent channel for discharging a sample. For example, at least a portion of the gap between the central annulus portion 2715 and the intermedial annulus portion 2713 of the plunger body element 2707 defines at least a part of the vent channel. Subsequently, the sample travels through the aperture 2717 of the plunger head element 2705 and exits the aerosol collection device through the opening 2719. As described above, in some embodiments, a filter 2721 may be disposed between the plunger head element 2705 and the plunger body element 2707. In FIG. 27B, the dashed arrow 2723 illustrates the vent direction of the sample in the vent channel.

Figure 28:
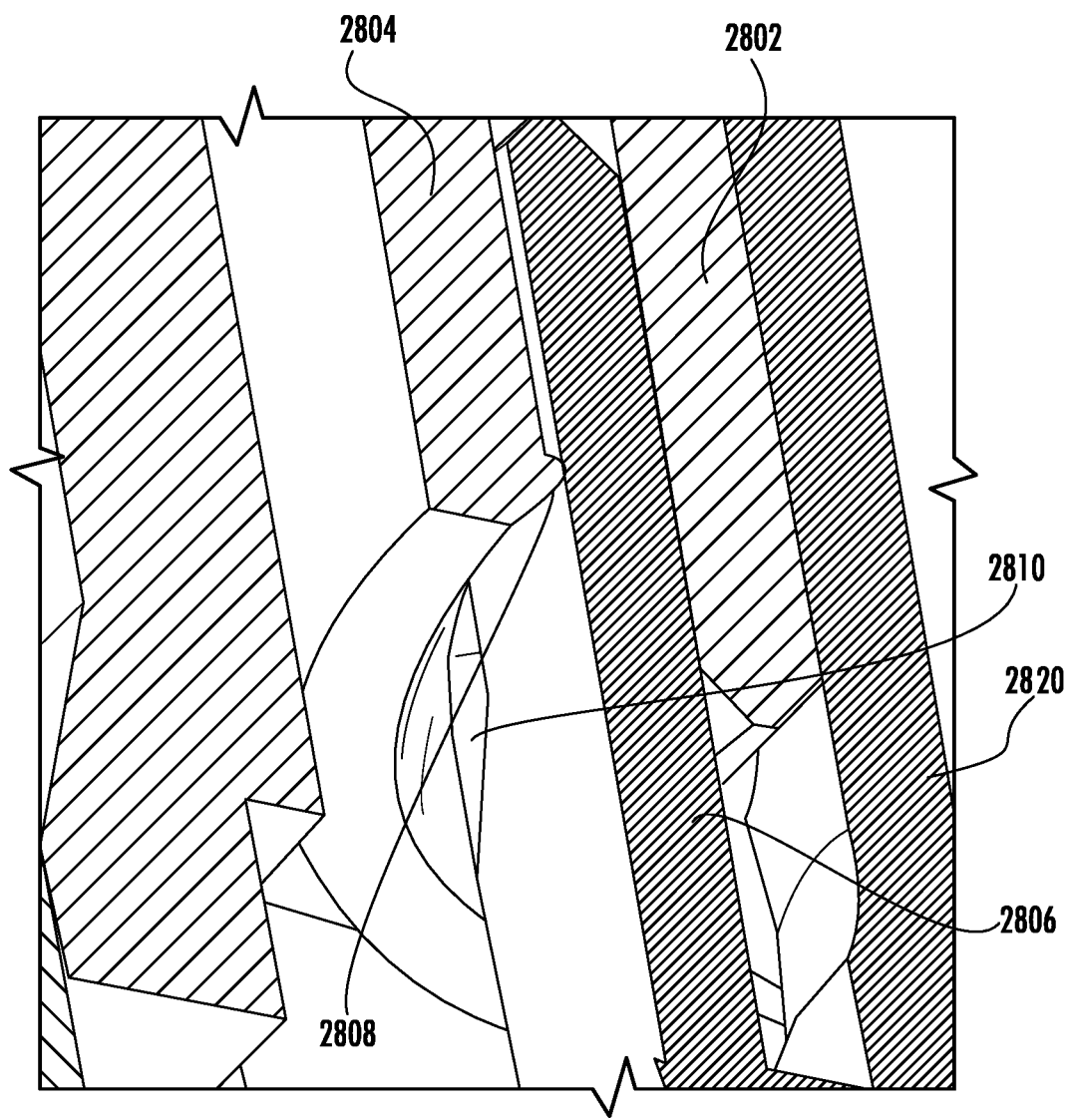
FIG. 28 illustrates an example view of an example tube component and an example upper plunger component in accordance with examples of the present disclosure.

FIG. 28 illustrates an example view of at least a portion of an example tube component and a portion of an example upper plunger component in accordance with examples of the present disclosure. In particular, FIG. 28 illustrates the structural relationship between the example tube component and the example upper plunger component as a vertically downward force is exerted on the top surface of the example upper plunger component, which is subsequent to a rotational force being exerted on the upper plunger component in accordance with those described above.

In the example shown in FIG. 28, the central annulus portion 2802 and the intermedial annulus portion 2804 may travel vertically downwards, and the vent bluff annulus element 2806 may enter the gap between the central annulus portion 2802 and the intermedial annulus portion 2804. As the vent bluff annulus element 2806 enters the gap between the central annulus portion 2802 and the intermedial annulus portion 2804, the sealing ridge 2808 on the inner surface of the intermedial annulus portion 2804 may be in contact with the outer surface of the vent bluff annulus element 2806. When the sealing ridge 2808 moves passes the opening 2810 on the vent bluff annulus element 2806, the sealing ridge 2808 blocks and seals the vent channel so that the sample may no longer exit through the vent channel. In some embodiments, the central annulus portion 2802 is longer than the intermedial annulus portion 2804 so that the central annulus portion 2802 pushes air between the vent bluff annulus element 2806 and the pipe element 2820 out through the opening 2810 as the central annulus portion 2802 and the intermedial annulus portion 2804 travel vertically downwards.

Figure 29A:
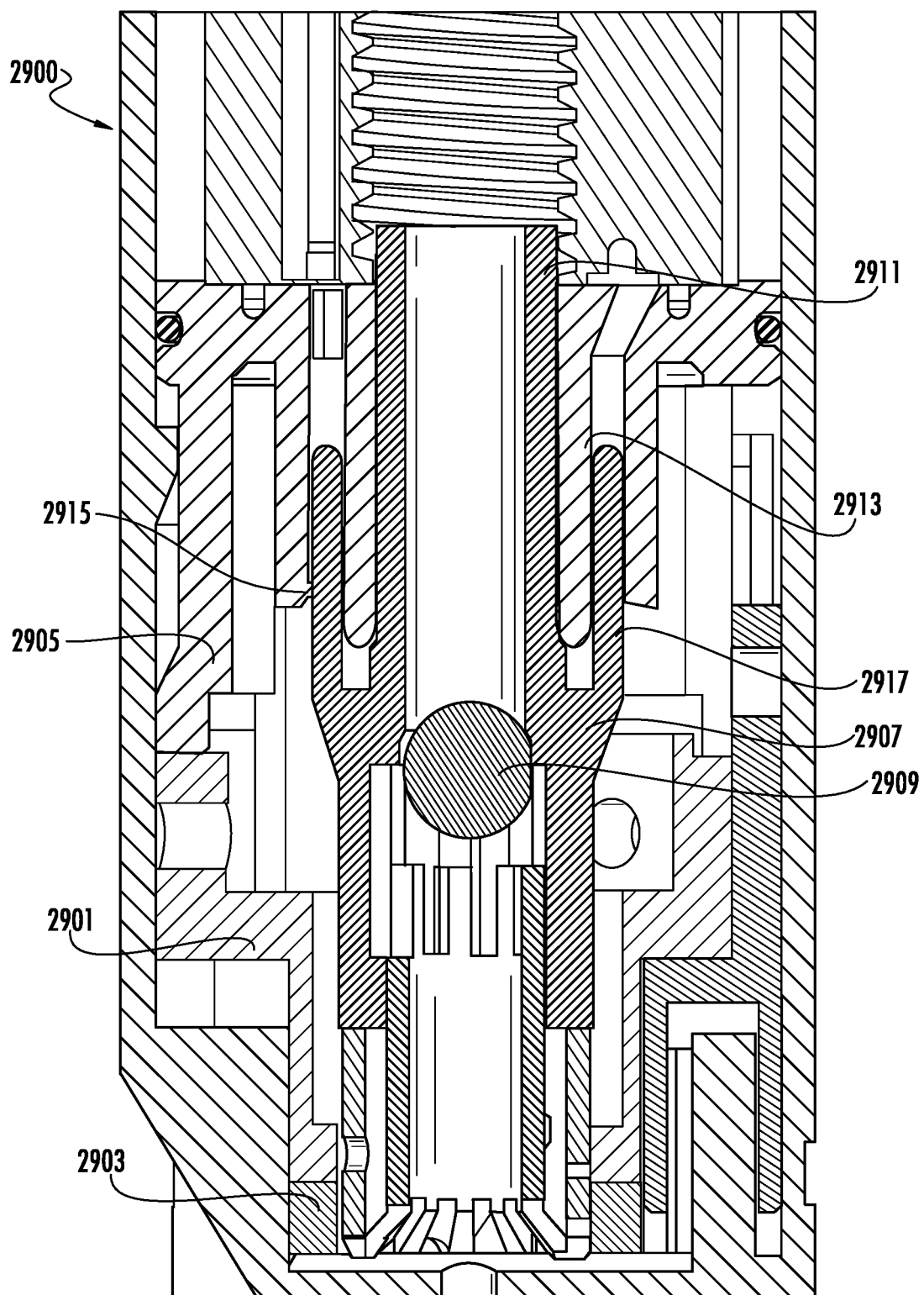
FIG. 29A and FIG. 29B each illustrates an example view of at least a portion of an example aerosol collection device in accordance with examples of the present disclosure.
Figure 29B:
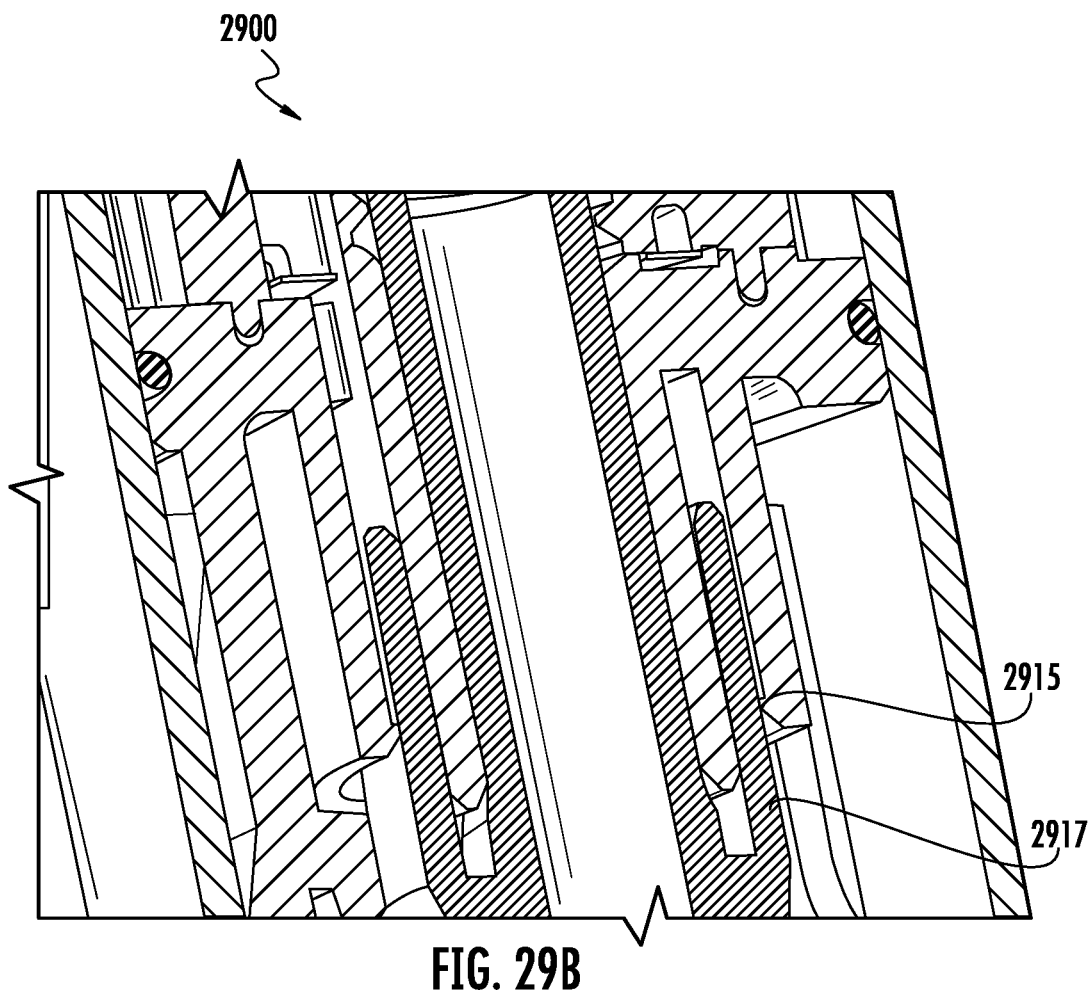

FIG. 29A and FIG. 29B each illustrates an example cross-sectional view of at least a portion of an example aerosol collection device 2900 in accordance with examples of the present disclosure In the example shown in FIG. 29A and FIG. 29B, the example aerosol collection device 2900 comprises at least a lower plunger component 2901. As shown, the bottom surface of the lower plunger component 2901 is in contact with a filter component 2903.

In some embodiments, the example aerosol collection device 2900 comprises an upper plunger component 2905 in contact with a top surface of the lower plunger component 2901 (e.g. in a second configuration as those described above). As such, in response receiving a vertical force exerted on a top surface of the upper plunger component 2905, the upper plunger component 2905 is configured to transfer the vertical force to the lower plunger component 2901 and cause a vertical movement of the lower plunger component 2901. In some embodiments, the vertical movement of the lower plunger component 2901 causes the filter component 2903 to be squeezed so that buffer solution that includes collected aerosols is discharged from the filter component 2903.

Further, in some embodiments, the upper plunger component 2905 is configured to transfer the vertical force to the tube component 2907 as at least a top portion of the pipe element 2911 of the tube component 2907 is housed within the central annulus portion 2913 of the upper plunger component 2905. The vertical force causes the tube component 2907 to travel downwards, causing the valve component 2909 to be in contact with the middle portion of the tube component 2907, thereby sealing the flow channel. Further, as described above in connection with at least FIG. 28, the vertical force causes the sealing ridge 2915 to travel downward along the vent bluff annulus element 2917 of the tube component 2907, thereby sealing the vent channel.

As such, in some embodiments, subsequent to a vertically downward force is applied on the top surface of the upper plunger component 2905 when it is in the second configuration, both the flow channel and the vent channel are sealed, building up inner pressure for extracting the buffer solution from the aerosol collection device 2900. In some embodiments, during operation, the cap element is secured back to an example aerosol collection device (for example, secured on top of the upper plunger component 2905) after a user provide sample to the aerosol collection device. In such embodiments, in order to apply the vertically downward force on the top surface of the upper plunger component 2905, a user must remove the cap element from the example aerosol collection device (for example, from the upper plunger component 2905) so that the vertically downward force can be applied on the upper plunger component.

Figure 30:
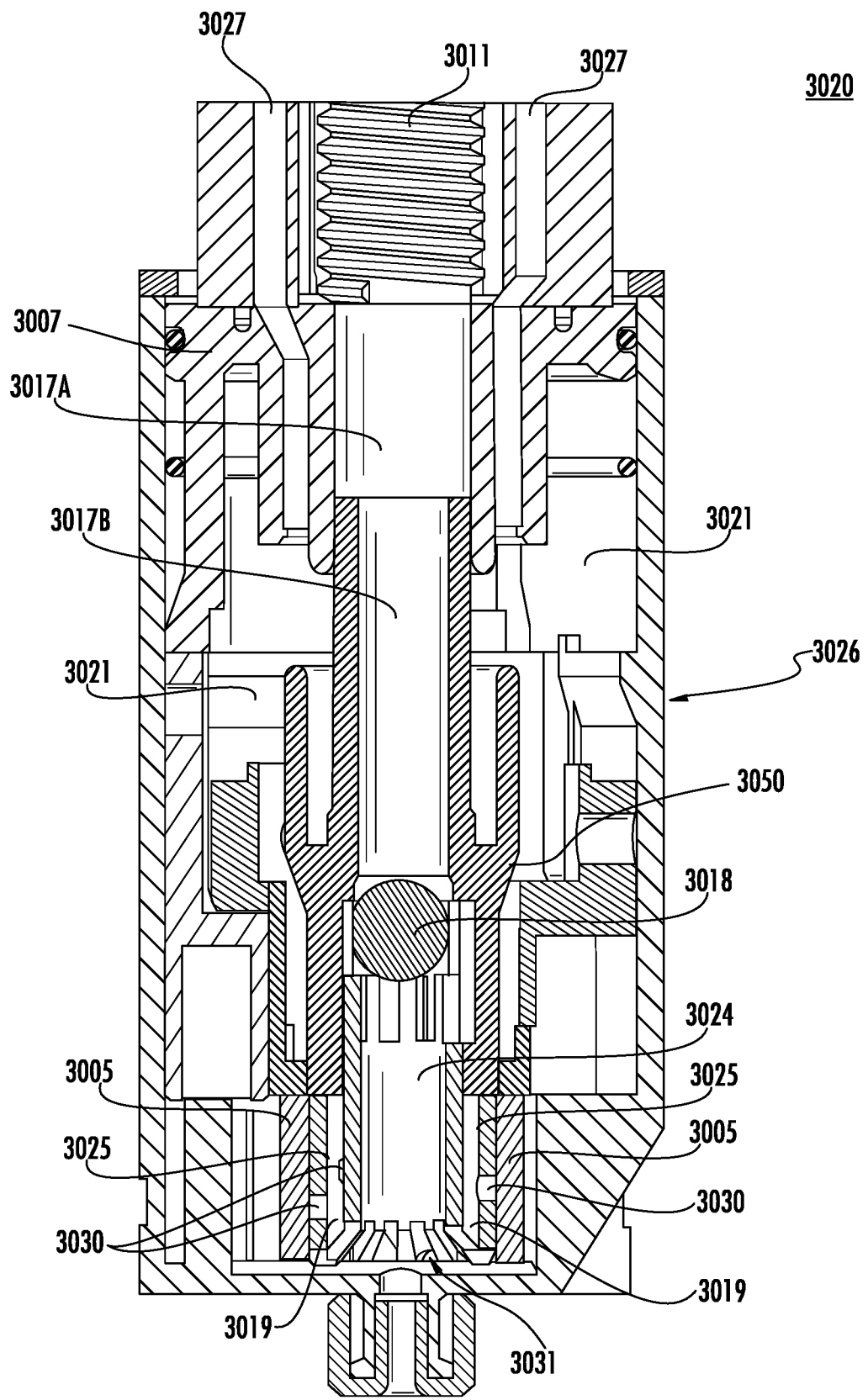
FIG. 30 illustrates an example cross-sectional view of an example aerosol collection device in accordance with various examples of the present disclosure.

Referring now to FIG. 30, a portion of an example cross-sectional view of the example aerosol collection device 3020 is illustrated.

In various embodiments, an exemplary aerosol collection device 3020 may comprise a device body 3026 that comprises an upper plunger component 3007, where one or more of a sample transfer adapter (e.g., a mask component, a sampling tunnel, a sampling hood, and/or the like) may be removably secured to the upper plunger component 3007. In the example shown in FIG. 30, the exemplary aerosol collection device 3020 may comprise a upper plunger component 3007 having a central bore 3011 embodied as an orifice extending through a generally central portion of the upper plunger component 3007. In some embodiments, the central bore 3011 may allow for the sample to pass into the example aerosol collection device 3020 through the flow channel. In various embodiments, the central bore 3011 may be configured to receive at least a portion of a sample transfer adapter (e.g., a mask component, a sampling tunnel, a sampling hood, and/or the like) so as to at least partially secure the sample transfer adapter relative to the device body 3026 of the aerosol collection device 3020. For example, in some embodiments, a sampling channel of an exemplary sample transfer adapter may be mechanically secured within the central bore 3011 of the exemplary upper plunger component 3007 via various means, as described herein, such that an air flow path extending from a sample outlet of the sampling channel to the central bore 3011 of the aerosol collection device 3020, as described herein, may remain at least substantially unobstructed. For example, a user may exhale into the sample transfer adapter (e.g., a mask component and the sample (e.g. breath) may pass through both the sample transfer adapter (e.g., through the sample outlet of the sampling channel) and the central bore 3011 of the flow channel.

In various embodiments, the example aerosol collection device 3020 may be configured such a sample received by the upper plunger component 3007 may flow through central bore 3011 to a central passageway 3017A and 3017B of device body 3026 as part of the flow channel. As described in further detail herein, in some embodiments, central passageway 3017A and 3017B of device body 3026 may comprise a tubular channel extending along an at least substantially central axis of the device body 3026 that allows air to pass therethrough. For example, in various embodiments, central passageway 3017A and 3017B may define an air flow path that extends between the upper plunger component 3007 and a bottom portion of the aerosol collection device 3020 (e.g., a valve support annulus element) such that a sample of air received by the device body 3026 via the central bore 3011 may be directed to the bottom portion of the aerosol collection device 3020 (e.g., toward a bottom surface of the interior portion of the device body 3026). In various embodiments, a bottom portion of the aerosol collection device 3020 (for example, within the valve support annulus element) may be embodied as a breathalyzer mixing chamber.

For example, in various embodiments, the mixing chamber of an exemplary aerosol collection device 3020 may comprise at least a portion of the aerosol collection device 3020 components configured to enable the dynamic aerosol capture and/or collected sample extraction functionalities of the exemplary aerosol collection device 3020, including at least valve support annulus element 3024, sample distribution annulus element 3023, filter component 3005, and/or the like. As described in further detail herein, a filter component 3005 configured to receive the air sample and capture at least a portion of the aerosols present within the sample may be disposed within the bottom portion (e.g., the mixing chamber) of an aerosol collection device 3020.

Figure 31B:
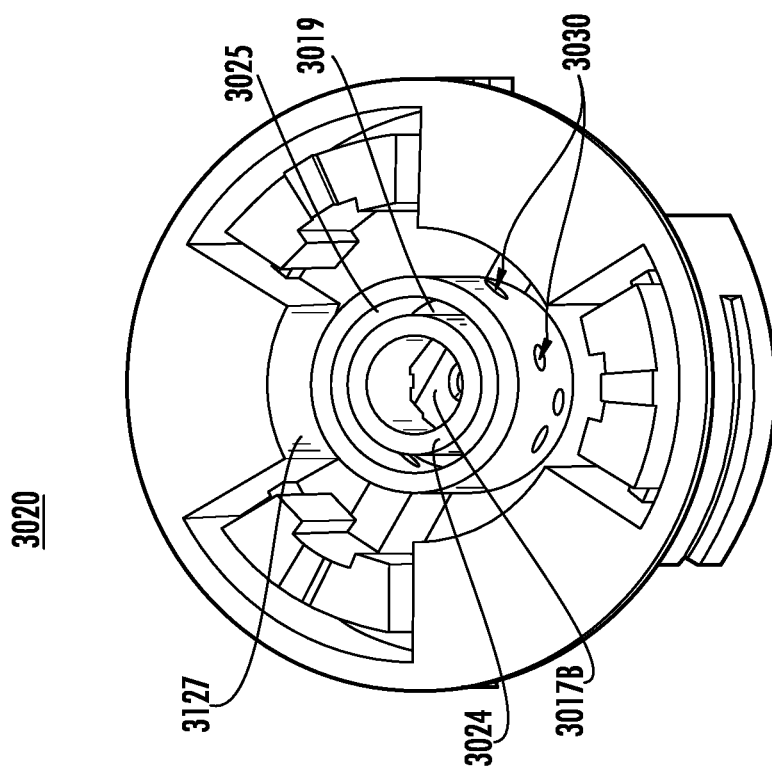
FIG. 31A and FIG. 31B illustrate example views of at least a portion of an example aerosol collection device in accordance with various examples of the present disclosure.

In various embodiments, an air sample flowing along central passageway 3017B may pass the gap between valve component 3018 and the tube component 3050, may then be passed into a valve support annulus element 3024 defining a terminal end of the central passageway 3017B disposed within a bottom portion of the device body. In various embodiments, the valve support annulus element 3024 may comprise a tubular channel arranged in an at least substantially coaxial configuration relative to the central passageway 3017B along the central axis of the device body 3026. The valve support annulus element 3024 may be configured to receive an air sample flowing along the flow channel at least partially defined by the central passageway 3017B. In various embodiments, an exemplary valve support annulus element 3024 may comprise one or more outlets distributed annularly about an end portion of the substantially cylindrical sidewall thereof. For example, as illustrated in FIG. 30 to FIG. 31B, in various embodiments, the one or more outlets of the central passageway may comprise a plurality of outlets collectively configured to dispense a sample received by the valve support annulus element 3024 in an at least substantially even annular distribution.

In various embodiments, the aerosol collection device 3020 may be configured such that the sample dispensed from the one or more outlets 3031 of the valve support annulus element 3024 may be provided to a sample distribution annulus element 3023. In various embodiments, a sample distribution annulus element 3023 may be configured to further facilitate an at least substantially even annular distribution of the air sample as the sample travels in a radially outward direction toward a filter component 3005 of the aerosol collection device 3020. As described herein, sample distribution annulus element 3023 may facilitate an at least substantially uniform annular distribution of the sample throughout a filter component 3005 positioned annularly around the exterior of the sample distribution annulus element 3023. In various embodiments, the sample distribution annulus element 3023 may comprise a sample distribution annulus element sidewall 3025. The sample distribution annulus element sidewall 3025 of the sample distribution annulus element 3023 may at least partially define an interior chamber cavity embodied as an interior volume within the hollow central portion of the sample distribution annulus element sidewall 3025. In various embodiments, the sample distribution annulus element 3023 may be positioned within the device body 3026 such that a central axial of the sample distribution annulus element sidewall 3025 is at least substantially coaxial relative to the valve support annulus element 3024, such as, for example, in a centered position about the central axis of the device body 3026. In such an exemplary configuration, the sample distribution annulus element sidewall 3025 may be defined at least in part by an inner diameter that is at least substantially larger than an outer diameter of the valve support annulus element 3024, such that the sample distribution annulus element sidewall 3025 may surround at least a portion of the valve support annulus element 3024. For example, the aerosol collection device 3020 may be configured such that an inner surface of the sample distribution annulus element sidewall 3025 is separated from the exterior surface of the valve support annulus element 3024 by a gap defined in the radial direction relative to the central axis of the two coaxial components. For example, in various embodiments, the radial gap between the sample distribution annulus element sidewall 3025 and the exterior of the valve support annulus element 3024 may comprise an at least substantially uniform distance throughout at least a portion of the length of the sample distribution annulus element sidewall 3025 (e.g., measured in a length direction parallel to the central axis of the sample distribution annulus element sidewall 3025). As an example, the radial gap between the sample distribution annulus element sidewall 3025 and the exterior of the valve support annulus element 3024 may be defined by an at least substantially uniform radial distance throughout at least an annular portion of the sample distribution annulus element sidewall 3025 (e.g., measured in an annular about the central axis of the sample distribution annulus element sidewall 3025).

In various embodiments, the radial gap between the sample distribution annulus element sidewall 3025 and the exterior of the valve support annulus element 3024 may define an open annulus 3019 that extends annularly around the entirety of the interior surface of the sample distribution annulus element sidewall 3025. In various embodiments, the open annulus 3019 may be fluidly connected to the one or more outlets 3031 of the valve support annulus element 3024 such that the air sample dispensed from the one or more outlets 3031 may be distributed throughout the open annulus 3019. For example, the open annulus 3019 may define at least a portion of the interior chamber cavity of the sample distribution annulus element 3023. In such an exemplary configuration, an air sample, upon being dispensed from the one or more outlets 3031, may initially be retained within the interior chamber cavity of the sample distribution annulus element 3023.

In various embodiments, an aerosol collection device 3020 may comprise one or more filter components configured to capture at least a portion of the aerosols present within a sample received by the aerosol collection device 3020. For example, in various embodiments, the filter component may comprise an at least substantially porous material such that a sample comprising one or more aerosols may be received by the filter component and retrained by the filter component. In some embodiments, the one or more aerosols may travel along at least a portion of the filter component, as described herein. In various embodiments, the aerosol collection device 3020 may be configured such that a cylindrical filter component 3005 may be positioned at least substantially adjacent the outer surface of the sample distribution annulus element sidewall 3025. For example, at least a portion of the interior surface of the cylindrical filter component 3005 may define a receiving face that may be positioned against the outer surface of the sample distribution annulus element sidewall 3025 such that the filter component 3005 is physically engaged with the sample distribution annulus element sidewall 3025.

Further, in various embodiments, as shown in the specific exemplary aerosol collection device illustrated in FIG. 31B, an aerosol collection device 3020 (e.g., a device body 3026) may comprise a filter support body element 3127 embodied as a material recess in which at least a portion of a cylindrical filter component 3005 may be disposed. For example, a filter support body element 3127 may be arranged immediately adjacent the outer surface of the sample distribution annulus element sidewall 3025 that extends around at least a portion of the perimeter of the sample distribution annulus element sidewall 3025. The filter support body element 3127 may be configured to receive at least a portion of a cylindrical filter component 3005 and further at least partially secure the filter component 3005 relative to the sample distribution annulus element 3023 such that that the filter component 3005 is disposed at least substantially adjacent the outer surface of the sample distribution annulus element sidewall 3025.

As described herein, a sample distribution annulus element 3023 of an exemplary aerosol collection device 3020 may be configured to facilitate an at least substantially even annular distribution of the air sample to a filter component 3005 positioned at least substantially adjacent thereto. As described herein, in various embodiments, the filter component 3005 may comprise a wetted configuration, where the filter component 3005 may absorb at least part of the buffer solution released from one or more capsule components as described in detail herein. In some embodiments, a volume of buffer solution is disposed throughout an interior portion of the filter component 3005 (for example, a side of the filter component 3005 that is close to the sample distribution annulus element) and/or an external portion of the filter component 3005 (for example, a side of the filter component 3005 that is opposite to the interior portion and close to the vent channel).

Figure 31A:
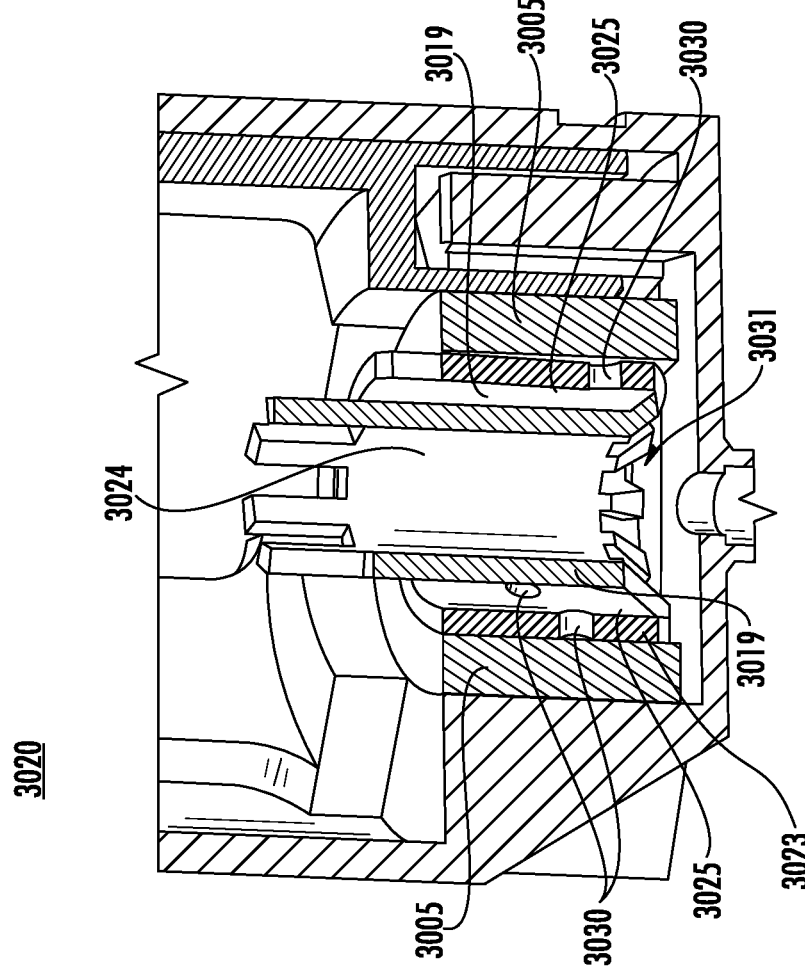

In the example shown in FIG. 31A and FIG. 31B, the sample distribution annulus element sidewall 3025 may comprise a plurality of holes 3030. For example, after an user provides a sample to the example aerosol collection device 3020 (for example, by blowing an exhale breath) into the example aerosol collection device 3020, the sample (for example, the exhale breath) may form one or more bubbles in the buffer solution (for example, as the sample flows through the one or more outlets 3031). In some embodiments, upon receiving a sample from an adjacent hole of the plurality of holes 3030, the filter component 3005 may be configured such that a bubble forms within and/or travels to the volume of solution therein and captures the sample (including, for example, one or more aerosols present in the sample). For example, after an user provides a sample to the example aerosol collection device 3020 (for example, by blowing an exhale breath) into the example aerosol collection device 3020, the sample (for example, the exhale breath) may flow through the one or more outlets 3031 of the valve support annulus element 3024 and enter into the open annulus 3019. The sample may further flow through the plurality of holes 3030 of the sample distribution annulus element sidewall 3025, forming one or more bubbles.

In some embodiments, the one or more aerosols within the sample may be disposed within the bubbles that engage with the solution in the filter component 3005. For example, the filter component 3005 may be configured to allow an air bubble therein to flow (e.g., rise) along a vertical direction through an interior portion of the body of the filter component 3005, while also being configured to capture one or more aerosols present within the air bubble in the filter component. In some embodiments, the filter component 3005 may break air bubbles that exceeds a size limit, thereby reducing the possibility that aerosol droplets can pass through the filter component 3005. In some embodiments, the filter component 3005 may be configured to increase a surface-to-volume ratio of the air bubbles disposed therein. Accordingly, in such an exemplary circumstance, the filter component 3005 may be configured to increase the mass transfer rate associated with the aerosol present within the air bubble such that the aerosol may be separated from the air bubble and captured within the volume of liquid present within the filter component. As described herein, the buffer solution distributed throughout the filter component 3005 may cause the captured aerosol to be at least substantially retained into a sample liquid that includes at least a portion of the biological characteristics of the aerosol as originally received.

In various embodiments, the sample distribution annulus element 3023 may comprise one or more sample distribution elements configured to facilitate an at least substantially uniform annular distribution of the sample throughout filter component 3005. For example, an exemplary sample distribution annulus element may comprise one or more holes 3030 extending through a sample distribution annulus element sidewall 3025 (e.g., between the inner surface and the outer surface of sample distribution annulus element sidewall 3025) so as to fluidly connect the open annulus 3019 to the filter component 3005. More specifically, the one or more holes 3030 extending through the sample distribution annulus element sidewall 3025 may provide a fluid connection between the open annulus 3019 and the filter component 3005 such that at least a portion of a sample present within the open annulus 3019 may flow through an orifice within the sample distribution annulus element sidewall 3025 and engage a portion of the receiving face of the filter component 3005 positioned directly adjacent the orifice. As an example, in various embodiments, the one or more holes 3030 may provide the only fluid connection between the sample distribution annulus element 3023 and the filter component 3005 adjacent thereto such that at least substantially all of the sample provided to the sample distribution annulus element 3023 (e.g., the sample received within the open annulus 3019) may be dispensed from the sample distribution annulus element 3023 and delivered to the filter component 3005 via the one or more holes 3030.

As illustrated in FIG. 30 to FIG. 31B, in various embodiments, the one or more orifices of an exemplary sample distribution annulus element 3023 may comprise a plurality of orifices embodied as a plurality of holes 3030 distributed throughout the sample distribution annulus element sidewall 3025. As a nonlimiting example, in various embodiments, the plurality of holes 3030 may comprise at least substantially between 8 and 40 holes (e.g., between 16 and 24 holes) distributed throughout the sample distribution annulus element sidewall 3025.

In various embodiments, one or more of the holes of the plurality of holes 3030 may embody a physical configuration that is either the same as or different from a physical configuration of one or more of the other holes of the plurality of holes 3030. For example, the physical configuration of a hole as described herein may be defined at least in part by a surface area, a shape, an angular direction at which the hole extends through the thickness of the sample distribution annulus element sidewall 3025 (e.g., in a linear direction perpendicular to a central axis of the device body 3026 and/or one that defines an angle away from the horizontal plane, and/or the like). In various embodiments, a surface area of one or more holes of the plurality of holes 3030 may be configured so as to enable a specific mass flow rate through the sample distribution annulus element sidewall 3025. For example, in various embodiments, the cumulative surface area of each of the plurality of holes 3030 distributed about the sample distribution annulus element sidewall 3025 may comprise at least substantially between 20% and 100% (e.g., between 50% and 100%) of the total surface area of an aerosol collection device 3020 sample inlet (e.g. central bore 3011). Further, as an example, in various embodiments the cumulative surface area of each of the plurality of holes 3030 distributed about the sample distribution annulus element sidewall 3025 may be at least substantially equal to a surface area of the central bore 3011 of exemplary aerosol collection device 3020. In various embodiments, the cumulative surface area of one or more holes of the plurality of holes 3030 may be configured so as to enable a specific pressure to drop over the exemplary sample distribution annulus element 3023. In various embodiments, one or more of the holes of the plurality of holes 3030 may comprise a cross-sectional area that is uniform throughout the thickness of the sample distribution annulus element sidewall 3025 (e.g., between an inner surface and an outer surface of the sample distribution annulus element sidewall 3025). Further, in various embodiments, one or more of the holes of the plurality of holes 3030 may comprise a cross-sectional area that is variable at one or more locations along the thickness of the sample distribution annulus element sidewall 3025.

Further, in various embodiments, one or more of the holes of the plurality of holes 3030 may comprise a cross-sectional area that is uniform throughout the thickness of the sample distribution annulus element sidewall 3025 (e.g., between an inner surface and an outer surface of the sample distribution annulus element sidewall 3025). Further, in various embodiments, one or more of the holes of the plurality of holes 3030 may comprise a cross-sectional area that is variable at one or more locations along the thickness of the sample distribution annulus element sidewall 3025.

In various embodiments, the sample distribution annulus element sidewall 3025 may be defined at least in part by a sidewall length, as measured in a direction parallel to the central axis of the device body 3026. For example, one or more of the plurality of holes 3030 may be positioned along the length of the sample distribution annulus element sidewall 3025 at a location defined at least in part by a perpendicular distance between the respective hole and a top surface of the filter component 3005 adjacent thereto. For example, the position of a hole of the plurality of holes 3030 relative to the length of the sample distribution annulus element sidewall 3025 may define the vertical distance along which a sample dispensed through the hole and into the adjacent filter component 3005 must travel within the body of the filter component in order to reach an upper boundary of the filter component. In various embodiments, one or more of the plurality of holes 3030 disposed within the sample distribution annulus element sidewall 3025 may be positioned along the sample distribution annulus element sidewall 3025 such that the distance between the one or more holes and the top surface of the sample distribution annulus element sidewall 3025, as measured perpendicularly, may be at least substantially between 50% and 100% (e.g., between 50% and 75%) of the total the length of the sample distribution annulus element sidewall 3025. That is, for example, in various embodiments, one or more of the plurality of holes 3030 disposed within the sample distribution annulus element sidewall 3025 may be positioned about a lower half of the sample distribution annulus element sidewall 3025 (e.g., a half of the sample distribution annulus element sidewall 3025, as measured vertically along the length of the sample distribution annulus element sidewall 3025, positioned relatively proximate the bottom surface of the device body 3026).

In various embodiments, the position of one or more of the plurality of holes relative to the total length of the sample distribution annulus element sidewall 3025 and/or the filter component 3005 may be either the same as or different from the position of one or more of the other holes of the plurality of holes 3030.

As described in further detail herein, in some embodiments, aerosols may be captured in the filter component 3005, and air may be removed from the aerosols in the form of bubbles through the filter component 3005. The air separated from the aerosols may then enter into a breathalyzer chamber 3021. Referring to the example aerosol collection device 3020 shown in FIG. 30, the breathalyzer chamber 3021 may be positioned above the filter component 3005, thus enabling the air to escape from the filter component 3005 and into the breathalyzer chamber 3021.

As further described herein, In some embodiments, an aerosol-removed volume of air within the breathalyzer chamber 3021 may further be passed through the one or more vent channels 3027 configured to dispense at least a portion of a volume of air within the aerosol collection device 3020 into an ambient environment. For example, the one or more vent channels 3027 may comprise one or more orifices positioned about an exterior breathalyzer surface of the upper plunger component 3007 and may be configured to provide fluid communication between the breathalyzer chamber 3021 and the ambient environment such that an aerosol-removed volume of air within the breathalyzer chamber 3021 may be dispensed into the ambient environment via the one or more orifices in the upper plunger component 3007.

In various embodiments, an exemplary aerosol collection device may comprise a device body 3026 comprising an aerosol collection device housing configured to store various components of an exemplary aerosol collection device 3020 within an interior portion of the housing. As described herein, an aerosol collection device 3020 may be configured to receive an air sample (e.g., from a sample transfer adapter) through a upper plunger component 3007 and deliver the received sample along an air flow path or flow channel throughout various components disposed within the housing of the device body 3026, such as, for example, filter component 3005, sample distribution annulus element 3023, and/or the like), in order to capture in the filter component 3005 at least a portion of aerosols present within the sample as received. In various embodiments, the aerosol collection device 3020 may be configured to receive a single air sample continuously provided to the aerosol collection device 3020 over a length of time or a plurality of air samples provided serially to the aerosol collection device 3020 over time. In such an exemplary circumstance, the air sample(s) provided to the aerosol collection device 3020 over time may repeatedly pass through the filter component 3005 housed within the device body 3226, as described herein, such that aerosols captured by the filter component 3005 over time may accumulate within the filter component 3005. In such an exemplary configuration, the accumulated aerosols disposed within the filter component may affect one or more physical characteristics of the filter component 3005 and/or a volume of buffer solution present within the filter component 3005. For example, in various embodiments, one or more one or more physical characteristics of the filter component 3005 and/or a volume of buffer solution therein, such as, for example, weight, volume, particulate concentration, color, and/or the like may change over time as the amount of aerosols captured within the wetted filter component 3005 (e.g., a filter component 3005 that has a volume of buffer solution disposed therein) increases.

Figure 32B:
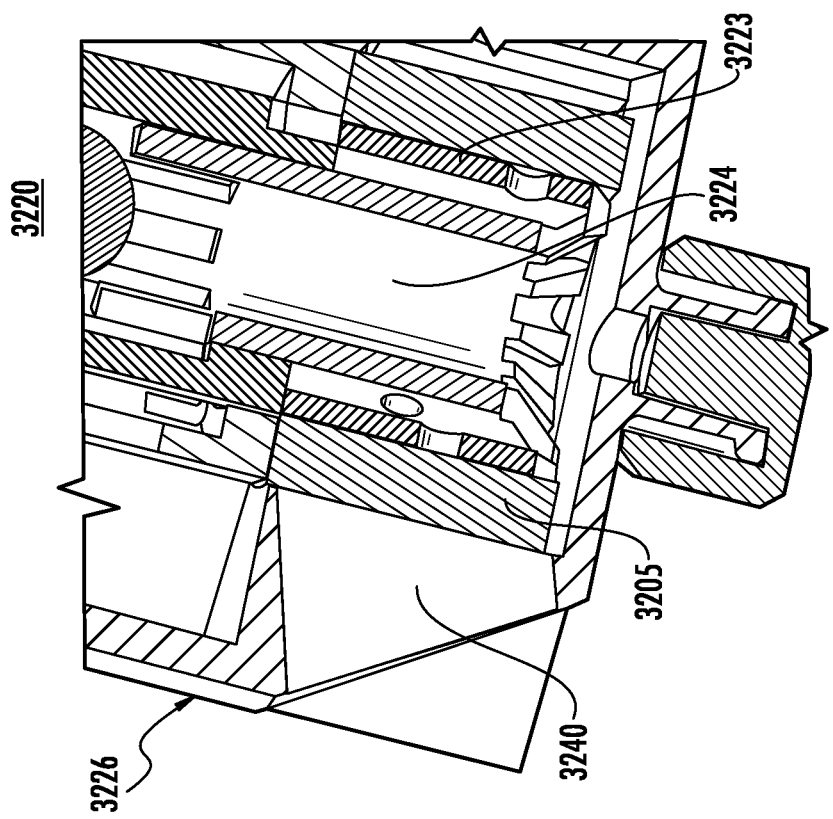
FIG. 32A, FIG. 32B, and FIG. 32C illustrate example views of at least a portion of an example aerosol collection device in accordance with various examples of the present disclosure.
Figure 32A:
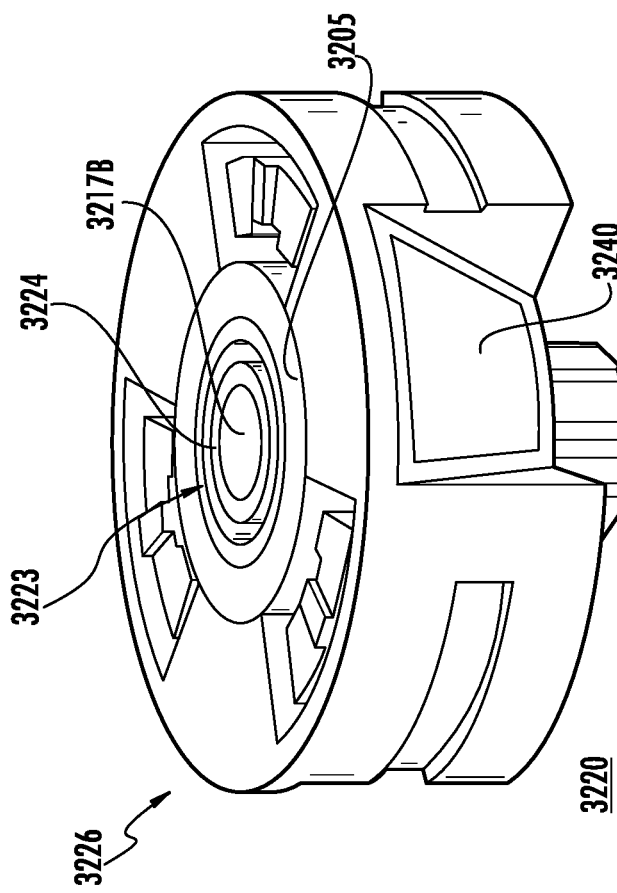

In various embodiments, an exemplary aerosol collection device 3020 may comprise a means for monitoring one or more characteristics of the wetted filter component 3005 disposed within the device body 3226 over time without interrupting the operation of the aerosol collection device 3220. Referring now to FIG. 32A, a portion of an example perspective cross-sectional view of an example aerosol collection device 3220 is illustrated. As illustrated, various components of the exemplary aerosol collection device 3220 are disposed within the housing of the device body 3226, such as, for example, a central passageway 3217B, a valve support annulus element 3224, a sample distribution annulus element 3223, and a filter component 3205 configured according to various embodiments described herein. As an example, the housing of the device body 3226 (for example, a vessel component) may comprise an observation orifice 3240 positioned about at least a portion of an external surface of the device body 3226 and extending through a thickness of the device body 3226. In various embodiments, an observation orifice 3240 may facilitate a line of sight between a vantage point within an ambient environment external to the device body 3226 and one or more aerosol collection device 3220 components housed within the device body 3226. For example, an observation orifice 3240 may be provided at a surface that is positioned at least substantially adjacent the one or more aerosol collection device 3220 components within the device body 3226 for which visibility from an external vantage point is desired. As an example, the exemplary aerosol collection device 3220 illustrated in FIG. 32A and FIG. 32B comprises an observation orifice 3240 configured to provide a line of sight from a remote vantage point within an ambient environment to at least a portion of the filter component 3205 arranged adjacent the observation orifice 3240. For example, an exemplary observation orifice 3240 may embody a viewing window configured such that a user may see at least a portion of a filter component 3205 disposed within the housing of the device body 3226 without requiring disassembly and/or interruption of the operation of the aerosol collection device 3220. In various embodiments, the observation orifice 3240 may comprise at least one transparent element (e.g., transparent glass, transparent plastic, and/or the like) configured to cover the surface area of the observation orifice 3240 so facilitate visibility of the filter component 3205 while preventing unwarranted air leakage and/or contamination of the aerosol collection device 3220 through the observation orifice 3240. Further, in various embodiments, the at least one transparent element of an observation orifice 3240 may be configured to visually magnify at least a portion of the one or more internal breathalyzer components (e.g., filter component 3205) at which the observation orifice 3240 is directed.

As described in further detail herein, the aerosol collection device may be configured such that one or more samples of air containing a plurality of aerosols may pass through a wetted filter component 3205 configured to capture at least a portion of the aerosols within the samples passing therethrough, such that a captured aerosol becomes embedded within the thickness of the filter component 3205. Over time, a plurality of captured aerosols may accumulate within the thickness of the filter component 3205 such that the aerosols may react with the buffer solution dispersed throughout the wetted filter component 3205. In various embodiments, the accumulated plurality of aerosols captured within the filter component 3205 thickness may cause the physical appearance of the filter component 3205 to at least partially change due at least in part to, as examples, the presence or an increased concentration of aerosols present within the filter component 3205, a chemical reaction between one or more of the accumulated plurality of aerosols and the buffer solution, and/or the like. For example, in such an exemplary circumstance, one or more aspects of the physical appearance of the filter component 3205, such as, for example, color, transparency, texture, uniformity, and/or the like, may undergo a noticeable change that may be visible to a user observing the filter component through an observation orifice 3240.

Figure 32C:
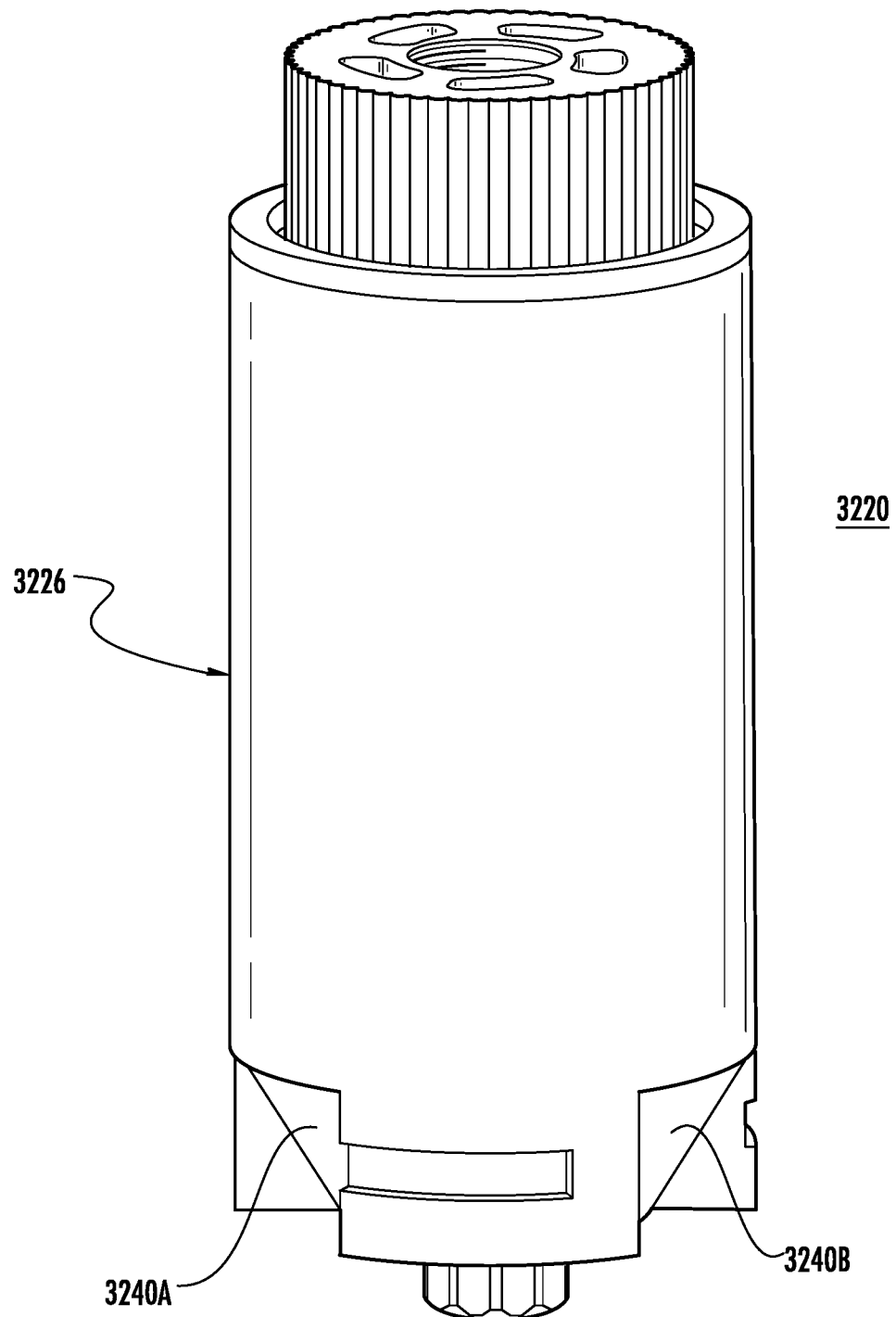

In various embodiments, an exemplary observation orifice may comprise any applicable shape or form configured to make visible to a user one or more corresponding breathalyzer components within the device body 3226. Further, in various embodiments, as illustrated in FIG. 32C, an exemplary aerosol collection device 3220 may comprise a plurality of observation orifices 3240A, 3240B. For example, in various embodiments, each of the plurality of observation orifices 3240A, 3240B may be configured to provide a distinct line of sight to a respective breathalyzer component within the housing/vessel component of the device body 3226 (e.g., a filter component 3205 and a breathalyzer chamber, respectively). Further, in various embodiments, each of the plurality of observation orifices 3240A, 3240B may be configured to provide distinct line of sight to a respective portion of the same breathalyzer component within the housing/vessel component of the device body 3226 (e.g., a first portion of filter component 3205 and a second portion of filter component 3205, respectively). For example, as shown in FIG. 32C, a first observation orifice 3240A may provide a line of sight from outside the housing/vessel component/device body of the aerosol collection device 3220 to a first portion of filter component 3205, while a second observation orifice 3240B may provide a distinct line of sight from outside the housing/vessel component of the aerosol collection device 3220 to a second portion of filter component 3205.

In various embodiments, subsequent to a sample being collected by the aerosol collection device 3220, the aerosol collection device 3220 may be configured to facilitate an extraction operation, and at least a portion of a sample liquid may be extracted from the device body 3226. For example, as described in further detail herein, the sample liquid may be extracted from the aerosol collection device 3220 by an example sample extraction device, such as, but is not limited to, an extraction cartridge. In various embodiments, an exemplary extraction cartridge may be removably attached to a portion of the device body or vessel component (e.g., an extraction opening disposed about a bottom portion of device body 3226) such that the extraction cartridge may be placed in fluid communication with a bottom portion of the interior of the device body 3226. The sample liquid may be transmitted from the device body 3226 to the extraction cartridge configured to store the extracted volume of sample liquid therein for subsequent analysis and/or experimentation operations.

Figure 33A:
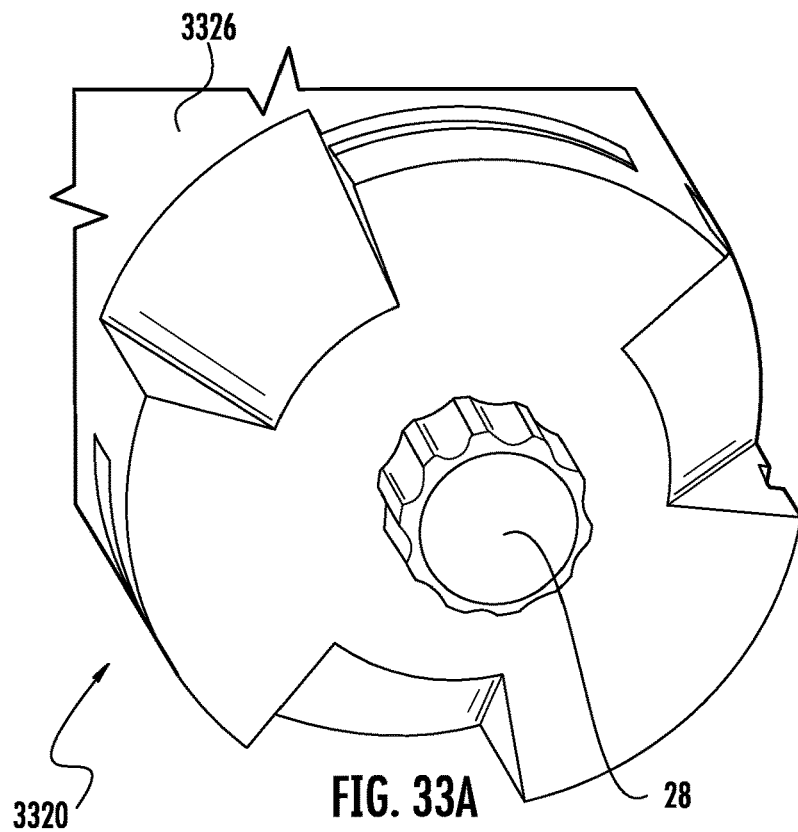
FIG. 33A to FIG. 33B illustrate example views of at least a portion of an example aerosol collection device in accordance with various examples of the present disclosure.
Figure 33B:
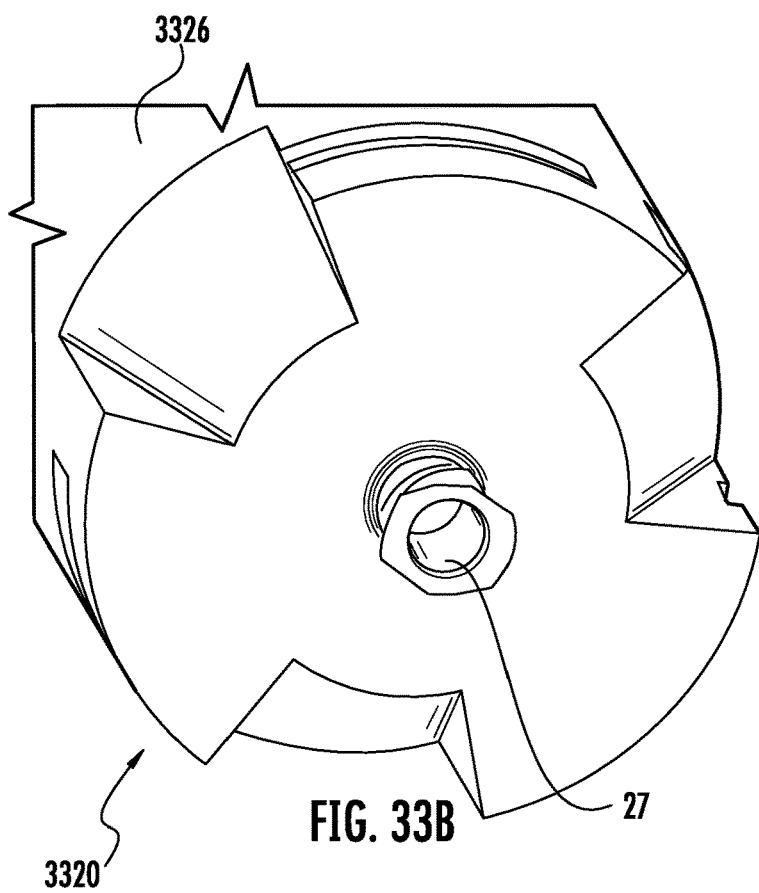

Referring now to FIG. 33A to FIG. 33B, a portion of example perspective views of the example aerosol collection device 3320 is illustrated.

In various embodiments, an exemplary aerosol collection device 3320 may comprise a sample liquid extraction outlet 27 positioned at a central portion of a bottom surface of the device body 3326. For example, in various embodiments, the sample liquid extraction outlet 27 may comprise a tubular channel arranged in an at least substantially coaxial configuration relative to the central axis of the device body 3326. Further, in various embodiments, at least a portion of the sample liquid extraction outlet 27 may protrude from the bottom surface of the device body 3326 in an outward direction away from the device body. In various embodiments, the sample liquid extraction outlet 27 may comprise an internal volume of at least substantially between 0.05 mL and 0.3 mL (e.g., between 0.1 mL and 0.2 mL). In various embodiments, the device body 3326 of an exemplary aerosol collection device 3320 may be configured to accommodate a sample liquid volume of at least substantially between 2 mL and 10 mL (e.g., between 3 mL and 4 mL).

As illustrated, in various embodiments, the aerosol collection device 3320 may further comprise a lock component 28 configured to be detachably secured relative to the sample liquid extraction outlet 27. For example, the lock component 28 may be configured to at least substantially plug the tubular channel of the sample liquid extraction outlet 27 so as to prevent a sample liquid from flowing through the sample liquid extraction outlet 27 when the lock component 28 is attached thereto. As an example, the lock component 28 may comprise a luer lock. In some embodiments, lock component 28 may be attached to the sample liquid extraction outlet 27 via various means, including but not limited to, mechanical means (for example, lock component 28 may be screwed onto the sample liquid extraction outlet 27 via threads provided about an exterior surface of the sample liquid extraction outlet 27).

As described herein, the sample liquid extraction outlet 27 may embody a conduit element configured to facilitate the delivery of a sample liquid disposed within an internal portion of the device body 3326 to an exemplary extraction cartridge fluidly and/or mechanically connected thereto. Accordingly, in various embodiments, the aerosol collection device 3320 may comprise a seal element (e.g., a groove component, as described herein), provided along a portion of the bottom surface of the interior portion of the device body 3326 so as to fluidly isolate the interior portion of the device body from the sample liquid extraction outlet 27. Such an exemplary configuration may prevent a sample liquid compressed from the filter component, as described herein, and provided within the bottom portion of the device body 3326 from passing through the sample liquid extraction outlet 27 without first puncturing the seal element to open an area through which the sample liquid may flow.

Figure 34A:
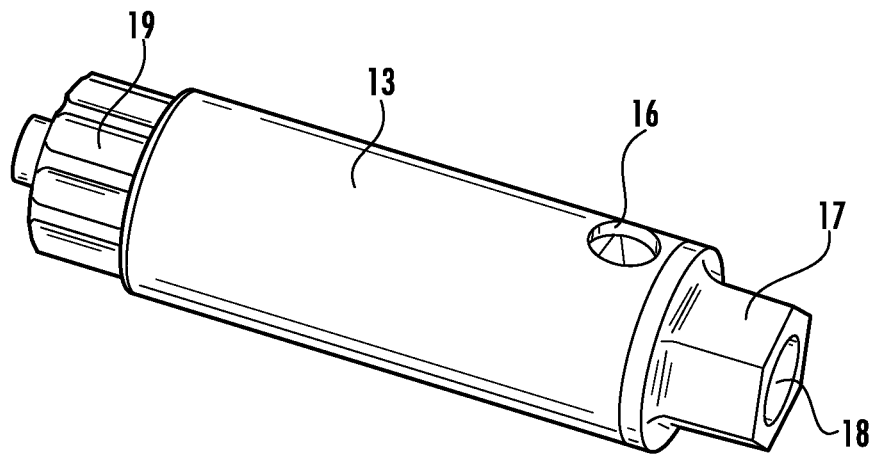
FIG. 34A to FIG. 34B illustrate example views of an example extraction cartridge in accordance with various examples of the present disclosure.
Figure 34B:
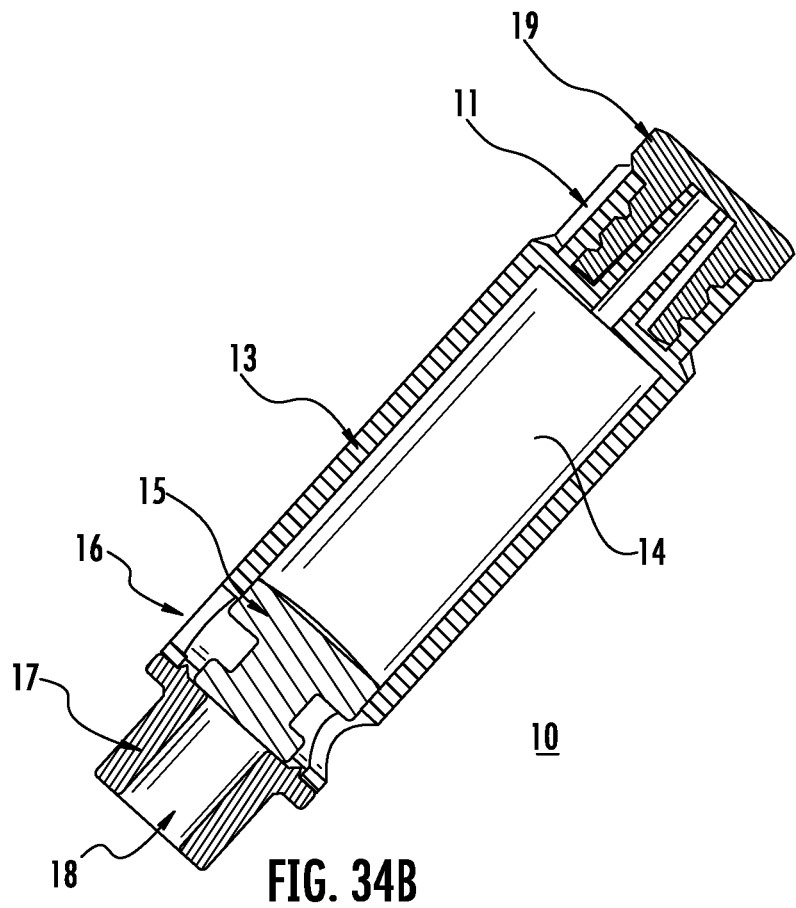

Referring now to FIG. 34A to FIG. 34B, example perspective and cross-sectional views of the example extraction cartridge 10 are illustrated.

In various embodiments, an exemplary extraction cartridge 10 may comprise a cartridge body 13 that defines at least a portion of the exterior of the extraction cartridge. As illustrated, in various embodiments, a cartridge body 13 may comprise a substantially cylindrical exterior sidewall and an interior body chamber 14 defined by the hollow interior portion of the cylindrical sidewall. For example, interior body chamber 14 of the cartridge body 13 may comprise a cylindrical chamber having an outer perimeter defined at least in part by the interior surface of the cylindrical sidewall of the cartridge body 13. In various embodiments, the cartridge body 13 may be configured to receive a volume of fluid (e.g., sample liquid extracted from an aerosol collection device) within the interior body chamber 14 via sample liquid inlet 11, as described in further detail herein.

In various embodiments, an exemplary extraction cartridge 10 may comprise an extraction plunger 15 disposed within the interior body chamber 14 of the cartridge body 13. In various embodiments, extraction plunger 15 may embody a piston component having have a range of motion within the interior body chamber 14 that is defined at least in part by the interior surface of the cylindrical sidewall of the cartridge body 13. For example, an outer perimeter of the face of the extraction plunger 15 may be physically engaged with the interior surface of the cylindrical sidewall of the cartridge body 13 so as to define an air-tight seal between the face of the extraction plunger 15 and the cylindrical sidewall of the cartridge body. For example, in such an exemplary circumstance a local pressure and volume may be defined within an active portion of the interior body chamber 14 extending between the sample liquid inlet 11 and the face of the extraction plunger 15. In various embodiments, the extraction cartridge 10 may be configured such that as the extraction plunger 15 moves along the interior body chamber 14 in an axial direction (e.g., along a central axis of the cylindrical sidewall of the cartridge body 13) one or more local conditions (e.g., a local pressure, a volumetric capacity, and/or the like) within the active portion of the interior body chamber 14 (e.g., defined between the between the sample liquid inlet 11 and the face of the extraction plunger 15) may change based at least in part on the position of the extraction plunger 15 within the interior body chamber 14. As an example, in various embodiments, an exemplary extraction cartridge 10 may embody a syringe component.

In various embodiments, the extraction cartridge 10 may comprise a cartridge body end cap 17 removably secured to a distal end of the cylindrical cartridge body 13. For example, the cartridge body end cap 17 may be configured to at least partially restrict the range of motion of the extraction plunger 15 such that the extraction plunger 15 is retained within the interior body chamber 14 of the cartridge body 13. Further, in various embodiments, the cartridge body end cap 17 may comprise a guide rod aperture 18 extending therethrough in a coaxial direction relative to the central axis of the interior body chamber 14. For example, in various embodiments, an exemplary extraction cartridge 10 may comprise a guide rod attached on one end to the extraction plunger 15 and extending, at the other end, through guide rod aperture 18. In such an exemplary circumstance, a user may at least partially control the positioning of the extraction plunger 15 within the interior body chamber 14 by pushing and/or pulling the guide rod into and/or out of guide rod aperture 18. As further illustrated in FIG. 34A, the cartridge body may comprise an observation orifice 16 extending through the cylindrical sidewall of the cartridge body 13 so as to define a line of sight to a distal portion of the interior body chamber 14. For example, in various embodiments, the observation orifice 16 may be configured to define a line of sight to the extraction plunger 15 such that a user may ascertain the position of the extraction plunger within the interior body chamber 14.

Figure 35:
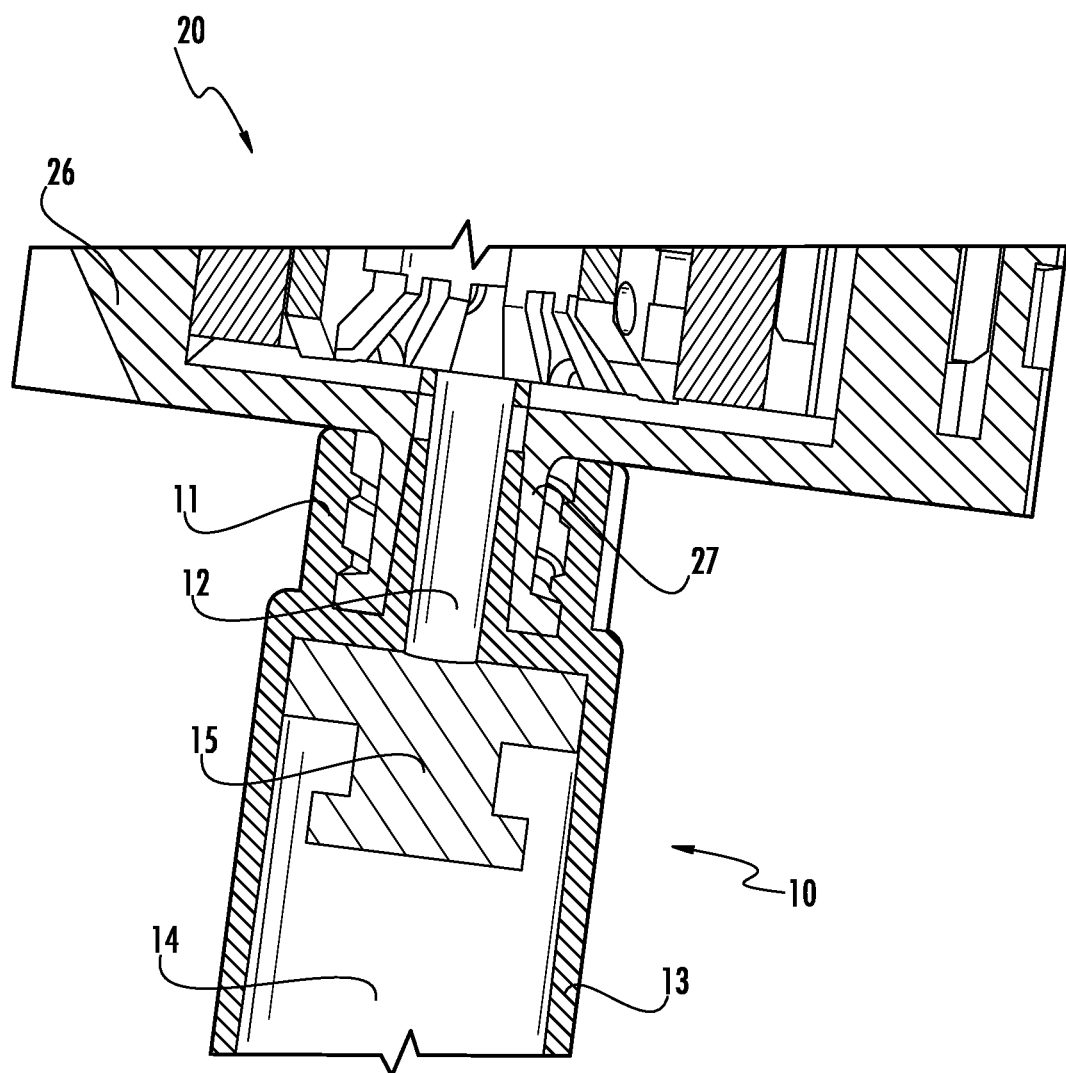
FIG. 35 illustrates an example extraction cartridge in accordance with various examples of the present disclosure.
Figure 36:
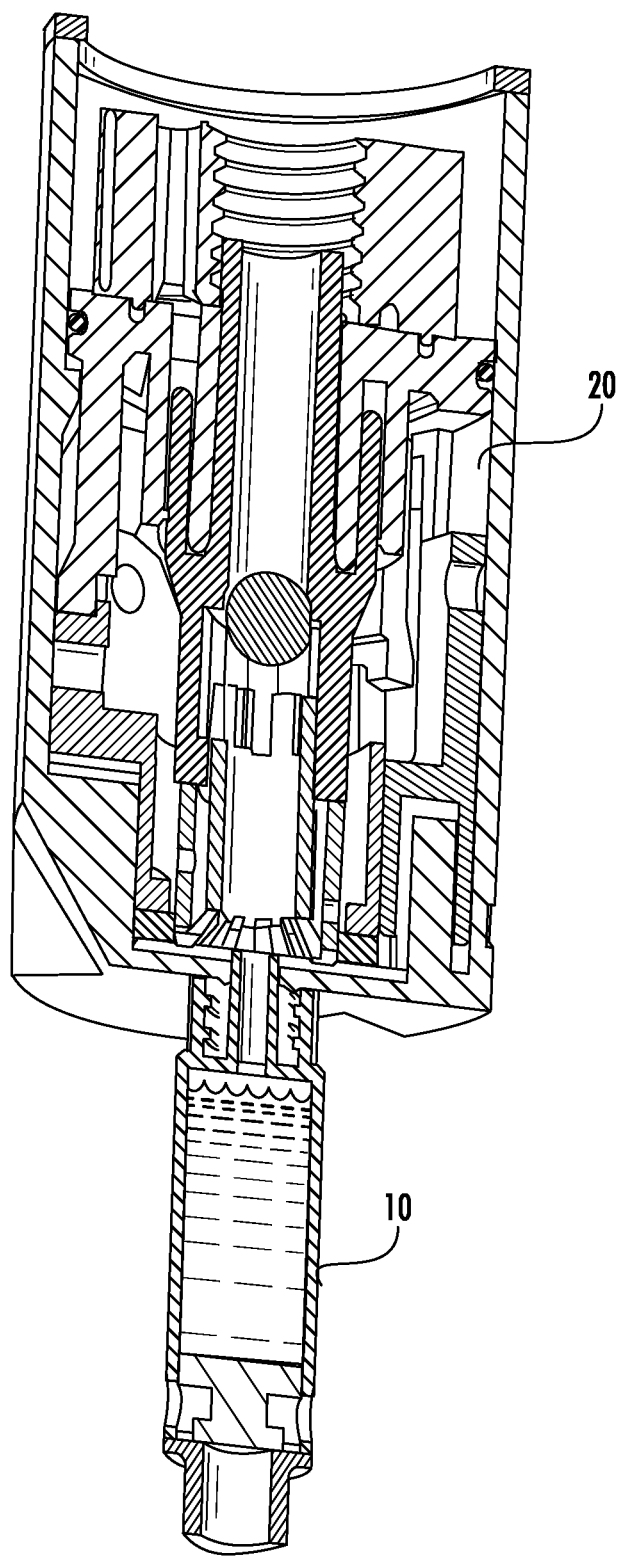
FIG. 36 illustrates an example extraction cartridge and an example device body in accordance with various examples of the present disclosure.

Referring now to FIG. 35 to FIG. 36, a portion of example perspective cross-sectional views of an example extraction cartridge 10 and an example aerosol collection device 20 are illustrated.

As described herein, the sample liquid inlet 11 may embody a conduit element 12 through which a volume of sample liquid extracted from device body 26 may be received by the extraction cartridge 10 and delivered into the interior body chamber 14. As illustrated, the sample liquid inlet 11 may comprise one or more attachment means for mechanically attaching the sample liquid inlet 11 to the sample liquid extraction outlet 27 of device body 26, as described herein, In such an exemplary configuration, the extraction cartridge 10 may be mechanically secured and fluidly connected to the device body 26 of the aerosol collection device 20.

In various embodiments, the extraction cartridge 10 may comprise one or more puncturing elements configured to at least partially extend into the sample liquid extraction outlet 27 of the device body 26 and puncture the seal element extending over the sample liquid extraction outlet 27 so as to produce an opening through which the sample liquid disposed within the device body 26 may flow to the sample liquid extraction outlet 27.

As described herein, an exemplary extraction cartridge 10 may embody a syringe component, such that the extraction cartridge 10 is configured to attach to a sample liquid extraction outlet 27 of an aerosol collection device 20 and extract a volume of sample liquid disposed within the device body 26 by pulling the extraction plunger 15 of the extraction cartridge 10 in a direction away from the sample liquid inlet 11 in order to increase the volumetric capacity within the active portion of the interior body chamber 14 and correspondingly decrease the local pressure therein. In such an exemplary configuration, the local pressure within the active portion of the interior body chamber 14 may drop lower than a corresponding pressure within the device body 26, such that a flow of the sample liquid within the device body 26 may be initiated and the extraction of the entirety of the sample liquid from the aerosol collection device 20 may be executed. As described, in an exemplary circumstance where the pressure within the device body 26 is higher than the local pressure within the active volume of the interior body chamber fluidly connected thereto, the volume of sample liquid within the device body 26 may be dispensed (e.g., extracted) through the sample liquid extraction outlet 27 of the aerosol collection device 20 to the extraction cartridge 10 attached thereto.

In various embodiments, an exemplary extraction cartridge 10 may indicates when the sample liquid extracted from the aerosol collection device 20 occupies at least substantially the entirety of the active volume of the interior body chamber 14 such that no further sample liquid can be extracted by the extraction cartridge 10. For example, an exemplary extraction cartridge 10 may comprise one or more indicating means configured to generate a visual and/or an audio indication, such as, for example, an LED light indicator, an alarm notification, and/or the like, to indicate that the extraction cartridge 10 has reached an operational volumetric capacity. In such an exemplary circumstance, the sample liquid inlet 11 of the exemplary extraction cartridge 10 may be decoupled from the sample liquid extraction outlet 27 of the aerosol collection device 20. Further, in various embodiments where the extraction cartridge has received an extracted sample liquid from an aerosol collection device 20, the attachment means described with respect to the sample liquid inlet 11 may be configured to facilitate the attachment of a cartridge cap element 19 to the sample liquid inlet 11 so as to seal the extracted sample liquid within the interior body chamber 14 of the extraction cartridge 10. In some embodiments, the extracted sample liquid may comprise biological content that can be used for further analysis and downstream diagnostics.

While this specification contains many specific implementation details, these should not be construed as limitations on the scope of any disclosures or of what may be claimed, but rather as descriptions of features specific to particular embodiments of particular disclosures. Certain features that are described herein in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

It is to be understood that the disclosure is not to be limited to the specific examples disclosed, and that modifications and other examples are intended to be included within the scope of the appended claims. Although specific terms are employed herein, they are used in a generic and descriptive sense only and not for purposes of limitation, unless described otherwise.

The invention claimed is:

1. An aerosol collection device comprising:
   an upper plunger component comprising a central annulus portion and an intermedial annulus portion, wherein the central annulus portion is disposed within the intermedial annulus portion, forming a gap between the central annulus portion and the intermedial annulus portion, wherein a sealing ridge is disposed on an inner surface of the intermedial annulus portion; and
   a tube component comprising a vent bluff annulus element, wherein at least a portion of the central annulus portion is positioned within and in contact with the vent bluff annulus element.

2. The aerosol collection device of claim 1, wherein the upper plunger component comprises a plunger head element defining a central bore.

3. The aerosol collection device of claim 2, wherein the tube component comprises a pipe element connected to the central bore and forming a portion of a flow channel for receiving a sample.

4. The aerosol collection device of claim 1, further comprising a sample transfer adapter configured to deliver a sample to a sample inlet of the aerosol collection device, wherein the sample transfer adapter comprises at least one of a sampling tunnel or a mask component.

5. The aerosol collection device of claim 3, wherein a top portion of the pipe element of the tube component is positioned within the central annulus portion of the upper plunger component.

6. The aerosol collection device of claim 1, wherein a gap between a top surface of the vent bluff annulus element and a bottom surface of the intermedial annulus portion define a portion of a vent channel for discharging a sample.

7. The aerosol collection device of claim 1, wherein the central annulus portion and the intermedial annulus portion define a portion of a vent channel for discharging a sample.

8. The aerosol collection device of claim 1, wherein the vent bluff annulus element comprises at least one opening defining a portion of a vent channel for discharging a sample.

9. The aerosol collection device of claim 1, wherein, when a vertical force is exerted on a top surface of the upper plunger component, at least a portion of the vent bluff annulus element of the tube component enters into the gap between the central annulus portion of the upper plunger component and the intermedial annulus portion of the upper plunger component.

10. The aerosol collection device of claim 9, wherein, when the vertical force is exerted on the top surface of the upper plunger component, the sealing ridge moves past an opening on the vent bluff annulus element and blocks a vent channel.

11. The aerosol collection device of claim 1, further comprising:
    a lower plunger component comprising a plurality of plunger support wings, wherein each of the plurality of plunger support wings is positioned between two of a plurality of capsule components, wherein the plurality of capsule components comprises a first capsule component storing a first buffer solution and a second capsule component storing a second buffer solution.

12. The aerosol collection device of claim 11, wherein the lower plunger component and the upper plunger component are housed within a vessel component having at least one vertical lock ridge element and at least one vertical stop ridge element disposed on an inner lateral surface of the vessel component.

13. The aerosol collection device of claim 12, wherein the upper plunger component is configured to translate from a first configuration to a second configuration by a rotational force.

14. The aerosol collection device of claim 13, wherein the upper plunger component comprises at least one leg portion, wherein:
    in the first configuration, a bottom surface of the at least one leg portion is in contact with a top surface of each of the plurality of capsule components; and
    in the second configuration, the bottom surface of the at least one leg portion is in contact with a top surface of each of the plurality of plunger support wings.

15. The aerosol collection device of claim 14, the rotational force causes at least a portion of the at least one leg portion to rotate past the at least one vertical lock ridge element and stop at the at least one vertical stop ridge element.

16. The aerosol collection device of claim 12, wherein a bottom surface of the lower plunger component is in contact with a filter component, wherein the upper plunger component is in contact with a top surface of the lower plunger component.

17. The aerosol collection device of claim 16, wherein in response receiving a vertical force exerted on a top surface of the upper plunger component, the upper plunger component is configured to transfer the vertical force to the lower plunger component and cause a vertical movement of the lower plunger component.

18. The aerosol collection device of claim 16, wherein a sample distribution annulus element is fluidly connected to the filter component, wherein the sample distribution annulus element comprises one or more sample distribution elements configured to distribute at least a portion of the sample to a respective filter portion of a plurality of distributed filter portions defined throughout the filter component.

19. The aerosol collection device of claim 1, further comprising:
   an extraction cartridge attached to a sample liquid extraction outlet of the aerosol collection device via one or more attachment means defined at least in part by the extraction cartridge.

* * * * *